(12) United States Patent
Cheng et al.

(10) Patent No.: US 7,291,482 B2
(45) Date of Patent: Nov. 6, 2007

(54) MUTATIONS AFFECTING PLASMID COPY NUMBER

(75) Inventors: Qiong Cheng, Wilmington, DE (US); Pierre E. Rouviere, Wilmington, DE (US); Luan Tao, Claymont, DE (US); Wonchul Suh, Hockessin, DE (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 496 days.

(21) Appl. No.: 10/735,019

(22) Filed: Dec. 12, 2003

(65) Prior Publication Data

US 2004/0191863 A1    Sep. 30, 2004

Related U.S. Application Data

(60) Provisional application No. 60/434,973, filed on Dec. 20, 2002.

(51) Int. Cl.
   *C12P 21/02* (2006.01)

(52) U.S. Cl. .................... 435/69.1; 435/252.33
(58) Field of Classification Search .................... None
   See application file for complete search history.

(56) References Cited

U.S. PATENT DOCUMENTS

2002/0106800 A1    8/2002    Liaw et al.
2004/0146966 A1*   7/2004    Cheng et al. ............... 435/67

FOREIGN PATENT DOCUMENTS

WO    WO 2004/056974 A2    7/2004
WO    WO 2004/056975 A2    7/2004

OTHER PUBLICATIONS

Glick, B. R., Paternak, J.J. Molecular Biotechnology Principles and Applications of Recombinant DNA, 2nd ed. American Society for Microbiology, Washington, D.C. 1998.
Grabherr et al., Stabilizing Plasmid Copy Number to Improve Recombinant Protein Production, Biotech. Bioeng., vol. 77: pp. 142-147, 2002.
Podkovyrov, S.M. and Larson, A new vector-host system for construction of lacZ transcriptional fusions where only low-level gene expression is desirable, T. J., Gene 156: 151-152, 1995.
Lopilato et al., Mutations in a new chromosomal gene of *Escherichia coli* K-12, pcnB, reduce plasmid copy number of pBR322 and its derivatives, Mol. Gen. Genet. 205: pp. 285-290, 1986.
Lui et al., Genetics and Sequence Analysis of the pcnB Locus, and *Escherichia coli* Gene Involved in Plasmid Copy Number Control, J. Bacteriol., 171: pp. 1254-1261, 1989.
Wrobel et al., Differential amplification efficiency of pMB1 and p15A (ColE1-type) repilicons in *Escherichia coli* stringent and relaxed strains starved for particular amino acids, Microbiol. Res., vol. 152, pp. 251-255, 1997.
Ederth et al., Origin-specific reduction of ColE1 plasmid copy number due to mutations in a distinct region of the *Escherichia coli* RNA polymerase, Mol. Gen Genomics, vol. 267: 587-592, 2002.
Burrows et al., *Pseudomonas aeruginosa* B-Band O-Antigen Chain Length is Modulated by Wzz (Rol), Journal of Bacteriology, Mar. 1997, pp. 1482-1489.
Aleksun et al., Molecular cloning and characterization of *Borrelia burgdorferi* rpoB, Gene 186, 1997, pp. 227-235.
Leeds et al., Enhancing Transcription through the *Echerichia coli* Hemolysin Operon, hlyCABD: RfaH and Upstream JUMPStart DNA Sequences Function Together via a Postinitiation Mechanism, Journal of Bacteriology, Jun. 1997, pp. 3519-3527.
Zakharova et al., Mutations in and Monoclonal Antibody Binding to Evolutionary Hypervariable Region of *Escherichia coli* RNA Polymerase B' Subunit Inhibit Transcript Cleavage and Transcript Elongation, Journal of Biological Chemistry, vol. 273, No. 38, pp. 24912-24920, 1998.

* cited by examiner

*Primary Examiner*—James Ketter

(57) ABSTRACT

Mutations in chromosomal genes have been identified that affect plasmid copy number in plasmids that are anti-sense RNA regulated such as the pMB1-derived and p15A-derived plasmids.

12 Claims, 8 Drawing Sheets

FIGURE 3
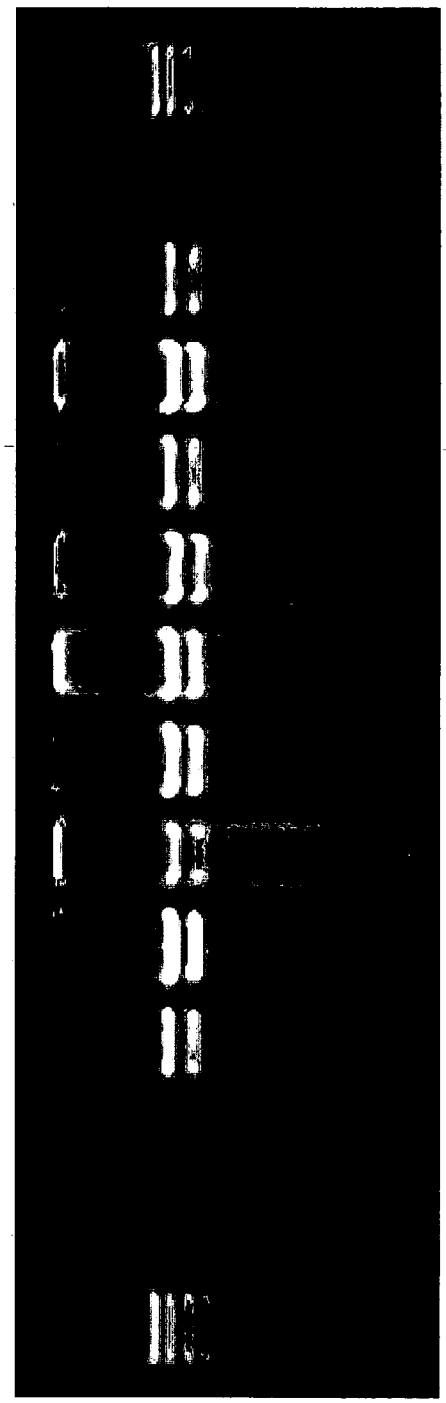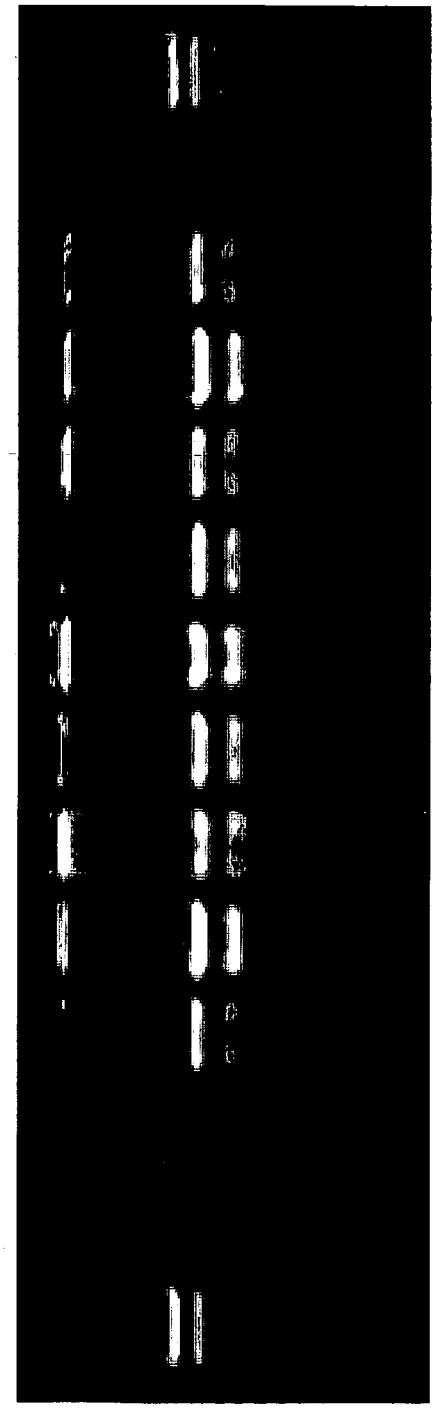

MUTATIONS AFFECTING PLASMID COPY NUMBER

This application claims the benefit of U.S. Provisional Application No. 60/434,973 filed Dec. 20, 2002.

FIELD OF THE INVENTION

This invention is in the field of microbiology. More specifically, this invention pertains regulating copy number of pBR and pACYC based plasmids.

BACKGROUND OF THE INVENTION

Molecular biotechnology is a discipline that is based on the ability of researchers to transfer specific units of genetic information from one organism to another. This process, known as cloning, relies on the techniques of recombinant DNA technology to produce a useful product or a commercial process (Glick, B. R.; Pasternak, J. J., *Molecular Biotechnology Principles and Applications of Recombinant DNA*, 2$^{nd}$ ed. American Society for Microbiology, Washington, D.C. 1998).

Commercial processes often require that proteins encoded by the cloned genes are produced at high rates of expression. There is no single strategy for achieving maximal expression of every cloned gene. Most cloned genes have distinctive molecular properties that require the investment of considerable time and effort before a specific set of conditions that result in an appropriate level of expression is found. There are a variety of ways to modulate gene expression. Microbial metabolic engineering generally involves the use of multicopy vectors to express a gene of interest under the control of a strong or conditional promoter. Increasing the copy number of cloned genes generally increases amounts and activity of encoded enzymes, therefore allowing increased levels of product formation that is important to commercial processes. However, it is sometimes difficult to maintain vectors in host cells due to instability. Deleterious effects on cell viability and growth can be observed due to the vector burden. The introduction and expression of foreign DNA in a host organism often changes the metabolism of the organism in ways that may impair normal cellular functioning. This phenomenon is due to a metabolic load or burden imposed upon the host by the foreign DNA. The metabolic load may result from a variety of conditions including: 1) increasing plasmid copy number, 2) overproduction of proteins, 3) saturation of export sites, and/or 4) interference of cellular function by the foreign protein itself. It is also difficult to control the optimal expression level of desired genes on a vector. Several reports have suggested altering the copy number of plasmids can have benefit in production of recombinant protein and analysis of transcriptional fusions (Grabherr et al., *Biotech. Bioeng.*, 77:142-147 (2002); Podkovyrov, S. M. and Larson, T. J., *Gene*, 156: 151-152 (1995)).

Bacterial plasmids are extrachromosomal genomes that replicate autonomously and in a controlled manner. Many plasmids are self-transmissible or mobilizable by other replicons, thus having the ability to colonize new bacterial species. In nature, plasmids may provide the host with valuable functions, such as drug resistance(s) or metabolic pathways useful under certain environmental conditions, although they are likely to constitute a slight metabolic burden to the host. To co-exist stably with their hosts and minimize the metabolic load, plasmids must control their replication, so that the copy number of a given plasmid is usually fixed within a given host and under defined cell growth conditions.

The number of copies of a plasmid can vary from 1, as in the case of the F plasmid, to over a hundred for pUC18. Bacterial plasmids maintain their number of copies by negative regulatory systems that adjust the rate of replication per plasmid copy in response to fluctuations in the copy number. Three general classes of regulatory mechanisms have been studied in depth, namely those that involve directly repeated sequences (iterons), those that use only antisense RNAs (AS-RNA), and those that use a mechanism involving an antisense RNA in combination with a protein.

Several chromosomal genes are known to affect the copy number of certain groups of plasmids. The pcnB gene encoding the poly(A) polymerase I has been found to affect copy number of ColE1 plasmids in *Escherichia coli*. Mutations in the pcnB locus of *E. coli* reduce the copy number of ColE1-like plasmids, which include pBR322-derived plasmids (Lopilato et al., *Mol. Gen. Genet.*, 205:285-290 (1986)) and pACYC-derived plasmids (Liu et al., *J. Bacteriol.*, 171:1254-1261 (1989)). Furthermore, it was discovered that the pcnB gene product was required for copy number maintenance of ColE1 and R1 plasmids of the IncFII compatibility group. Copy number of R1 plasmids like ColE1 is controlled by an antisense RNA mechanism, though the mechanism is different between the two. The iteron-regulated plasmids F and P1 were maintained normally in strains deleted for pcnB.

The gene relA encoding (p)ppGpp synthetase 1 allows cells to initiate stringent response during starvation. ColE1-type of plasmids can be amplified in amino acid-starved relA mutants of *Escherichia coli* (Wrobel et al., *Microbiol Res.*, 152:251-255 (1997)). Differential amplification efficiency of plasmids pBR328 (pMB1-derived replicon) and pACYC184 (p15A-derived replicon) was observed in the relA mutant during starvation for particular amino acids.

A recent paper described an origin-specific reduction of ColE1 plasmid copy number due to specific mutations in a distinct region of rpoC (Ederth et al., *Mol. Gen. Genomics*, 267:587-592 (2002)). The specific mutations, including a single amino acid substitution (G1161R) or a 41-amino acid deletion (Δ1149-1190), are located near the 3'-terminal region in the rpoC gene, encoding the largest subunit β' of the RNA polymerase. These mutations cause over 20- and 10-fold reductions, respectively, in is the copy number of ColE1. The RNA I/RNA II ratio, which controls the ColE1 plasmid copy number, was affected by these mutations.

The problem to be solved is to identify and provide chromosomal gene modifications that alter plasmid copy number in bacteria. The present invention has solved the stated problem through the discovery that disruptions in any one of 5 (thrS, rpsA, rpoC, yjeR, and rhoL) chromosomal genes will result in increase of copy number of certain plasmids. The effect of mutation of these loci on plasmids is novel and could not have been predicted from known studies.

SUMMARY OF THE INVENTION

The invention provides bacterial production host comprising:
  a) a plasmid comprising:
    (i) a target gene to be expressed; and
    (ii) a replicon controlled by antisense-RNA regulation; and b) a mutation in a gene selected from the group consisting of thrS, rpsA, rpoC, yjeR, and rhoL wherein the nucleotide sequence of the mutated thrS gene is SEQ ID NO:19; the nucleotide sequence of the mutated rpsA gene is SEQ ID NO:21; the nucleotide sequence of the mutated rpoC gene is SEQ ID NO:22; the nucleotide sequence of the mutated yjeR gene is SEQ ID NO:23; and the sequence of the mutated rhoL gene is SEQ ID NO:25.

In a preferred embodiment the invention provides a method for the expression of a target gene comprising:
a) providing an bacterial production host of the invention comprising a target gene to be expressed;
b) growing the production host of step (a) under suitable conditions wherein the target gene is expressed.

BRIEF DESCRIPTION OF THE DRAWINGS AND SEQUENCE DESCRIPTIONS

FIG. 3 is an image of a gel electrophoresis showing the amount of plasmid DNA isolated from the carotenoid-synthesizing plasmid pPCB15 isolated from wild type MG1655 and the mutants that affected carotenoid production.

Figure 4:
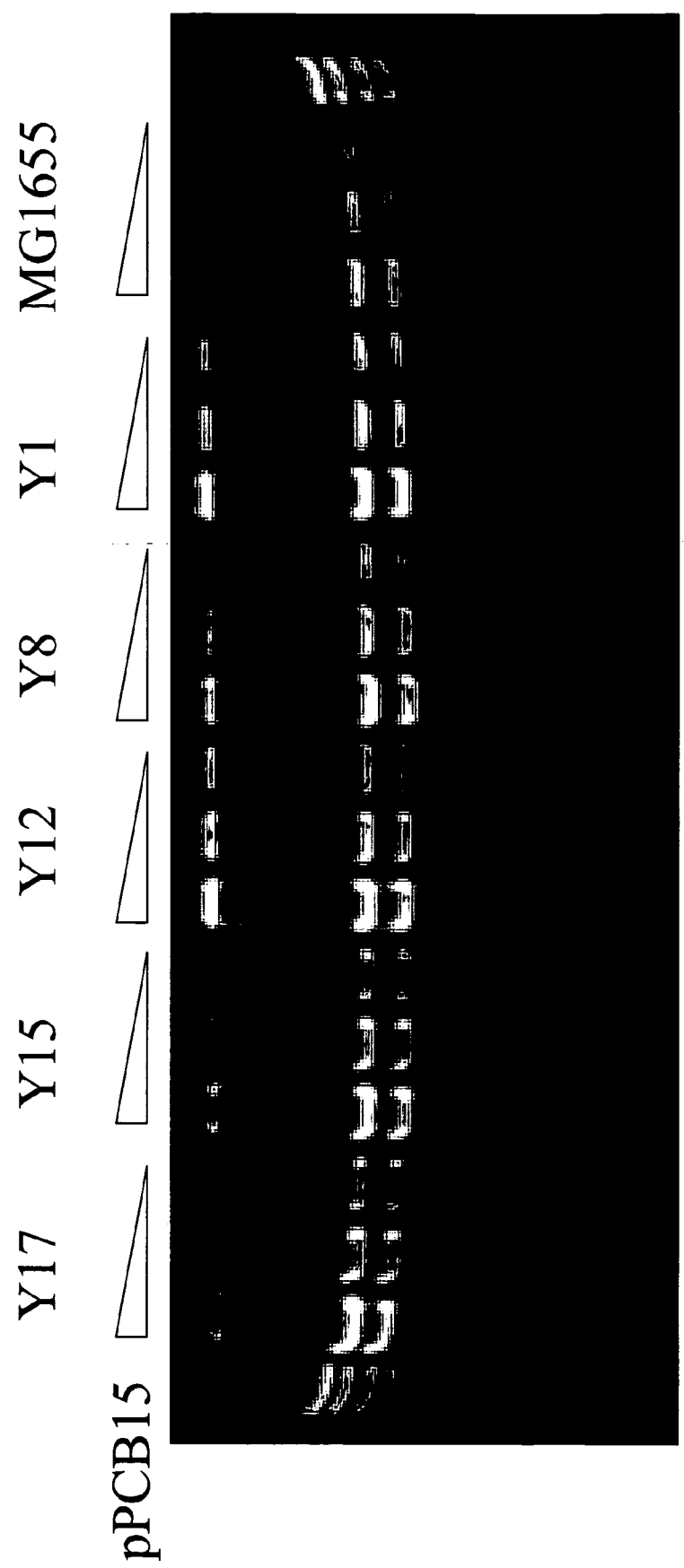

FIG. 4 an image of a gel electrophoresis showing levels of plasmid DNA extracted from mutants showing increased carotenoid production.

Figure 5:
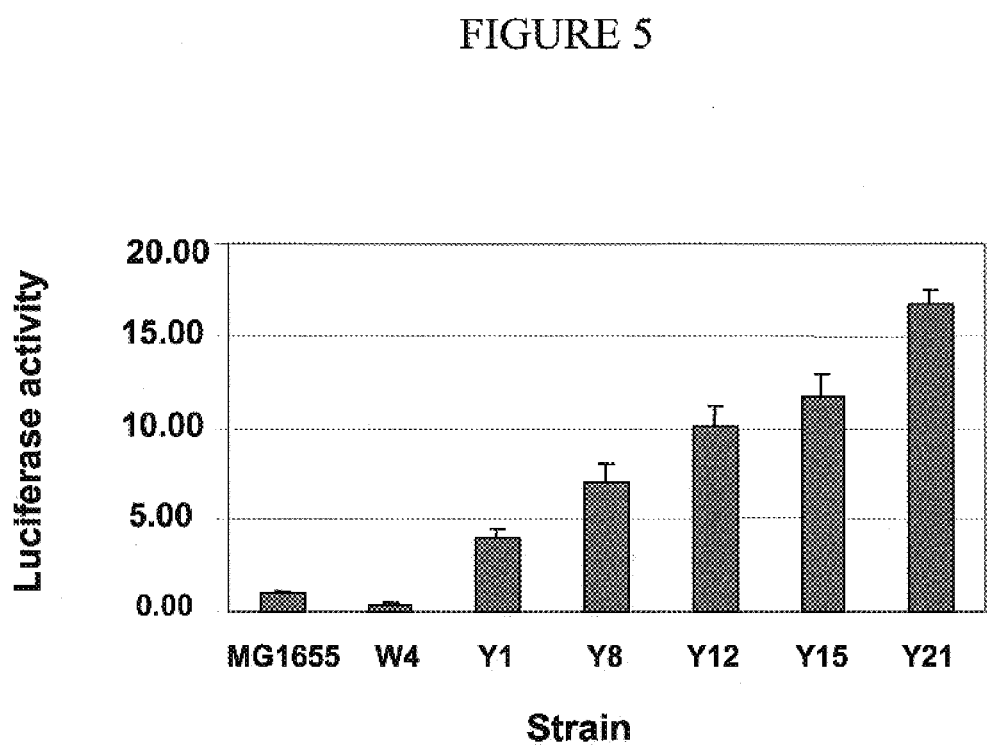

FIG. 5 shows the luciferase activity from the luxCDABE reporter plasmid pTV200 in MG1655 and the mutants.

Figure 6:
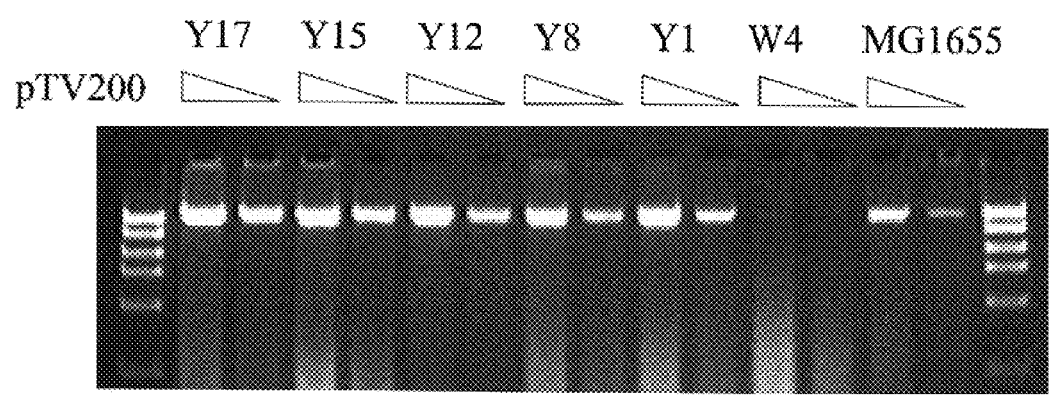

FIG. 6 is a gel comparing the isolated plasmid DNA of pTV200 as compared with wild type MG1655 and related mutants.

Figure 7:
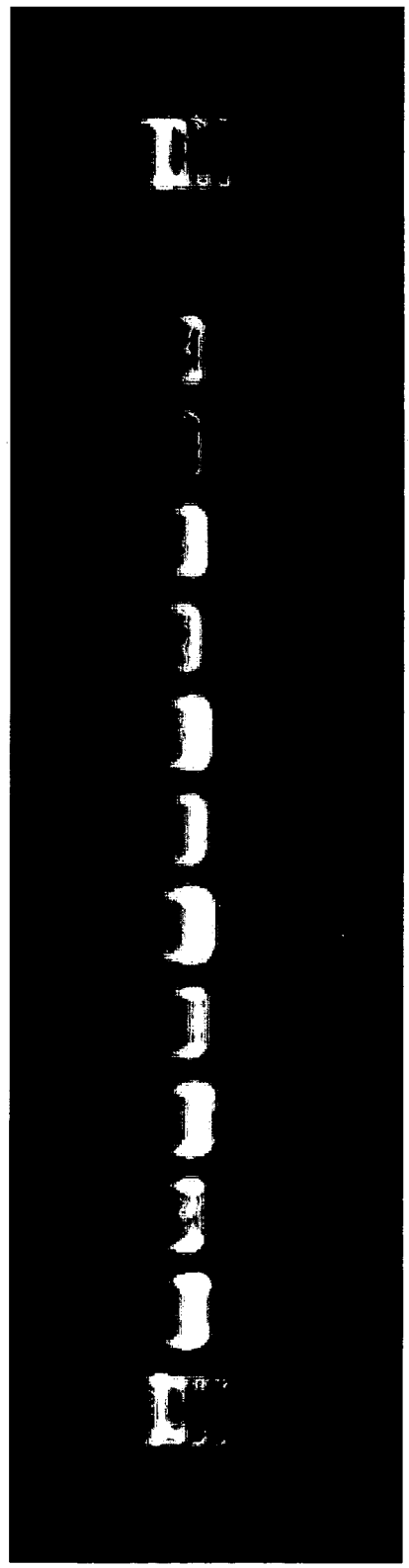

FIG. 7 is a gel comparing the isolated plasmid DNA of pBR328 with that from wild type MG1655 and related mutants.

Figure 8:
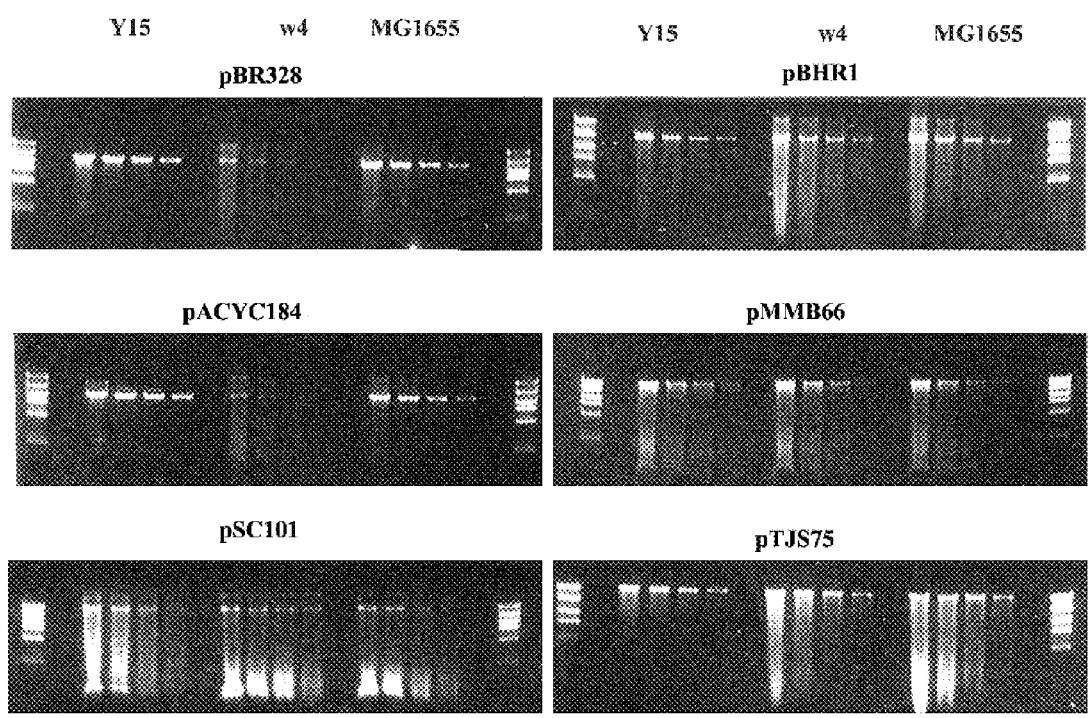

FIG. 8 is a gel showing plasmids DNA from different replicons in MG1655 and the W4 and Y15 mutants.

The invention can be more fully understood from the following detailed description and the accompanying sequence descriptions, which form a part of this application.

The following sequences comply with 37 C.F.R. 1.821-1.825 ("Requirements for Patent Applications Containing Nucleotide Sequences and/or Amino Acid Sequence Disclosures—the Sequence Rules") and are consistent with World Intellectual Property Organization (WIPO) Standard ST.25 (1998) and the sequence listing requirements of the EPO and PCT (Rules 5.2 and 49.5(a-bis), and Section 208 and Annex C of the Administrative Instructions). The symbols and format used for nucleotide and amino acid sequence data comply with the rules set forth in 37 C.F.R. §1.822.

TABLE 1

Nucleotide and amino acid sequences for Pantoea stewartii carotenoid biosynthesis genes.

| Gene/Protein Product | Source | Nucleotide SEQ ID NO | Amino Acid SEQ ID NO |
|---|---|---|---|
| CrtE | Pantoea stewartii | 1 | 2 |
| CrtX | Pantoea stewartii | 3 | 4 |
| CrtY | Pantoea stewartii | 5 | 6 |
| CrtI | Pantoea stewartii | 7 | 8 |

TABLE 1-continued

Nucleotide and amino acid sequences for Pantoea stewartii carotenoid biosynthesis genes.

| Gene/Protein Product | Source | Nucleotide SEQ ID NO | Amino Acid SEQ ID NO |
|---|---|---|---|
| CrtB | Pantoea stewartii | 9 | 10 |
| CrtZ | Pantoea stewartii | 11 | 12 |

SEQ ID NOs:13-14 are oligonucleotide primers used to amplify the carotenoid biosynthetic genes from P. stewartii.

SEQ ID NOs:15-18 are oligonucleotide primers used to screen for the Tn5 insertion site in mutants of the present invention.

SEQ ID NO: 19 is the nucleotide sequence of the mutated thrS gene with the Tn5 insertion.

SEQ ID NO: 20 is the nucleotide sequence of the mutated deaD gene with the Tn5 insertion.

SEQ ID NO: 21 is the nucleotide sequence of the mutated rpsA gene with the Tn5 insertion.

SEQ ID NO: 22 is the nucleotide sequence of the mutated rpoC gene with the Tn5 insertion.

SEQ ID NO: 23 is the nucleotide sequence of the mutated yjeR gene with the Tn5 insertion.

SEQ ID NO: 24 is the nucleotide sequence of the mutated mreC gene with the Tn5 insertion.

SEQ ID NO: 25 is the nucleotide sequence of the mutated rhoL gene with the Tn5 insertion.

SEQ ID NO: 26 is the nucleotide sequence of the mutated hscB (yfhE) gene with the Tn5 insertion.

SEQ ID NO: 27 is the nucleotide sequence of the mutated pcnB gene with the Tn5 insertion.

SEQ ID NO: 28 is the nucleotide sequence for the plasmid pPCB15.

DETAILED DESCRIPTION OF THE INVENTION

The invention relates to a method for regulating plasmid copy number for plasmids exhibiting anti-sense RNA copy-number control including those under the control of the pMB1 and p15A replicons. Specifically, it has been discovered that mutations in the chromosomal genes thrS, rpsA, rpoC, yjeR, and rhoL have an effect on plasmid copy number of these plasmids.

The ability to regulate the copy number of plasmids has implications for the production of many microbially produced industrial chemicals and pharmaceuticals where additional copies of key pathway genes will enhance pathway performance.

In this disclosure, a number of terms and abbreviations are used. The following definitions are provided.

"Open reading frame" is abbreviated ORF.

"Polymerase chain reaction" is abbreviated PCR.

The term "p15A" refers to a replicon for a family of plasmid vectors including pACYC-based vectors.

The term "pMB1" refers to a replicon for a family of plasmid vectors including pUC and pBR based vectors The term "replicon" refers to a genetic element that behaves as an autonomous unit during replication. It contains sequences controlling replication of a plasmid including its origin of replication.

The term "ColE1" refers to a replicon for a family of plasmid vectors including p15A and pMB1.

The term "pACYC derived plasmids" refers to a family of plasmids derived from the p15A origin.

The term "(p)ppGpp synthetase 1" refers to the enzyme coded for by the relA gene. (p)ppGpp refers to both guanosine tetraphosphate (ppGpp) and guanosine pentaphosphate (p)ppGpp, unusual nucleotides involved in the stringent response.

The term "stringent response" refers to the cellular response to lack of amino acids necessary for protein synthesis.

The term "iterons" refers to directly repeating DNA sequences located either within or slightly outside of the origin of replication of a plasmid to which regulatory proteins bind to in order to initiate and regulate replication.

The term "RNA I" refers to a 108 nucleotide molecule of RNA, complementary to the 5' end of RNA II, that is a negative regulator of replication of many plasmid origins.

The term "RNA II" refers to an RNA transcript made by RNA polymerase that allows for the initiation of replication of a plasmid.

The terms "anti-sense RNA copy-control" and "AS-RNA" refer to one of the methods by which plasmid copy number is controlled.

The term "production host" means a bacteria engineered to produce a specific genetic end product. The term "enteric production host" means an enteric bacteria engineered to produce a specific genetic end product. Typical examples of enteric bacteria are the genera *Escherichia* and *Salmonella*.

The term "isoprenoid" or "terpenoid" refers to the compounds and any molecules derived from the isoprenoid pathway including 10 carbon terpenoids and their derivatives, such as carotenoids and xanthophylls.

The "Isoprenoid Pathway" as used herein refers to the enzymatic pathway that is responsible for the production of isoprenoids. At a minimum, the isoprenoid pathway contains the genes dxs, dxr, ygpP(ispD), ychB(ispE), ygbB(ispF), lytB, idi, ispA, and ispB which may also be referred to herein as the "Upper Isoprenoid Pathway". The "Carotenoid Biosynthetic Pathway", "Lower Isoprenoid Pathway" or "Lower Pathway" refers to the genes encoding enzymes necessary for the production of carotenoid compounds and include, but are not limited to crtE, crtB, crtI, crtY, crtX, and crtZ.

The term "carotenoid biosynthetic enzyme" is an inclusive term referring to any and all of the enzymes encoded by the Pantoea crtEXYIB cluster. The enzymes include CrtE, CrtY, CrtI, CrtB, and CrtX.

The term "pPCB15" refers to the pACYC-derived plasmid containing β-carotene synthesis genes Pantoea crtEXYIB, used as a reporter plasmid for monitoring β-carotene production in *E. coli*.

The term "*E. coli*" refers to *Escherichia coli* strain K-12 derivatives, such as MG1655 (ATCC 47076) and MC1061 (ATCC 53338).

The term "*Pantoea stewartii*" used interchangeably with *Erwinia stewartii* (Mergaert et al., *Int J. Syst. Bacteriol.*, 43:162-173 (1993)).

The term "*Pantoea ananatas*" is used interchangeably with *Erwinia uredovora* (Mergaert et al., supra).

The term "*Pantoea* crtEXYIB cluster" refers to a gene cluster containing carotenoid synthesis genes crtEXYIB amplified from *Pantoea stewartii* ATCC 8199. The gene cluster contains the genes crtE, crtX, crtY, crtI, and crtB. The cluster also contains a crtZ gene organized in opposite direction adjacent to crtB gene.

The term "CrtE" refers to the geranylgeranyl pyrophosphate synthase enzyme encoded by crtE gene which converts trans-trans-farnesyl diphosphate+isopentenyl diphosphate to pyrophosphate+geranylgeranyl diphosphate.

The term "CrtY" refers to the lycopene cyclase enzyme encoded by crtY gene which converts lycopene to β-carotene.

The term "CrtI" refers to the phytoene dehydrogenase enzyme encoded by crtI gene which converts phytoene into lycopene via the intermediaries of phytofluene, zeta-carotene, and neurosporene by the introduction of 4 double bonds.

The term "CrtB" refers to the phytoene synthase enzyme encoded by crtB gene which catalyzes reaction from prephytoene diphosphate (geranylgeranyl pyrophosphate) to phytoene.

The term "CrtX" refers to the zeaxanthin glucosyl transferase enzyme encoded by crtX gene which converts zeaxanthin to zeaxanthin-β-diglucoside.

The term "CrtZ" refers to the β-carotene hydroxylase enzyme encoded by the crtZ gene which catalyses hydroxylation reaction from β-carotene to zeaxanthin.

The term "pTV200" refers to the plasmid based upon the pACYC184 plasmid that contains a promoterless luxCD-ABE gene cassette from *Photorabdus luminescens* and produces luminescence or light when transformed into *E. coli*.

The term "pBR328" refers to one of the pBR plasmids derived from the pMB1 replicon.

The term "pACAY184" refers to one of the pACYC plasmids derived from the p15A replicon.

The term "pSC101" refers to the representative plasmid belonging to the pSC101 replicon group.

The term "pBHR1" refers to the plasmid derived from the pBBR1 replicon with a broad host range origin of replication.

The term "pMMB66" refers to the plasmid derived from RSF1010 that belongs to the IncQ incompatibility group.

The term "pTJS75" refers to the plasmid derived from RK2 that belongs to the IncP incompatibility group.

The term "pcnB" refers to the poly(A) polymerase gene locus.

The term "thrS" refers to the threonyl-tRNA synthetase gene locus.

The term "deaD" refers to the RNA helicase gene locus.

The term "rpsA" refers to the 30S ribosomal subunit protein S1 gene locus.

The term "rpoC" refers to the RNA polymerase β' subunit gene locus.

The term "yjeR" refers to the oligoribonuclease gene locus.

The term "mreC" refers to the rod-shape determining protein gene locus.

The term "rhoL" refers to the rho operon leader peptide gene locus.

The terms "yfhE" or "hscB" refer to the heat-shock-cognate-protein gene locus.

The term "incompatibility group" refers to plasmids that cannot co-exist in a bacterial host. Generally, plasmids within the same incompatibility group have similar mechanisms of replication and replication control.

The term "Rep" refers to the replication proteins that initiate plasmid replication. Many Rep proteins also regulate the frequency of initiation.

The term "Rop" refers to a small protein which when it binds to both RNA molecules, increases the stability of the RNA I/RNA II complex, thus decreasing the likelihood of plasmid replication.

The term "CopG" refers to a transcriptional repressor protein of plasmid replication.

The term "RNAP" refers to RNA polymerase.

As used herein, an "isolated nucleic acid fragment" is a polymer of RNA or DNA that is single- or double-stranded, optionally containing synthetic, non-natural or altered nucleotide bases. An isolated nucleic acid fragment in the form of a polymer of DNA may be comprised of one or more segments of cDNA, genomic DNA or synthetic DNA.

The term "genetic end product" means the substance, chemical or material that is produced as the result of the activity of a gene product. Typically a gene product is an enzyme and a genetic end product is the product of that enzymatic activity on a specific substrate. A genetic end product may the result of a single enzyme activity or the result of a number of linked activities, such as found in a biosynthetic pathway (several enzyme activites).

The term "complementary" is used to describe the relationship between nucleotide bases that are capable to hybridizing to one another. For example, with respect to DNA, adenosine is complementary to thymine and cytosine is complementary to guanine.

"Codon degeneracy" refers to the nature in the genetic code permitting variation of the nucleotide sequence without effecting the amino acid sequence of an encoded polypeptide. The skilled artisan is well aware of the "codon-bias" exhibited by a specific host cell in usage of nucleotide codons to specify a given amino acid. Therefore, when synthesizing a gene for improved expression in a host cell, it is desirable to design the gene such that its frequency of codon usage approaches the frequency of preferred codon usage of the host cell.

"Synthetic genes" can be assembled from oligonucleotide building blocks that are chemically synthesized using procedures known to those skilled in the art. These building blocks are ligated and annealed to form gene segments that are then enzymatically assembled to construct the entire gene. "Chemically synthesized", as related to a sequence of DNA, means that the component nucleotides were assembled in vitro. Manual chemical synthesis of DNA may be accomplished using well-established procedures, or automated chemical synthesis can be performed using one of a number of commercially available machines. Accordingly, the genes can be tailored for optimal gene expression based on optimization of nucleotide sequence to reflect the codon bias of the host cell. The skilled artisan appreciates the likelihood of successful gene expression if codon usage is biased towards those codons favored by the host. Determination of preferred codons can be based on a survey of genes derived from the host cell where sequence information is available.

"Gene" refers to a nucleic acid fragment that expresses a specific protein, including regulatory sequences preceding (5' non-coding sequences) and following (3' non-coding sequences) the coding sequence. "Native gene" refers to a gene as found in nature with its own regulatory sequences. "Chimeric gene" refers to any gene that is not a native gene, comprising regulatory and coding sequences that are not found together in nature. Accordingly, a chimeric gene may comprise regulatory sequences and coding sequences that are derived from different sources, or regulatory sequences and coding sequences derived from the same source, but arranged in a manner different than that found in nature. "Endogenous gene" refers to a native gene in its natural location in the genome of an organism. A "foreign" or "exogenous" gene refers to a gene not normally found in the host organism, but that is introduced into the host organism by gene transfer. Foreign genes can comprise native genes inserted into a non-native organism, or chimeric genes. A "transgene" is a gene that has been introduced into the genome by a transformation procedure. "Disrupted gene" refers to a gene fragment disrupted by an insertion of a foreign DNA such as a transposon. Disruption in the 5' end or the middle of the gene likely abolishes the function of the gene. Disruption close to the 3' terminal end of the gene might result in altered function from the truncated protein. "Target gene" is the gene of interest that is used in the synthesis of a desired genetic end product, usually resulting in a measurable phenotypic change in the microorganism.

"Operon", in bacterial DNA, is a cluster of contiguous genes transcribed from one promoter that gives rise to a polycistronic mRNA.

"Coding sequence" refers to a DNA sequence that codes for a specific amino acid sequence. "Suitable regulatory sequences" refer to nucleotide sequences located upstream (5' non-coding sequences), within, or downstream (3' non-coding sequences) of a coding sequence, and which influence the transcription, RNA processing or stability, or translation of the associated coding sequence. Regulatory sequences may include promoters, translation leader sequences, introns, polyadenylation recognition sequences, RNA processing site, effector binding site and stem-loop structure.

"Promoter" refers to a DNA sequence capable of controlling the expression of a coding sequence or functional RNA. In general, a coding sequence is located 3' to a promoter sequence. Promoters may be derived in their entirety from a native gene, or be composed of different elements derived from different promoters found in nature, or even comprise synthetic DNA segments. It is understood by those skilled in the art that different promoters may direct the expression of a gene in different tissues or cell types, or at different stages of development, or in response to different environmental or physiological conditions ("inducible promoters"). Promoters which cause a gene to be expressed in most cell types at most times are commonly referred to as "constitutive promoters". Promoters can be further classified by the relative strength of expression observed by their use (i.e. weak, moderate, or strong). It is further recognized that since in most cases the exact boundaries of regulatory sequences have not been completely defined, DNA fragments of different lengths may have identical promoter activity.

The "3' non-coding sequences" refer to DNA sequences located downstream of a coding sequence capable of affecting mRNA processing or gene expression.

"RNA transcript" refers to the product resulting from RNA polymerase-catalyzed transcription of a DNA sequence. When the RNA transcript is a perfect complementary copy of the DNA sequence, it is referred to as the primary transcript or it may be a RNA sequence derived from post-transcriptional processing of the primary transcript and is referred to as the mature RNA. "Messenger RNA (mRNA)" refers to the RNA that is without introns and that can be translated into protein by the cell. "cDNA" refers to a double-stranded DNA that is complementary to and derived from mRNA. "Sense" RNA refers to RNA transcript that includes the mRNA and so can be translated into protein by the cell. "Antisense RNA" refers to a RNA transcript that is complementary to all or part of a target primary transcript or mRNA and that blocks the expression of a target gene (U.S. Pat. No. 5,107,065; WO 99/28508). The complementarity of an antisense RNA may be with any part of the specific gene transcript, i.e., at the 5' non-coding sequence, 3' non-coding sequence, or the coding sequence. "Functional RNA" refers to antisense RNA, ribozyme RNA, or other RNA that is not translated yet has an effect on cellular processes.

The term "operably linked" refers to the association of nucleic acid sequences on a single nucleic acid fragment so that the function of one is affected by the other. For example, a promoter is operably linked with a coding sequence when it is capable of affecting the expression of that coding sequence (i.e., that the coding sequence is under the transcriptional control of the promoter). Coding sequences can be operably linked to regulatory sequences in sense or antisense orientation.

The term "expression", as used herein, refers to the transcription and stable accumulation of sense (mRNA) or antisense RNA derived from the nucleic acid fragment of the invention. Expression may also refer to translation of mRNA into a polypeptide.

"Transformation" refers to the transfer of a nucleic acid fragment into the genome of a host organism, resulting in genetically stable inheritance. Host organisms containing the transformed nucleic acid fragments are referred to as "transgenic", "recombinant" or "transformed" organisms.

The terms "plasmid", "vector" and "cassette" refer to an extrachromosomal element often carrying genes which are not part of the central metabolism of the cell, and usually in the form of circular double-stranded DNA fragments. Such elements may be autonomously replicating sequences, genome integrating sequences, phage or nucleotide sequences, linear or circular, of a single- or double-stranded DNA or RNA, derived from any source, in which a number of nucleotide sequences have been joined or recombined into a unique construction which is capable of introducing a promoter fragment and DNA sequence for a selected gene product along with appropriate 3' untranslated sequence into a cell. "Transformation cassette" refers to a specific vector containing a foreign gene and having elements in addition to the foreign gene that facilitate transformation of a particular host cell. "Expression cassette" refers to a specific vector containing a foreign gene and having elements in addition to the foreign gene that allow for enhanced expression of that gene in a foreign host.

The term "sequence analysis software" refers to any computer algorithm or software program that is useful for the analysis of nucleotide or amino acid sequences. "Sequence analysis software" may be commercially available or independently developed. Typical sequence analysis software will include but is not limited to the GCG suite of programs (Wisconsin Package Version 9.0, Genetics Computer Group (GCG), Madison, Wis.), BLASTP, BLASTN, BLASTX (Altschul et al., *J. Mol. Biol.* 215:403-410 (1990), and DNASTAR (DNASTAR, Inc. 1228 S. Park St. Madison, Wis. 53715 USA), and the FASTA program incorporating the Smith-Waterman algorithm (W. R. Pearson, *Comput. Methods Genome Res.*, [Proc. Int. Symp.] (1994), Meeting Date 1992, 111-20. Editor(s): Suhai, Sandor. Publisher: Plenum, New York, N.Y. Within the context of this application it will be understood that where sequence analysis software is used for analysis, that the results of the analysis will be based on the "default values" of the program referenced, unless otherwise specified. As used herein "default values" will mean any set of values or parameters which originally load with the software when first initialized.

The present invention relates to microorganisms having increased plasmid copy number. Typically the plasmids will be those that are anti-sense RNA regulated including the following replicons: p15A and pMB1. Specifically, it has been discovered that mutations in five chromosomal genes, including thrS, rpsA, rpoC, yjeR, and rhoL resulted in the alteration of these classes of plasmids.

Plasmids

Plasmids are autonomous, self-replicating, extra-chromosomal elements generally not required for growth. Many of the genes on the plasmid allow for bacterial survival in a wide variety of challenging environments. Plasmids code for the proteins needed to initiate their replication. However, they do rely on the host cell replication machinery for replication. A "replicon" is any genetic element (e.g., plasmid, phage, cosmid, chromosome, virus) that functions as an autonomous unit of DNA replication in vivo. A replicon comprises an origin of replication, to which another DNA segment may be attached so as to bring about the replication of the attached segment. Plasmids useful for gene expression are ubiquitous and well known in the art. Plasmids can be categorized based on several characteristics including copy number (single, low, medium, and high), method for regulation of copy number (iterons, AS-RNA, AS-RNA+repressor protein), method of replication (theta replication, strand displacement replication, rolling-circle replication) and incompatibility group. Plasmids derived from the same replicon replicate by the same mechanism and belong to the same incompatibility group.

Replication and control of circular bacterial plasmids is summarized in a review (del Solar et al., *Microbiol. And Mol. Boil. Rev.*, 62:434-464, (1998)). The first mechanism of plasmid copy number control is by iterons. The origin of replication for this class of plasmids, such as R6K, contain iterons. Iterons are directly repeated sequences necessary for replication and replication control. The iteron sites allow for the binding of the replication proteins that control plasmid replication. The second mechanism for copy control is by anti-sense RNA (AS-RNA). This is the mechanism by which ColE1 plasmids like p15A and pMB1 replicons are regulated. Briefly, inhibition of replication of these plasmids involves the interaction of RNA II, a post-transcriptionally processed transcript made by RNAP and RNA I, a 108-nucleotide anti-sense RNA complementary to the 5' end of RNA II. RNA I binds to RNA II and prevents its folding into a cloverleaf structure that is necessary for the formation of a stable RNA II/plasmid DNA hybrid for DNA synthesis. Rop is a small protein which when it binds to both RNA molecules, increases the stability of the RNA I/RNA II complex, thus decreasing the likelihood of replication. The final method of copy control of plasmids, like R1, also involves AS-RNA. However, in these cases a transcriptional repressor, like CopG, interacts directly with the AS-RNA, RNA II. CopG binds to and represses transcription of both the copG and repB genes. RNA II is a small RNA complementary to a region of the cop-rep mRNA. When the proteins have complexed with both the RNA and the AS-RNA then replication can not occur.

Target Genes

Plasmids can be used to express any endogenous or exogenous gene of interest for production of any desired genetic end product. Target genes may be drawn from a wide variety of biochemically important compounds including the pathways responsible for the synthesis of isoprenoids, carotenoids, terpenoids, tetrapyrroles, polyketides, vitamins, amino acids, fatty acids, proteins, nucleic acids, carbohydrates, antimicrobial agents, anticancer agents, poly-hydroxyalkanoic acid synthases, nitrilases, nitrile hydratases, amidases, enzymes used in the production of synthetic silk proteins, pyruvate decarboxylases, alcohol dehydrogenases, and biological metabolites.

For example suitable target genes will include, but are not limited to genes used in the production of poly-hydroxyalkanoic acid (PHA) synthases (phaC) which can be expressed for the production of biodegradable plastics, genes encoding nitrile hydratases for production of acrylamide, genes encoding synthetic silk protein genes for the production of silk proteins, the pyruvate decarboxylase gene (pdc), the alcohol dehydrogenase gene (adh) for alcohol production, genes encoding terpene synthases from plants for production of terpenes, genes encoding cholesterol oxidases for production of the enzyme,genes encoding monooxygenases derived from waste stream bacteria, the upstream isoprenoid pathways genes such as dxs, dxr, ispA, ispD, ispE, ispF, lytB, and gcpE to increase the flux of the isoprenoid pathway, the carotenoid synthesis and functionalization genes such as crtE, crtB, crtI, crtY, crtW, crtO, and crtZ to increase carotenoid production, genes used in tetrapyrrole biosynthesis, genes used in the production of polyketides, genes used in the synthesis of vitamins, genes used in the synthesis of fatty acids, genes used in the synthesis of carbohydrates, genes used in the production of antimicrobial agents, genes used in the synthesis of anti-canter agents, genes used in the synthesis of proteins and amino acids, genes used in the synthesis of nucleic acid, and genes used in the synthesis of biological metabolites. The preferred target genes used in the present invention are the crtEXYIB gene cluster from *Pantoea stewartii* ATCC 8199 (SEQ ID NOs. 1, 3, 5, 7, 9, and 11).

Optionally, one may produce the genetic end product as a secretion product of the transformed host. Secretion of desired proteins into the growth media has the advantages of simplified and less costly purification procedures. It is well known in the art that secretion signal sequences are often useful in facilitating the active transport of expressible proteins across cell membranes. The creation of a transformed host capable of secretion may be accomplished by the incorporation of a DNA sequence that codes for a secretion signal which is functional in the host production host. Methods for choosing appropriate signal sequences are well known in the art (EP 546049; WO 93/24631). The secretion signal DNA or facilitator may be located between the expression-controlling DNA and the instant gene or gene fragment, and in the same reading frame with the latter.

The plasmids or vectors may further comprise at least one promoter suitable for driving expression of genes in microbial hosts that will support the replication of the plasmids. Typically these promoters, including the initiation control regions, will be derived from native sources so that they function well in the preferred hosts. Termination control regions may also be derived from various genes native to the preferred hosts. Optionally, a termination site may be unnecessary, however, it is most preferred if included.

Carotenoid Biosynthesis

Carotenoids are pigments that are ubiquitous throughout nature and synthesized by all oxygen evolving photosynthetic organisms, and in some heterotrophic growing bacteria and fungi. Industrial uses of carotenoids include pharmaceuticals, food supplements, electro-optic applications, animal feed additives, and colorants in cosmetics, to mention a few. Because animals are unable to synthesize carotenoids de novo, they must obtain them by dietary means. Thus, manipulation of carotenoid production and composition in plants or bacteria can provide new or improved sources of carotenoids.

The genetics of carotenoid pigment biosynthesis are well known (Armstrong et al., *J. Bact.*, 176: 4795-4802 (1994); *Annu. Rev. Microbiol.* 51:629-659 (1997)). This pathway is extremely well studied in the Gram-negative, pigmented bacteria of the genera *Pantoea*, formerly known as *Erwinia*. In both *E. herbicola* EHO-10 (ATCC 39368) and *E. uredovora* 20D3 (ATCC 19321), the crt genes are clustered in two operons, crt Z and crt EXYIB (U.S. Pat. No. 5,656,472; U.S. Pat. No. 5,545,816; U.S. Pat. No. 5,530,189; U.S. Pat. No. 5,530,188; and U.S. Pat. No. 5,429,939). Despite the similarity in operon structure, the DNA sequences of *E. uredovora* and *E. herbicola* crt genes show no homology by DNA-DNA hybridization (U.S. Pat. No. 5,429,939). The *Pantoea stewartii* crt genes have been described previously (U.S. Ser. No. 10/218118; WO 02/079395).

Carotenoids come in many different forms and chemical structures. Most naturally occurring carotenoids are hydrophobic tetraterpenoids containing a $C_{40}$ methyl-branched hydrocarbon backbone derived from successive condensation of eight $C_5$ isoprene units (isopentenyl diphosphate, IPP). In addition, novel carotenoids with longer or shorter backbones occur in some species of nonphotosynthetic bacteria.

*E. coli* contain the biosynthetic pathway necessary to synthesize farnesyl pyrophosphate (FPP) from IPP. FPP synthesis is common in both carotenogenic and non-carotenogenic bacteria. *E.coli* do not normally contain the genes necessary for conversion of FPP to β-carotene. Because of this, an *E. coli* strain containing a reporter plasmid (pPCB15) was used which has the additional genes necessary for β-carotene production in *E. coli* (FIG. 1; SEQ ID NO: 28). Enzymes in the subsequent carotenoid pathway used to generate carotenoid pigments from FPP precursor can be divided into two categories: carotene backbone synthesis enzymes and subsequent modification enzymes. The backbone synthesis enzymes include geranyl geranyl pyrophosphate synthase (CrtE), phytoene synthase (CrtB), phytoene dehydrogenase (CrtI) and lycopene cyclase (CrtY/L), etc. The modification enzymes include ketolases, hydroxylases, dehydratases, glycosylases, etc.

Engineering *E. coli* for increased carotenoid production has previously focused on overexpression of key isoprenoid pathway genes from multi-copy plasmids. Various studies have report between a 1.5× and 50× increase in carotenoid formation in such *E. coli* systems upon cloning and transformation of plasmids encoding isopentenyl diphosphate isomerase (idi), geranylgeranyl pyrophosphate (GGPP) synthase (gps), deoxy-D-xylulose-5-phosphate (DXP) synthase (dxs), DXP reductoisomerase (dxr) from various sources (Kim, S.-W., and Keasling, J. D., *Biotech. Bioeng.*, 72:408-415 (2001); Mathews, P. D., and Wurtzel, E. T., *Appl. Microbiol. Biotechnol.*, 53:396-400 (2000); Harker, M, and Bramley, P. M., *FEBS Letter.*, 448:115-119 (1999); Misawa, N., and Shimada, H., *J. Biotechnol.*, 59:169-181 (1998); Liao et al., *Biotechnol. Bioeng.*, 62:235-241 (1999); and Misawa et al., *Biochem. J.*, 324:421-426 (1997)). In the present invention, the lower-carotenoid pathway genes crtEXYIB, rather the upper isoprenoid genes, were expressed on the multicopy plasmid. The chromosomal mutations described in the present invention increase the copy number of the plasmids, thus increasing carotenoid production.

Mutations

Mutations isolated in this invention were all transposon insertions near the 3' end of essential genes, which likely resulted in altered gene function. These genes are involved in transcription and translation. Homologs of these genes are present in other organisms. Mutations of these homologs would be expected to have the same effect on these plasmids as mutations in E. coli genes.

The structural gene for threonyl-tRNA synthetase is thrS. It is one of the tRNA synthetases that bring together the specific amino acid it codes for and its tRNA molecule specific for that amino acid. It is an essential gene involved in protein synthesis. In the present invention, mutant Y1 contains a transposon disrupted thrS gene (SEQ ID NO.19).

Ribosomal protein S1 is encoded by the rpsA gene. This protein facilitates the binding between the mRNA molecule and the ribosome. Ribosomes deficient in protein S1 are unable to extend the elongating peptide and are lethal to E. coli. However, one study demonstrated that a mutant lacking the 120 amino acids at the COOH-terminal region of the protein does not have significantly altered activity. Mutant Y8 contains a transposon disrupted rpsA gene (SEQ ID NO. 21).

The β' subunit of the RNA polymerase is encoded by the rpoC gene. It is an essential gene involved in transcription. Mutations near the 3' end of the gene were isolated and had a pleiotropic effect. A specific point mutation or a 3' end deletion of rpoC resulted in substantial reductions of the copy number of a ColE1 plasmid. (Ederth et al., Mol Genet Genomics, 267 (5): 587-592 (2002)). The rpoC 3' mutation by transposon insertion isolated in this invention had the opposite effect, increasing the copy number of the ColE1 plasmids. Mutant Y12 contains a transposon disrupted rpoC gene (SEQ ID NO. 23).

The gene yjeR (renamed orn) codes for an oligoribonuclease with a specificity for small oligoribonucleotides. Studies by Ghosh and Deutscher (PNAS, 96: 4372-4377 (1999)) indicate that the yjeR gene product is responsible for degrading small mRNA molecules to mononucleotides, a process necessary for cell viability. Mutant Y15 contains a transposon disrupted yjeR gene (SEQ ID NO. 24).

The leader peptide of the rho operon is encoded by the rhoL gene. The protein factor rho is responsible for terminating transcription at specific sites of the RNA. In genes relying on this small protein for transcription termination, rho binds to the RNA causing the RNA polymerase to fall off of the DNA. Mutant Y17 contains a transposon disrupted rhoL gene (SEQ ID NO. 25).

Figure 1:
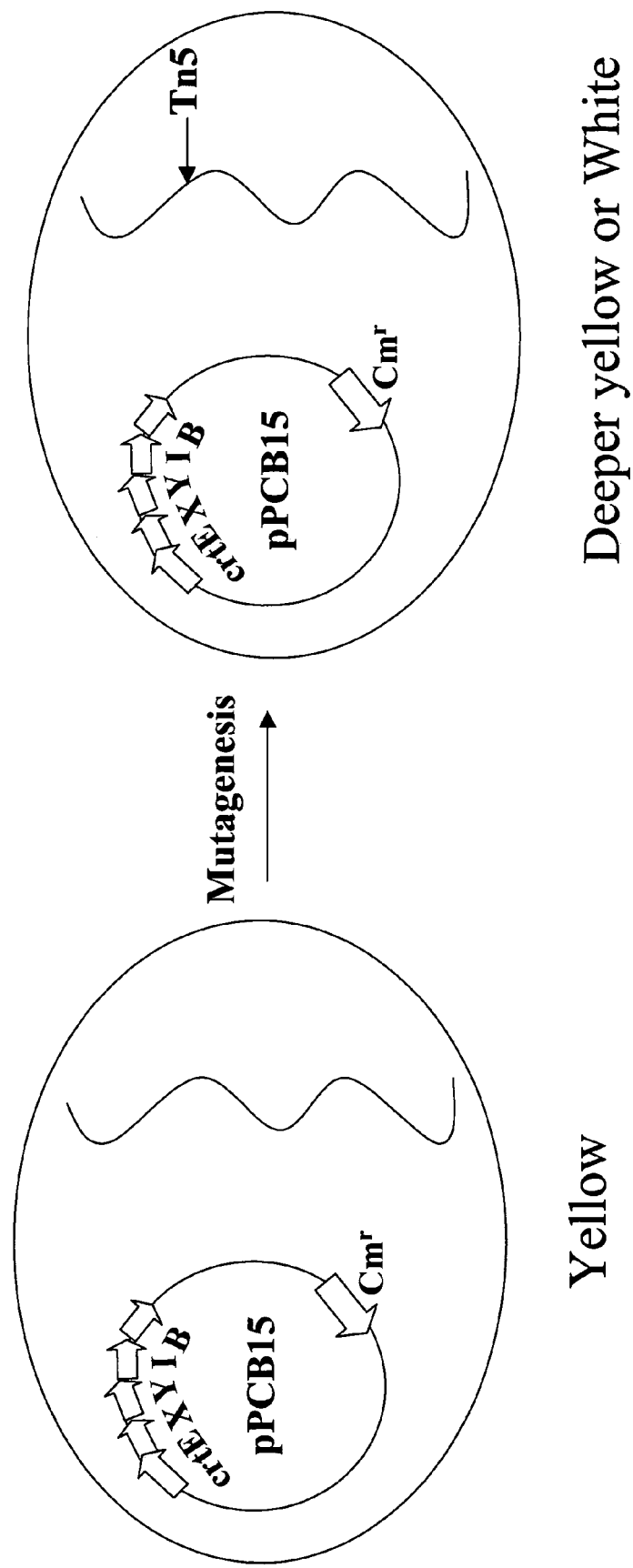
FIG. 1 shows the strategy for mutagenesis and screening of E. coli chromosomal mutants that affect carotenoid production.

Other mutations affecting plasmid copy number can be isolated using similar strategy as depicted in FIG. 1. The reporter gene on the plasmid can be any gene that permits an easy visual screen. Examples of reporter genes include, but are not limited to lacZ, gfp, lux, crt, xylMA, etc. Selection strategy may also be designed such that only gene expression from certain range of copy number of plasmids will allow survival of the hosts.

Additionally, it can be envisioned that the reporter genes may be incorporated into plasmids containing different types of replicons. The present method could be used to identify chromosomal mutations that alter the plasmid copy number for each type of replicon tested.

Lastly, the identified disrupted genes may be used alone or in combination to genetically engineer bacteria for optimal plasmid expression useful for industrial production of a desired genetic end product.

Production Host

The ColE1-like plasmids can be used to produce any genetic end products in any hosts that will support their replication. Preferred production hosts include those that have the ability to harbor ColE1-like plasmids. The ColE1 plasmids have been reported to replicate in some other bacteria in addition to Escherichia coli. The pUC- and pBR-based cloning vectors (both ColE1 type plasmids) were shown to be maintained in Pseudomonas stutzeri (Pemberton et al., Curr Microbiol, 25:25-29 (1992)). Plasmids containing the p15A origin of replication can replicate freely in Shewanella putrefaciens (Myers et al., Lett Appl Microbiol, 24:221-225 (1997)). Plasmids very similar to ColE1 plasmids were also isolated from other bacteria such as Salmonella enterica (Astill et al., Plasmid, 30:258-267 (1993); Erwinia stewartii (Fu et al., Plasmid, 34:75-84 (1995); Proteus vulgaris (Koons et al., Gene, 157:73-79 (1995); and Enterobacter agglomerans (Mikiewicz et al., Plasmid, 38:210-219 (1997)). Additional bacteria capable of supporting ColE1-like plasmids include Actinobacillus sp., Yersinia sp., and Pantoea sp. Most preferred production hosts are enteric production hosts, particularly those of the genera Escherichia and Salmonella.

Enteric bacteria are members of the family Enterobacteriaceae and include such members as Escherichia, Salmonella, and Shigella. They are gram-negative straight rods, 0.3-1.0×1.0-6.0 mm, motile by peritrichous flagella (except for Tatumella) or nonmotile. They grow in the presence and absence of oxygen and grow well on peptone, meat extract, and (usually) MacConkey's media. Some grow on D-glucose as the sole source of carbon, whereas others require vitamins and/or mineral(s). They are chemoorganotrophic with respiratory and fermentative metabolism but are not halophilic. Acid and often visible gas is produced during fermentation of D-glucose, other carbohydrates, and polyhydroxyl alcohols. They are oxidase negative and, with the exception of Shigella dysenteriae 0 group 1 and Xenorhabdus nematophilus, catalase positive. Nitrate is reduced to nitrite (except by some strains of Erwinia and Yersina). The G+C content of DNA is 38-60 mol % ($T_m$, Bd). DNAs from species within most genera are at least 20% related to one another and to Escherichia coli, the type species of the family. Notable exceptions are species of Yersina, Proteus, Providenica, Hafnia and Edwardsiella, whose DNAs are 10-20% related to those of species from other genera. Except for Erwinia chrysanthemi, all species tested contain the enterobacterial common antigen (Bergy's Manual of Systematic Bacteriology, D. H. Bergy et al., Baltimore: Williams and Wilkins, 1984).

General methods for introducing plasmids into these preferred hosts include chemical-induced transformation, electroporation, conjugation and transduction. The preferred hosts can be grown in tryptone yeast extract based rich media, or defined media with all the essential nutrients. Suitable antibiotics can be added in the growth media to maintain the plasmids. Similar gene mutations in the preferred hosts are expected to have similar effect of increasing copy number of the ColE1 and like plasmids replicated in these hosts.

DESCRIPTION OF PREFERRED EMBODIMENTS

Five mutant genes have been identified in E. coli which unexpectedly had effects on plasmid copy number. In particular, transposon mutagenesis of genes thrS, rpsA, rpoC, yjeR, and rhoL resulted in an increase of plasmid copy number of certain plasmids. The plasmids effected were those exhibiting anti-sense RNA copy-number control including those using the pMB1 and p15A replicons.

In one embodiment, the crt carotenoid biosynthesis gene cluster from *Pantoea stewartii* (ATCC No. 8199) was cloned, sequenced, and characterized (Examples 1 and 2; Tables 1 and 2). A reporter plasmid (pPCB15; SEQ ID NO. 28) was created which functionally expressed the crtEXYIB gene cluster (Example 3). The reporter plasmid was transformed into *E. coli* MG1655, enabling the strain to produce β-carotene (yellow colonies).

Figure 2:
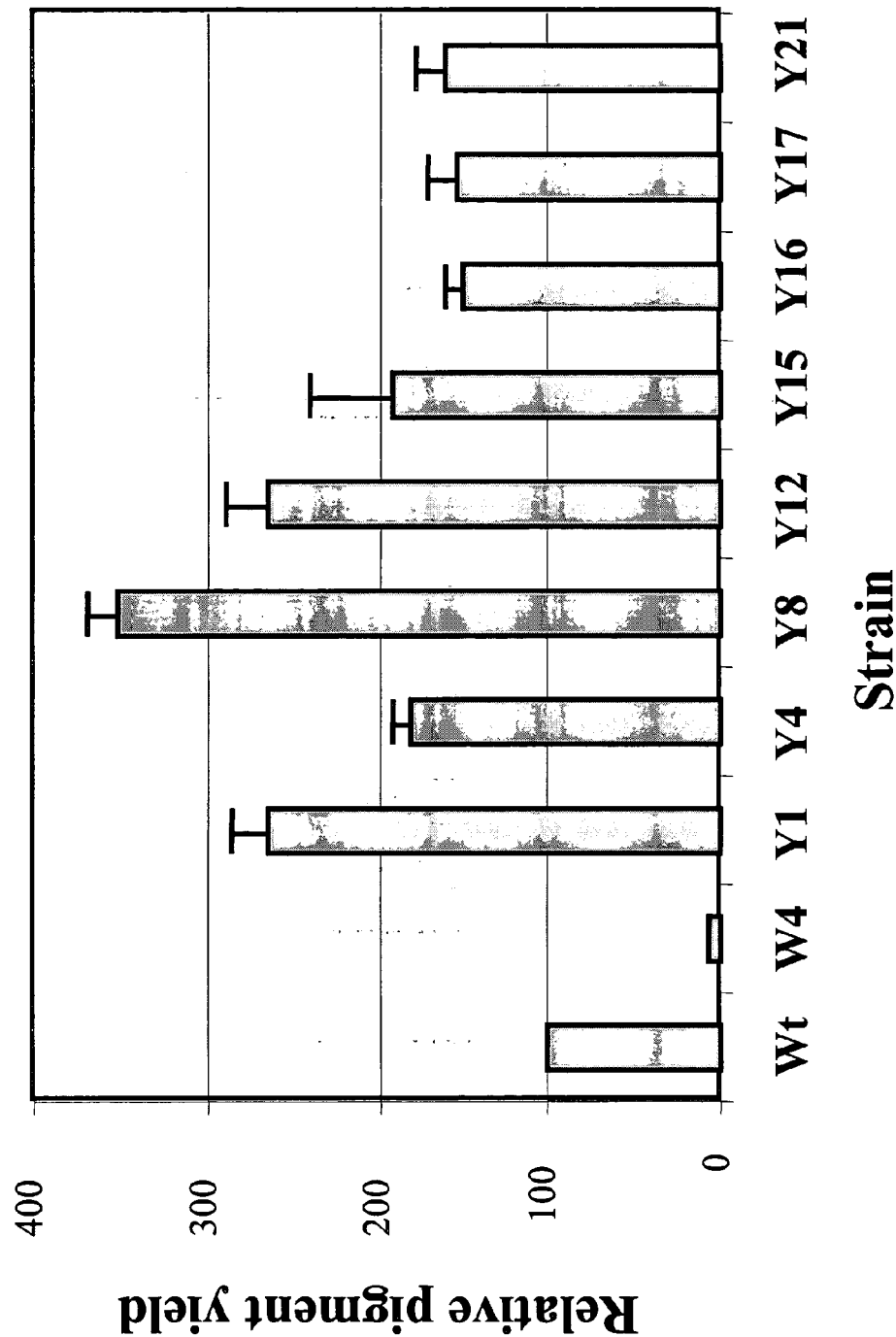
FIG. 2 shows the β-carotene production in E. coli mutants.

In another embodiment, transposon mutagenesis was conducted on *E. coli* MG1655 (pPCB15) (FIG. 1). Mutant colonies appearing to have a phenotypic color change (either deeper yellow or white appearance) were isolated and characterized. The level of β-carotene production was measured spectrophotometrically and verified by HPLC analysis (Example 3). The pigment yield was measured relative to the control strain harboring only the pPCB15 reporter plasmid (FIG. 2). Mutants Y4, Y15, Y16, Y17, and Y21 exhibited a 1.5-2 fold increase in β-carotene productionMutants Y1, Y8, and Y12 exhibited a 2.5-3.5 fold increase in β-carotene production. The chromosomal transposon insertion sites in the *E. coli* mutants were identified and sequenced (Example 4; Table 3).

In another embodiment, the increased carotenoid production in the mutant strains was attributed to an increase in reporter plasmid copy number. The reporter plasmid copy number was measured in the mutants (Example 5; FIGS. 3 and 4). Mutants Y1, Y8, Y12, Y15, and Y17 have a 2-4 fold increase in plasmid DNA when compared to the control Mutants Y4, Y16, and Y21 had comparable amounts of plasmid DNA to the control while mutant W4 had much less plasmid DNA (FIGS. 3 and 4).

In another embodiment, the increased in plasmid copy number was generally attributed to plasmids having ColE1-type replicons and was not specifically associated with the pPCB15 reporter plasmid. The pPCB15 reporter plasmid was cured from the mutants and different pACYC-derived plasmids were tested (Example 6). Plasmid pTV200, containing a luxCDABE reporter construct, was transformed into the various cured mutant strains. The lux activity was decreased 60% in W4, whereas it increased 4 to 7 fold in Y1 and Y8 mutants and over 10 fold in Y12, Y15, and Y17 mutants (FIG. 5). Plasmid pTV200 copy number was determined and was consistent with the change of luciferase activity (FIG. 6).

In another embodiment, the various mutant strains were shown to affect plasmids harboring p15A and pMB1 replicons. Plasmid pBR328 (pMB1 replicon) was transformed into cured mutant hosts Y1, Y8, Y12, Y15, and Y17. Plasmid pBR328 DNA levels were analyzed from the mutant hosts and were found to be increased approximately 2-4 fold above control levels (Example 7; FIG. 7). Various other plasmids with different replicon types were analyzed in mutant hosts W4 and Y15 versus the control (Example 8; Table 4). The increased copy number associated with the various mutations was not observed in plasmids harboring replicons other than pMB1 and p15A. The mutations observed in Y1, Y8, Y12, Y15 and Y17 were shown to increase plasmid copy number in plasmids with p15A and pMB1 replicons.

In another embodiment, reporter plasmids containing different replicons can be created and used to identify chromosomal mutations that increase plasmid copy number. The *Pantoea stewartii* crtEXYIB gene cluster could be cloned and expressed in reporter plasmids containing different replicons. Transposon mutagenesis could be used to identify mutations associated with each replicon type.

In another embodiment, the present method could be used to identify additional genes associated with increasing plasmid copy number in those plasmids having p15A and pMB1 replicons. These mutations, as well as those identified in the present invention, could be used alone or in combination to genetically engineer increased production of a desired genetic end product. In a preferred embodiment, the mutation information could be used to engineer *E. coli* strains for increased production of carotenoids.

EXAMPLES

The present invention is further defined in the following Examples. It should be understood that these Examples, while indicating preferred embodiments of the invention, are given by way of illustration only. From the above discussion and these Examples, one skilled in the art can ascertain the essential characteristics of this invention, and without departing from the spirit and scope thereof, can make various changes and modifications of the invention to adapt it to various usages and conditions.

General Methods

Standard recombinant DNA and molecular cloning techniques used in the Examples are well known in the art and are described by Sambrook, J., Fritsch, E. F. and Maniatis, T. *Molecular Cloning: A Laboratory Manual*; Cold Spring Harbor Laboratory Press: Cold Spring Harbor, (1989) (Maniatis) and by T. J. Silhavy, M. L. Bennan, and L. W. Enquist, *Experiments with Gene Fusions*, Cold Spring Harbor Laboratory, Cold Spring Harbor, N.Y. (1984) and by Ausubel, F. M. et al., *Current Protocols in Molecular Biology*, pub. by Greene Publishing Assoc. and Wiley-Interscience (1987).

Materials and methods suitable for the maintenance and growth of bacterial cultures are well known in the art. Techniques suitable for use in the following examples may be found as set out in *Manual of Methods for General Bacteriology* (Phillipp Gerhardt, R. G. E. Murray, Ralph N. Costilow, Eugene W. Nester, Willis A. Wood, Noel R. Krieg and G. Briggs Phillips, eds), American Society for Microbiology, Washington, D.C. (1994)) or by Thomas D. Brock in *Biotechnology: A Textbook of Industrial Microbiology*, Second Edition, Sinauer Associates, Inc., Sunderland, Mass. (1989). All reagents, restriction enzymes and materials used for the growth and maintenance of bacterial cells were obtained from Aldrich Chemicals (Milwaukee, Wis.), DIFCO Laboratories (Detroit, Mich.), GIBCO/BRL (Gaithersburg, Md.), or Sigma Chemical Company (St. Louis, Mo.) unless otherwise specified.

Manipulations of genetic sequences were accomplished using the suite of programs available from the Genetics Computer Group Inc. (Wisconsin Package Version 9.0, Genetics Computer Group (GCG), Madison, Wis.). Where the GCG program "Pileup" was used the gap creation default value of 12, and the gap extension default value of 4 were used. Where the CGC "Gap" or "Bestfit" programs were used the default gap creation penalty of 50 and the default gap extension penalty of 3 were used. Multiple alignments were created using the FASTA program incorporating the Smith-Waterman algorithm (W. R. Pearson, *Comput. Methods Genome Res.*, [Proc. Int. Symp.] (1994), Meeting Date 1992, 111-20. Editor(s): Suhai, Sandor. Publisher: Plenum, New York, N.Y.). In any case where program parameters were not prompted for, in these or any other programs, default values were used.

The meaning of abbreviations is as follows: "h" means hour(s), "min" means minute(s), "sec" means second(s), "d" means day(s), "μL" means microliter(s), "mL" means milliliter(s), "L" means liter(s), and "rpm" means revolutions per minute.

Example 1

Cloning of β-Carotene Production Genes from *Pantoea stewartii*

Primers were designed using the sequence from *Erwinia uredovora* to amplify a fragment by PCR containing the crt genes. These sequences included 5'-3':

```
ATGACGGTCTGCGCAAAAAAACACG       SEQ ID 13

GAGAAATTATGTTGTGGATTTGGAATGC    SEQ ID 14
```

Chromosomal DNA was purified from *Pantoea stewartii* (ATCC NO. 8199) and Pfu Turbo polymerase (Stratagene, La Jolla, Calif.) was used in a PCR amplification reaction under the following conditions: 94° C., 5 min; 94° C. (1 min)-60° C. (1 min)-72° C. (10 min) for 25 cycles, and 72° C. for 10 min. A single product of approximately 6.5 kb was observed following gel electrophoresis. Taq polymerase (Perkin Elmer, Foster City, Calif.) was used in a ten minute 72° C. reaction to add additional 3' adenosine nucleotides to the fragment for TOPO cloning into pCR4-TOPO (Invitrogen, Carlsbad, Calif.) to create the plasmid pPCB13. Following transformation to *E. coli* DH5α (Life Technologies, Rockville, Md.) by electroporation, several colonies appeared to be bright yellow in color indicating that they were producing a carotenoid compound. Following plasmid isolation as instructed by the manufacturer using the Qiagen (Valencia, Calif.) miniprep kit, the plasmid containing the 6.5 kb amplified fragment was transposed with pGPS1.1 using the GPS-1 Genome Priming System kit (New England Biolabs, Inc., Beverly, Mass.). A number of these transposed plasmids were sequenced from each end of the transposon. Sequence was generated on an ABI Automatic sequencer using dye terminator technology (U.S. Pat. No. 5,366,860; EP 272007) using transposon specific primers. Sequence assembly was performed with the Sequencher program (Gene Codes Corp., Ann Arbor, Mich.).

Example 2

Identification and Characterization of *Pantoea stewartii* Genes

Genes encoding crtE, X, Y, I, B, and Z, cloned from *Pantoea stewartii*, were identified by conducting BLAST (Basic Local Alignment Search Tool; Altschul et al., *J. Mol. Biol.*, 215:403-410 (1993)) searches for similarity to sequences contained in the BLAST "nr" database (comprising all non-redundant GenBank® CDS translations, sequences derived from the 3-dimensional structure Brookhaven Protein Data Bank, the SWISS-PROT protein sequence database, EMBL, and DDBJ databases). The sequences obtained were analyzed for similarity to all publicly available DNA sequences contained in the "nr" database using the BLASTN algorithm provided by the National Center for Biotechnology Information (NCBI). The DNA sequences were translated in all reading frames and compared for similarity to all publicly available protein sequences contained in the "nr" database using the BLASTX algorithm (Gish, W. and States, D., *Nature Genetics*, 3:266-272 (1993)) provided by the NCBI.

All comparisons were done using either the BLASTNnr or BLASTXnr algorithm. The results of the BLAST comparison is given in Table 2 which summarize the sequences to which they have the most similarity. Table 2 displays data based on the BLASTXnr algorithm with values reported in expect values. The Expect value estimates the statistical significance of the match, specifying the number of matches, with a given score, that are expected in a search of a database of this size absolutely by chance.

TABLE 2

| ORF Name | Gene Name | Similarity Identified | SEQ ID base | SEQ ID Peptide | % Identity[a] | % Similarity[b] | E-value[c] | Citation |
|---|---|---|---|---|---|---|---|---|
| 1 | crtE | Geranylgeranyl pryophosphate synthetase (or GGPP synth or farnesyltranstransferase) EC 2.5.1.29 gi\|117509\|sp\|P21684\|CRTE_PANAN GERANYLGERANYL PYROPHOSPHATE SYNTHETASE (GGPP SYNTHETASE) (FARNESYL TRANSTRANSFERASE) | 1 | 2 | 83 | 88 | e-137 | Misawa et al., J. Bacteriol. 172 (12), 6704-6712 (1990) |
| 2 | crtX | Zeaxanthin glucosyl transferase EC 2.4.1.- gi\|1073294\|pir\|\|S52583 crtX protein - *Erwinia herbicola* | 3 | 4 | 75 | 79 | 0.0 | Lin et al., Mol. Gen. Genet. 245 (4), 417-423 (1994) |
| 3 | crtY | Lycopene cyclase gi\|1073295\|pir\|\|S52585 lycopene cyclase - *Erwinia herbicola* | 5 | 6 | 83 | 91 | 0.0 | Lin et al., Mol. Gen. Genet. 245 (4), 417-423 (1994) |
| 4 | crtI | Phytoene desaturaseEC 1.3.-.- gi\|1073299\|pir\|\|S52586 phytoene dehydrogenase (EC 1.3.—.—) - *Erwinia herbicola* | 7 | 8 | 89 | 91 | 0.0 | Lin et al., Mol. Gen. Genet. 245 (4), 417-423 (1994) |
| 5 | crtB | Phytoene synthaseEC2.5.1.- gi\|1073300\|pir\|\|S52587 prephytoene pyrophosphate synthase - *Erwinia herbicola* | 9 | 10 | 88 | 92 | e-150 | Lin et al., Mol. Gen. Genet. 245 (4), 417-423 (1994) |

TABLE 2-continued

| ORF Name | Gene Name | Similarity Identified | SEQ ID base | SEQ ID Peptide | % Identity[a] | % Similarity[b] | E-value[c] | Citation |
|---|---|---|---|---|---|---|---|---|
| 6 | crtZ | Beta-carotene hydroxylase gi|117526|sp|P21688|CRTZ_PANAN BETA-CAROTENE HYDROXYLASE | 11 | 12 | 88 | 91 | 3e-88 | Misawa et al., J. Bacteriol. 172 (12), 6704-6712 (1990) |

[a]% Identity is defined as percentage of amino acids that are identical between the two proteins.
[b]% Similarity is defined as percentage of amino acids that are identical or conserved between the two proteins.
[c]Expect value. The Expect value estimates the statistical significance of the match, specifying the number of matches, with a given score, that are expected in a search of a database of this size absolutely by chance.

Example 3

Isolation of Chromosomal Mutations that Affect Carotenoid Production

Wild type *E. coli* is non-carotenogenic and synthesizes only the farnesyl pyrophosphate precursor for carotenoids. When the crtEXYIB gene cluster from *Pantoea stewartii* was introduced into *E.coli*, β-carotene was synthesized and the cells became yellow. *E. coli* chromosomal mutations which increase carotenoid production should result in deeper yellow colonies. *E. coli* chromosomal mutations which decrease carotenoid production should result in lighter yellow or white colonies (FIG. 1).

The β-carotene reporter plasmid, pPCB15 (cam$^R$), encodes the carotenoid biosynthesis gene cluster (crtEXYIB) from *Pantoea Stewartii* (ATCC NO. 8199). The pPCB15 plasmid (SEQ ID NO. 28) was constructed from ligation of SmaI digested pSU18 (Bartolome et al., *Gene*, 102:75-78 (1991)) vector with a blunt-ended PmeI/NotI fragment carrying crtEXYIB from pPCB13 (Example 1). *E. coli* MG1655 transformed with pPCB15 was used for transposon mutagenesis. Mutagenesis was performed using EZ:TN™<KAN-2>Tnp Transposome™ kit (Epicentre Technologies, Madison, Wis.) according to manufacturer's instructions. A 1 µL volume of the transposome was electroporated into 50 µL of highly electro-competent MG1655 (pPCB15) cells. The mutant cells were spread on LB-Noble Agar (Difco laboratories, Detroit, Mich.) plates with 25 µg/mL kanamycin and 25 µg/mL chloramphenicol, and grown at 37° C. overnight. Tens of thousands of mutant colonies were visually examined for deeper or lighter color development. The candidate mutants were re-streaked and frozen for further characterization.

To confirm if the deeper or lighter color colonies were indeed indicative of amount of β-carotene production, the carotenoids in the candidate mutants were extracted and quantified spectrophotometrically. Each candidate clone was cultured in 10 mL LB medium with 25 µg/mL chloramphenicol in 50 mL flasks overnight shaking at 250 rpm. MG1655(pPCB15) was used as the control. Carotenoid was extracted from each cell pellet for 15 min into 1 mL acetone, and the amount of β-carotene produced was measured at 455 nm. Cell density was measured at 600 nm. OD455/OD600 was used to normalize β-carotene production for different cultures. β-carotene production was also verified by HPLC. The averages of three independent measurements with standard deviations are shown in FIG. 2. Among the mutant clones tested, eight showed increased β-carotene production. Mutants Y1, Y8 and Y12 showed 2.5-3.5 fold higher β-carotene production. Mutants Y4, Y15, Y16, Y17 and Y21 showed 1.5-2 fold higher β-carotene production. Mutant W4 was a white mutant that decreased β-carotene production to 17% of that of the MG1655(pPCB15) control.

Example 4

Mapping of the Transposon Insertions in *E. coli* Chromosome

The transposon insertion site in each mutant was identified by PCR and sequencing directly from the chromosome. A modified single-primer PCR method (Karlyshev et al., *BioTechniques*, 28:1078-82 (2000)) was used. A 100 µL volume of culture grown overnight was heated at 99° C. for 10 min in a PCR machine. Cell debris was removed at 4000 g for 10 min. A 1 µL volume of the supernatant was used in a 50 µL PCR reaction using either Tn5PCRF (5'-GCTGAGTTGAAGGATCAGATC-3';SEQ ID 15) or Tn5PCRR (5'-CGAGCAAGACGTTTCCCGTTG-3';SEQ ID 16) primer. PCR was carried out as follows: 5 min at 95° C.; 20 cycles of 92° C. for 30 sec, 60° C. for 30 sec, 72° C. for 3 min; 30 cycles of 92° C. for 30 sec, 40° C. for 30 sec, 72° C. for 2 min; 30 cycles of 92° C. for 30 sec, 60° C. for 30 sec, and 72° C. for 2 min. A 10 µL volume of each PCR product was checked on an agarose gel. A 40 µL volume of each PCR product was purified using Qiagen PCR cleanup kit, and sequenced using sequencing primers Kan-2 FP-1 (5'-ACCTACAACAAAGCTCTCATCAACC-3';SEQ ID 17) or Kan-2 RP-1 (5'-GCAATGTAACATCAGAGATTTTGAG-3';SEQ ID 18) provided by the EZ:TN™<KAN-2>Tnp Transposome™ kit. The chromosomal insertion site of the transposon was identified as the junction between the Tn5 transposon and MG1655 chromosome DNA by aligning the sequence obtained from each mutant with the *E. coli* genomic sequence. Table 3 summarizes the chromosomal insertion sites of the mutants. The numbers refer to the standard base pair (bp) numbers for *E. coil* genome of MG1655 (GenBank® Accession No. U00096). Majority of the genes affected are involved in transcription, translation or RNA stability. Five of them (thrS, rpsA, rpoC, yjeR, rhoL) were previously reported to be essential. The transposon insertions we obtained in these genes were very close to the carboxyl terminal end and most likely resulted in functional although truncated proteins.

TABLE 3

Localization of the transposon insertions in *E. coli* chromosome

| Mutant | Transposon Insertion Site | Gene disrupted Location in *E. coli* chromosome | Gene Function | Essentiality reported | Reference |
|---|---|---|---|---|---|
| W4 | 158904 | pcnB: 157729-159093 | poly(A) polymerase | No | Masters M, 1993 J Bacteriol 175: 4405-12 |
| Y1 | 1798679 | thrS: 1798666-1800594 | threonyl-tRNA synthetase | Yes | Johnson EJ, 1977 J Bacteriol 129: 66-70 |
| Y4 | 3304788 | deaD: 3303612-3305552 | RNA helicase | No | Toone WM, 1991 J Bacteriol 173: 3291-302 |
| Y8 | 962815 | rpsA: 961218-962891 | 30S ribosomal subunit protein S1 | Yes | Kitakawa M, 1982 Mol Gen Genet 185: 445-7 |
| Y12 | 4187062 | rpoC: 4182928-4187151 | RNA polymerase β' subunit | Yes | Post, L. E, 1979 PNAS 76: 1697-1701 |
| Y15 | 4389704 | yjeR: 4389113-4389727 | oligo-ribonuclease | Yes | Ghosh S, 1999 PNAS 96: 4372-7. |
| Y16 | 3396592 | mreC: 3396512-3397615 | rod shape-determining protein | No | Wachi M, 1987 J Bacteriol 169: 4935-40 |
| Y17 | 3963892 | rhoL: 3963846-3963947 | rho operon leader peptide | Yes | Das A, 1976 PNAS 73: 1959-63 |
| Y21 | 2657233 | yfhE (hscB): 2656972-2657487 | heat shock cognate protein | Unknown | Takahashi Y, 1999 J Biochem (Tokyo) 126: 917-26 |

Example 5

Analysis of Plasmid Copy Number in the Mutants Affecting β-carotene Production White mutant W4 had a transposon insertion in pcnB gene (SEQ ID NO. 27), which encodes a poly(A) polymerase that polyadenylates RNA. Mutation in pcnB gene was reported to decrease the copy number of ColE1 plasmids. It was possible that the effect on carotenoid production in some of the mutants was due to copy number change of the carotenoid-synthesizing plasmid. We analyzed the amount of the β-carotene synthesizing plasmid pPCB15, a derivative of pACYC plasmids, in the isolated mutants. Cells were grown in LB containing chloramphenicol (25 μg/mL) with shaking overnight. Cell density was measured by OD600. Plasmid DNA was isolated from same amount of cells (not the same volume) using Qiagen miniprep spin kit. A 5-μL volume of EcoRI-digested plasmid DNA isolated from each strain was loaded on an agarose gel for comparison. FIG. 3 shows the plasmid DNA isolated from two independent clones of each stain. In both experiments, Mutants Y1, Y8, Y12, Y15 and Y17 appeared to have more plasmid DNA than wild type MG1655. Mutant W4 had much less plasmid DNA. Mutants Y4, Y16 and Y21 had comparable amount of plasmid DNA as MG1655. To estimate the change of the plasmid copy number 1 μL, 2 μL and 4 μL of digested DNA from Y1, Y8, Y12, Y15, Y17 and MG1655 were loaded on an agarose gel as shown in FIG. 4. All five mutants showed a 2 to 4 fold increase in plasmid copy number compared to MG1655. It is interesting to note that these five mutants all contained mutations in an essential gene. A recent report described a different mutation of rpoC from that in Y12 mutant that decreased the copy number of ColE1 plasmids (Ederth et al., *Mol. Gen. Genomics*, 267:587-592 (2002)).

Example 6

Luciferase Expression in *E. coli* Mutants that Affect Plasmid Copy Number

To determine if the copy number effect was specifically associated with the carotenoid-synthesizing plasmid or not, the pPCB15 (Cam$^R$) plasmid was cured from the mutants. A different pACYC-derived plasmid was tested in the cured strains. The plasmid-cured strains were isolated by growing the cells in the absence of chloramphenicol and plating dilutions on LB plates containing kanamycin. The kanamycin resistant colonies that became chloramphenicol sensitive had presumably lost the pPCB15 plasmid.

Plasmid pTV200 contains a promoterless luxCDABE from *P. luminescens* in pACYC184. *E. coli* strains containing pTV200 are positive for luciferase (lux) activity, presumably due to expression from the chloramphenicol resistance gene promoter on pACYC184 vector. We tested luciferase expression of pTV200 in different cured strains.

Bacterial bioluminescence is a phenomenon in which the products of 5 structural genes (luxA, luxB, luxC, luxD, and luxE) work in concert to produce light. The luxD product generates a C14 fatty acid from a precursor. The C14 fatty acid is activated in an ATP dependent reaction to an acyl-enzyme conjugate through the action of the luxE product, which couples bacterial bioluminescence to the cellular energetic state. The acyl-enzyme (luxE product) serves as a transfer agent, donating the acyl group to the luxC product. The acyl-LuxC binary complex is then reduced in a reaction in which NADPH serves as an electron pair and proton donor reducing the acyl conjugate to the C14 aldehyde. This reaction couples the reducing power of the cell to bacterial light emission. The light production reaction, catalyzed by luciferase (the product of luxA and luxB), generates light. The energy for light emission is provided by the aldehyde to fatty acid conversion and $FMNH_2$ oxidation, providing another couple between light production and the cellular energy state.

The *Photorabdus luminenscens* luxAB genes were used as reporters for plasmid copy number alterations via the mutated genes (Van Dyk et al., *Appl. Environ. Microbiol.*, 180:785-792 (1995)). Plasmid pTV200 is a pACYC184-derived plasmid carrying the *Photorhabdus luminescens* luxCDABE operon. It was constructed in the following manner. Plasmid pJT205 (Van Dyk, T., and Rosson, R., *Photorhabulus luminescens* luxCDABE promoter probe vectors, in *Method in Molecular Biology: Bioluminescence Methods and Protocols*, Vol. 102, LaRossa, R. A., Ed., Humana Press Inc., Towowa, N.J., pp. 85 (1998)) was digested with restriction enzymes EcoRI and PvuII. The products of this digestion were ligated with plasmid pACYC184 that had been digested with the same two enzymes. The ligation mixture was used to transform *E. coli* strain DH5α, selecting for tetracycline resistance. The agar plates containing the transformant colonies were use to expose Kodak XAR film and colonies that produced light were purified. The light-producing colonies were screened for sensitivity to ampicillin and chloramphenicol. Plasmid DNA was obtained from one tetracycline-resistant, light-producing, ampicillin-sensitive, and chloramphenicol-sensitive isolate. This plasmid, named pTV200, had two bands of the expected size following BamHI digestion.

Plasmid pTV200 was transformed into the plasmid-cured mutant strains with tetracycline selection. Luciferase activity and pTV200 plasmid concentration were analyzed from the mutants. Cells containing pTV200 were grown in LB with 10 μg/mL of tetracycline at 37° C. with shaking overnight. A 100-μL volume of each cell culture was pipetted into a 96-well plate and luciferase activity was measured using HTS 7000 Plus BioAssay Reader (Perkin Elmer, Norwalk, Conn.). Cell density of the samples in each well was also measured by absorption at OD600 using the BioAssay Reader. The normalized luciferase activity of each sample was calculated and is shown in FIG. 5. The lux activity decreased 60% in W4 mutant compared to the wild type MG1655, whereas it increased 4 to 7 fold in Y1 and Y8 mutants and over 10 fold in Y12, Y15 and Y17 mutants. Plasmid DNA was also isolated from same amount of cells for different strains and digested with EcoRI. Aliquots (2 μL and 4 μL) of digested plasmid DNA were loaded on agarose gels. Comparison of pTV200 isolated from wild type MG1655 and mutants is shown in FIG. 6. Consistent with the luciferase activity assay, the copy number of pTV200 decreased in the W4 mutant, whereas it increased in Y1, Y8, Y12, Y15 and Y17 mutants.

Example 7

Effect of the Chromosomal Mutations on the Copy Number of Plasmids of PMB1 Replicon It is known that pcnB mutation affects copy number of plasmids of both p15A and pMB1 replicons (Liu et al., supra). We tested if the other mutations we isolated also affected copy number of pMB1-derived plasmids. Plasmid pBR328 (pMB1 replicon) was transformed into cured mutant hosts of Y1, Y8, Y12, Y15 and Y17. Plasmid DNA was isolated from same amount of cells from each strain and digested with EcoRI. Aliquots (2 μL and 4 μL) of digested plasmid DNA were loaded on agarose gels. As shown in FIG. 7, the copy number of pBR328 increased approximately 2-4 fold in Y1, Y8, Y12, Y15 and Y17 mutants comparing to that in the wild type MG1655.

Example 8

Effect of the Chromosomal Mutations on the Copy Number of Plasmids of Different Replicons To determine if the above mutations would affect the copy number of other plasmids, we tested a list of plasmids of different replicons (Table 4) in these mutant hosts. A representative of the mutants that increase the plasmid copy number, Y15, and the W4 mutant that decreased the plasmid copy number were used for this experiment. Plasmids shown in Table 4 were transformed into MG1655 and the cured mutant hosts of W4 and Y15, and selected with the respective antibiotics. The cells were grown in LB containing the appropriate antibiotics and plasmid DNA was prepared from the same amount of cells using Qiagen miniprep spin columns (Qiagen, Inc., Carlsbad, Calif.). Plasmid DNA was digested with EcoRI and aliquots of the digested DNA (1 μL, 2 μL, 4 μL, and 16 μL) were loaded on an agarose gel (FIG. 8). The pcnB (in W4) or yjeR (in Y15) mutation did not appear to affect the copy number of pSC101, pBHR1, pMMB66 and pTJS75. The pcnB mutation decreased the copy number of pBR328 and pACYC184 more than 16 fold. The yjeR mutation increased the copy number of pBR328 and pACYC184 about 2 fold. Therefore, these *E. coli* chromosomal mutations affected the copy number of plasmids with replicons pMB1 and/or p15A.

TABLE 4

Plasmids of different replicons tested in the W4 and Y15 mutant hosts

| Plasmid | Replicon | Antibiotic marker | Reference |
|---|---|---|---|
| pBR328 | pMB1 | $Cm^r\ Ap^r\ Tc^r$ | Balbas, P. 1986 Gene 50: 3-40 |
| pACYC184 | p15A | $Cm^r\ Tc^r$ | Chang, ACY. 1978 J. Bacteriol. 134: 1141-56 |
| pSC101 | pSC101 | $Tc^r$ | Cohen, SN. 1977 J. Bacteriol. 132: 734-737 |
| pBHR1 | pBBR1 | $Cm^r\ Kn^r$ | Antoine, R. 1992 Mol Microbiol. 6: 1785-99 |
| pMMB66 | RSF1010 (IncQ) | $Ap^r$ | Scholz, P. 1989 Gene 75: 271-288 |
| pTJS75 | RK2 (IncP) | $Tc^r$ | Schmidhauser, TJ. 1985 J. Bacteriol. 164: 446-455 |

What is claimed is:

1. A bacterial production host comprising:
   a) a plasmid comprising:
      (i) a target gene to be expressed; and
      (ii) a replicon controlled by antisense-RNA regulation; and
   b) a mutation in a gene selected from the group consisting of thrS, rpsA, rpoC, yjeR, and rhoL wherein the nucleotide sequence of the mutated thrS gene is SEQ ID NO:19; the nucleotide sequence of the mutated rpsA gene is SEQ ID NO:21; the nucleotide sequence of the mutated rpoC gene is SEQ ID NO:22; the nucleotide sequence of the mutated yjeR gene is SEQ ID NO:23; and the sequence of the mutated rhoL gene is SEQ ID NO:25.

2. A bacterial production host according to claim 1 wherein the host is *E. coli*.

3. A bacterial production host comprising:
   a) a plasmid comprising:
      (i) a target gene to be expressed; and
      (ii) a replicon controlled by anti-sense RNA regulation; and
   b) a mutation in a gene selected from the group consisting of thrS, rpsA, rpoC, yjeR, and rhoL where the mutation of the thrS gene is at the 1798679 base of the *E. coli* chromosome; the mutation of the rpsA gene is at 962815 base of the *E. coli* chromosome; the mutation of the rpoC gene is at 4187062 base of the *E. coli* chromosome; the mutation of the yjeR gene is at 4389704 base of the *E. coli* chromosome; and the mutation of the rhoL gene is at 3963892 base of the *E. coli* chromosome; wherein the bacterial production host is *E. coli*.

4. A bacterial production host according to any of claims 1-3 wherein the plasmid of step (a) comprises a replicon selected from the group consisting of p15A and pMB1.

5. A bacterial production host according to any of claims 1-3 wherein the target gene encodes a polypeptide useful in the production of a genetic end product selected from the group consisting of isoprenoids, carotenoids, terpenoids, tetrapyrroles, polyketides, vitamins, amino acids, fatty acids, proteins, nucleic acids, carbohydrates, antimicrobial agents, anticancer agents, poly-hydroxyalkanoic acid synthases, nitrilases, nitrile hydratases, amidases, enzymes used in the production of synthetic silk proteins, pyruvate decarboxylases, alcohol dehydrogenases, and biological metabolites.

6. A bacterial production host according to any of claims 1-3 wherein the target gene is selected from the group consisting of crtE, crtB, crtl, crtY, crtX and crtZ.

7. A bacterial production host according to claim 1 selected from the group consisting of *Pseudomonas, Shewanella, Erwinia, Proteus, Enterobacter, Actinobacilus, Yersinia*, and *Pantoea*.

8. A bacterial production host according to claim 1 wherein the host is an enteric bacteria.

9. A bacterial production host according to claim 8 selected from the group consisting of *Escherichia* and *Salmonella*.

10. A method for the expression of a target gene comprising:
    a) providing a bacterial production host according to any one of claims 1-3; and
    b) growing the bacterial production host of step (a) under suitable conditions wherein the target gene is expressed.

11. A method according to claim 10 wherein the target gene encodes a polypeptide useful in the production of a genetic end product selected from the group consisting of isoprenoids, carotenoids, terpenoids, tetrapyrroles, polyketides, vitamins, amino acids, fatty acids, proteins, nucleic acids, carbohydrates, antimicrobial agents, anticancer agents, poly-hydroxyalkanoic acid synthases, nitrilases, nitrile hydratases, amidases, enzymes used in the production of synthetic silk proteins, pyruvate decarboxylases, alcohol dehydrogenases, and biological metabolites.

12. A method according to claim 11 wherein the target gene is selected from the group consisting of crtE, crtB, crtI, crtY, crtX and crtZ.

* * * * *

SEQUENCE LISTING

<160> NUMBER OF SEQ ID NOS: 28

<210> SEQ ID NO 1
<211> LENGTH: 912
<212> TYPE: DNA
<213> ORGANISM: Pantoea stewartii
<220> FEATURE:
<221> NAME/KEY: misc_feature
<222> LOCATION: (1)..(3)
<223> OTHER INFORMATION: Alternative start code TTG instead of ATG used.

<400> SEQUENCE: 1

```
ttgacggtct gcgcaaaaaa acacgttcac cttactggca tttcggctga gcagttgctg      60
gctgatatcg atagccgcct tgatcagtta ctgccggttc agggtgagcg ggattgtgtg     120
ggtgccgcga tgcgtgaagg cacgctggca ccgggcaaac gtattcgtcc gatgctgctg     180
ttattaacag cgcgcgatct ggctgtgcg atcagtcacg ggggattact ggatttagcc      240
tgcgcggttg aaatggtgca tgctgcctcg ctgattctgg atgatatgcc ctgcatggac     300
gatgcgcaga tgcgtcgggg gcgtcccacc attcacacgc agtacggtga acatgtggcg     360
attctggcgg cggtcgcttt actcagcaaa gcgtttgggg tgattgccga ggctgaaggt     420
ctgacgccga tagccaaaac tcgcgcggtg tcggagctgt ccactgcgat tggcatgcag     480
ggtctggttc agggccagtt taaggacctc tcggaaggcg ataaaccccg cagcgccgat     540
gccatactgc taaccaatca gtttaaaacc agcacgctgt tttgcgcgtc aacgcaaatg     600
gcgtccattg cggccaacgc gtcctgcgaa gcgcgtgaga acctgcatcg tttctcgctc     660
gatctcggcc aggcctttca gttgcttgac gatcttaccg atggcatgac cgataccggc     720
aaagacatca atcaggatgc aggtaaatca acgctggtca atttattagg ctcaggcgcg     780
gtcgaagaac gcctgcgaca gcatttgcgc ctggccagtg aacacctttc cgcggcatgc     840
caaaacggcc attccaccac ccaactttttt attcaggcct ggtttgacaa aaaactcgct    900
gccgtcagtt aa                                                        912
```

<210> SEQ ID NO 2
<211> LENGTH: 303
<212> TYPE: PRT
<213> ORGANISM: Pantoea stewartii

<400> SEQUENCE: 2

```
Met Thr Val Cys Ala Lys Lys His Val His Leu Thr Gly Ile Ser Ala
1               5                   10                  15

Glu Gln Leu Leu Ala Asp Ile Asp Ser Arg Leu Asp Gln Leu Leu Pro
            20                  25                  30

Val Gln Gly Glu Arg Asp Cys Val Gly Ala Ala Met Arg Glu Gly Thr
        35                  40                  45

Leu Ala Pro Gly Lys Arg Ile Arg Pro Met Leu Leu Leu Thr Ala
    50                  55                  60

Arg Asp Leu Gly Cys Ala Ile Ser His Gly Gly Leu Leu Asp Leu Ala
65                  70                  75                  80

Cys Ala Val Glu Met Val His Ala Ala Ser Leu Ile Leu Asp Asp Met
                85                  90                  95

Pro Cys Met Asp Asp Ala Gln Met Arg Arg Gly Arg Pro Thr Ile His
            100                 105                 110

Thr Gln Tyr Gly Glu His Val Ala Ile Leu Ala Ala Val Ala Leu Leu
        115                 120                 125
```

```
Ser Lys Ala Phe Gly Val Ile Ala Glu Ala Glu Gly Leu Thr Pro Ile
    130                 135                 140

Ala Lys Thr Arg Ala Val Ser Glu Leu Ser Thr Ala Ile Gly Met Gln
145                 150                 155                 160

Gly Leu Val Gln Gly Gln Phe Lys Asp Leu Ser Glu Gly Asp Lys Pro
            165                 170                 175

Arg Ser Ala Asp Ala Ile Leu Leu Thr Asn Gln Phe Lys Thr Ser Thr
        180                 185                 190

Leu Phe Cys Ala Ser Thr Gln Met Ala Ser Ile Ala Ala Asn Ala Ser
    195                 200                 205

Cys Glu Ala Arg Glu Asn Leu His Arg Phe Ser Leu Asp Leu Gly Gln
210                 215                 220

Ala Phe Gln Leu Leu Asp Asp Leu Thr Asp Gly Met Thr Asp Thr Gly
225                 230                 235                 240

Lys Asp Ile Asn Gln Asp Ala Gly Lys Ser Thr Leu Val Asn Leu Leu
            245                 250                 255

Gly Ser Gly Ala Val Glu Glu Arg Leu Arg Gln His Leu Arg Leu Ala
        260                 265                 270

Ser Glu His Leu Ser Ala Ala Cys Gln Asn Gly His Ser Thr Thr Gln
275                 280                 285

Leu Phe Ile Gln Ala Trp Phe Asp Lys Lys Leu Ala Ala Val Ser
    290                 295                 300

<210> SEQ ID NO 3
<211> LENGTH: 1296
<212> TYPE: DNA
<213> ORGANISM: Pantoea stewartii
<220> FEATURE:
<221> NAME/KEY: CDS
<222> LOCATION: (1)..(1296)

<400> SEQUENCE: 3 atg agc cat ttt gcg gtg atc gca ccg ccc ttt ttc agc cat gtt cgc     48
Met Ser His Phe Ala Val Ile Ala Pro Pro Phe Phe Ser His Val Arg
1               5                   10                  15 gct ctg caa aac ctt gct cag gaa tta gtg gcc cgc ggt cat cgt gtt     96
Ala Leu Gln Asn Leu Ala Gln Glu Leu Val Ala Arg Gly His Arg Val
                20                  25                  30 acg ttt ttt cag caa cat gac tgc aaa gcg ctg gta acg ggc agc gat    144
Thr Phe Phe Gln Gln His Asp Cys Lys Ala Leu Val Thr Gly Ser Asp
            35                  40                  45 atc gga ttc cag acc gtc gga ctg caa acg cat cct ccc ggt tcc tta    192
Ile Gly Phe Gln Thr Val Gly Leu Gln Thr His Pro Pro Gly Ser Leu
        50                  55                  60 tcg cac ctg ctg cac ctg gcc gcg cac cca ctc gga ccc tcg atg tta    240
Ser His Leu Leu His Leu Ala Ala His Pro Leu Gly Pro Ser Met Leu
65                  70                  75                  80 cga ctg atc aat gaa atg gca cgt acc agc gat atg ctt tgc cgg gaa    288
Arg Leu Ile Asn Glu Met Ala Arg Thr Ser Asp Met Leu Cys Arg Glu
                85                  90                  95 ctg ccc gcc gct ttt cat gcg ttg cag ata gag ggc gtg atc gtt gat    336
Leu Pro Ala Ala Phe His Ala Leu Gln Ile Glu Gly Val Ile Val Asp
            100                 105                 110 caa atg gag ccg gca ggt gca gta gtc gca gaa gcg tca ggt ctg ccg    384
Gln Met Glu Pro Ala Gly Ala Val Val Ala Glu Ala Ser Gly Leu Pro
        115                 120                 125 ttt gtt tcg gtg gcc tgc gcg ctg ccg ctc aac cgc gaa ccg ggt ttg    432
Phe Val Ser Val Ala Cys Ala Leu Pro Leu Asn Arg Glu Pro Gly Leu
```

```
                      130                 135                 140
cct ctg gcg gtg atg cct ttc gag tac ggc acc agc gat gcg gct cgg       480
Pro Leu Ala Val Met Pro Phe Glu Tyr Gly Thr Ser Asp Ala Ala Arg
145                 150                 155                 160 gaa cgc tat acc acc agc gaa aaa att tat gac tgg ctg atg cga cgt       528
Glu Arg Tyr Thr Thr Ser Glu Lys Ile Tyr Asp Trp Leu Met Arg Arg
                165                 170                 175 cac gat cgt gtg atc gcg cat cat gca tgc aga atg ggt tta gcc ccg       576
His Asp Arg Val Ile Ala His His Ala Cys Arg Met Gly Leu Ala Pro
            180                 185                 190 cgt gaa aaa ctg cat cat tgt ttt tct cca ctg gca caa atc agc cag       624
Arg Glu Lys Leu His His Cys Phe Ser Pro Leu Ala Gln Ile Ser Gln
        195                 200                 205 ttg atc ccc gaa ctg gat ttt ccc cgc aaa gcg ctg cca gac tgc ttt       672
Leu Ile Pro Glu Leu Asp Phe Pro Arg Lys Ala Leu Pro Asp Cys Phe
    210                 215                 220 cat gcg gtt gga ccg tta cgg caa ccc cag ggg acg ccg ggg tca tca       720
His Ala Val Gly Pro Leu Arg Gln Pro Gln Gly Thr Pro Gly Ser Ser
225                 230                 235                 240 act tct tat ttt ccg tcc ccg gac aaa ccc cgt att ttt gcc tcg ctg       768
Thr Ser Tyr Phe Pro Ser Pro Asp Lys Pro Arg Ile Phe Ala Ser Leu
                245                 250                 255 ggc acc ctg cag gga cat cgt tat ggc ctg ttc agg acc atc gcc aaa       816
Gly Thr Leu Gln Gly His Arg Tyr Gly Leu Phe Arg Thr Ile Ala Lys
            260                 265                 270 gcc tgc gaa gag gtg gat gcg cag tta ctg ttg gca cac tgt ggc ggc       864
Ala Cys Glu Glu Val Asp Ala Gln Leu Leu Leu Ala His Cys Gly Gly
        275                 280                 285 ctc tca gcc acg cag gca ggt gaa ctg gcc cgg ggc ggg gac att cag       912
Leu Ser Ala Thr Gln Ala Gly Glu Leu Ala Arg Gly Gly Asp Ile Gln
    290                 295                 300 gtt gtg gat ttt gcc gat caa tcc gca gca ctt tca cag gca cag ttg       960
Val Val Asp Phe Ala Asp Gln Ser Ala Ala Leu Ser Gln Ala Gln Leu
305                 310                 315                 320 aca atc aca cat ggt ggg atg aat acg gta ctg gac gct att gct tcc      1008
Thr Ile Thr His Gly Gly Met Asn Thr Val Leu Asp Ala Ile Ala Ser
                325                 330                 335 cgc aca ccg cta ctg gcg ctg ccg ctg gca ttt gat caa cct ggc gtg      1056
Arg Thr Pro Leu Leu Ala Leu Pro Leu Ala Phe Asp Gln Pro Gly Val
            340                 345                 350 gca tca cga att gtt tat cat ggc atc ggc aag cgt gcg tct cgg ttt      1104
Ala Ser Arg Ile Val Tyr His Gly Ile Gly Lys Arg Ala Ser Arg Phe
        355                 360                 365 act acc agc cat gcg ctg gcg cgg cag att cga tcg ctg ctg act aac      1152
Thr Thr Ser His Ala Leu Ala Arg Gln Ile Arg Ser Leu Leu Thr Asn
    370                 375                 380 acc gat tac ccg cag cgt atg aca aaa att cag gcc gca ttg cgt ctg      1200
Thr Asp Tyr Pro Gln Arg Met Thr Lys Ile Gln Ala Ala Leu Arg Leu
385                 390                 395                 400 gca ggc ggc aca cca gcc gcc gcc gat att gtt gaa cag gcg atg cgg      1248
Ala Gly Gly Thr Pro Ala Ala Ala Asp Ile Val Glu Gln Ala Met Arg
                405                 410                 415 acc tgt cag cca gta ctc agt ggg cag gat tat gca acc gca cta tga      1296
Thr Cys Gln Pro Val Leu Ser Gly Gln Asp Tyr Ala Thr Ala Leu
            420                 425                 430
```

<210> SEQ ID NO 4
<211> LENGTH: 431
<212> TYPE: PRT
<213> ORGANISM: Pantoea stewartii

<400> SEQUENCE: 4

```
Met Ser His Phe Ala Val Ile Ala Pro Pro Phe Ser His Val Arg
1               5                   10                  15

Ala Leu Gln Asn Leu Ala Gln Glu Leu Val Ala Arg Gly His Arg Val
                20                  25                  30

Thr Phe Phe Gln Gln His Asp Cys Lys Ala Leu Val Thr Gly Ser Asp
            35                  40                  45

Ile Gly Phe Gln Thr Val Gly Leu Gln Thr His Pro Pro Gly Ser Leu
        50                  55                  60

Ser His Leu Leu His Leu Ala Ala His Pro Leu Gly Pro Ser Met Leu
65                  70                  75                  80

Arg Leu Ile Asn Glu Met Ala Arg Thr Ser Asp Met Leu Cys Arg Glu
                85                  90                  95

Leu Pro Ala Ala Phe His Ala Leu Gln Ile Glu Gly Val Ile Val Asp
            100                 105                 110

Gln Met Glu Pro Ala Gly Ala Val Ala Glu Ala Ser Gly Leu Pro
        115                 120                 125

Phe Val Ser Val Ala Cys Ala Leu Pro Leu Asn Arg Glu Pro Gly Leu
130                 135                 140

Pro Leu Ala Val Met Pro Phe Glu Tyr Gly Thr Ser Asp Ala Ala Arg
145                 150                 155                 160

Glu Arg Tyr Thr Thr Ser Glu Lys Ile Tyr Asp Trp Leu Met Arg Arg
                165                 170                 175

His Asp Arg Val Ile Ala His Ala Cys Arg Met Gly Leu Ala Pro
            180                 185                 190

Arg Glu Lys Leu His His Cys Phe Ser Pro Leu Ala Gln Ile Ser Gln
        195                 200                 205

Leu Ile Pro Glu Leu Asp Phe Pro Arg Lys Ala Leu Pro Asp Cys Phe
210                 215                 220

His Ala Val Gly Pro Leu Arg Gln Pro Gln Gly Thr Pro Gly Ser Ser
225                 230                 235                 240

Thr Ser Tyr Phe Pro Ser Pro Asp Lys Pro Arg Ile Phe Ala Ser Leu
                245                 250                 255

Gly Thr Leu Gln Gly His Arg Tyr Gly Leu Phe Arg Thr Ile Ala Lys
            260                 265                 270

Ala Cys Glu Glu Val Asp Ala Gln Leu Leu Ala His Cys Gly Gly
        275                 280                 285

Leu Ser Ala Thr Gln Ala Gly Glu Leu Ala Arg Gly Gly Asp Ile Gln
290                 295                 300

Val Val Asp Phe Ala Asp Gln Ser Ala Ala Leu Ser Gln Ala Gln Leu
305                 310                 315                 320

Thr Ile Thr His Gly Gly Met Asn Thr Val Leu Asp Ala Ile Ala Ser
                325                 330                 335

Arg Thr Pro Leu Leu Ala Leu Pro Leu Ala Phe Asp Gln Pro Gly Val
            340                 345                 350

Ala Ser Arg Ile Val Tyr His Gly Ile Gly Lys Arg Ala Ser Arg Phe
        355                 360                 365

Thr Thr Ser His Ala Leu Ala Arg Gln Ile Arg Ser Leu Leu Thr Asn
370                 375                 380

Thr Asp Tyr Pro Gln Arg Met Thr Lys Ile Gln Ala Ala Leu Arg Leu
385                 390                 395                 400

Ala Gly Gly Thr Pro Ala Ala Ala Asp Ile Val Glu Gln Ala Met Arg
```

```
                    405                 410                 415
Thr Cys Gln Pro Val Leu Ser Gly Gln Asp Tyr Ala Thr Ala Leu
            420                 425                 430

<210> SEQ ID NO 5
<211> LENGTH: 1149
<212> TYPE: DNA
<213> ORGANISM: Pantoea stewartii
<220> FEATURE:
<221> NAME/KEY: CDS
<222> LOCATION: (1)..(1149)

<400> SEQUENCE: 5 atg caa ccg cac tat gat ctc att ctg gtc ggt gcc ggt ctg gct aat     48
Met Gln Pro His Tyr Asp Leu Ile Leu Val Gly Ala Gly Leu Ala Asn
1               5                   10                  15 ggc ctt atc gcg ctc cgg ctt cag caa cag cat ccg gat atg cgg atc     96
Gly Leu Ile Ala Leu Arg Leu Gln Gln Gln His Pro Asp Met Arg Ile
            20                  25                  30 ttg ctt att gag gcg ggt cct gag gcg gga ggg aac cat acc tgg tcc    144
Leu Leu Ile Glu Ala Gly Pro Glu Ala Gly Gly Asn His Thr Trp Ser
        35                  40                  45 ttt cac gaa gag gat tta acg ctg aat cag cat cgc tgg ata gcg ccg    192
Phe His Glu Glu Asp Leu Thr Leu Asn Gln His Arg Trp Ile Ala Pro
    50                  55                  60 ctt gtg gtc cat cac tgg ccc gac tac cag gtt cgt ttc ccc caa cgc    240
Leu Val Val His His Trp Pro Asp Tyr Gln Val Arg Phe Pro Gln Arg
65                  70                  75                  80 cgt cgc cat gtg aac agt ggc tac tac tgc gtg acc tcc cgg cat ttc    288
Arg Arg His Val Asn Ser Gly Tyr Tyr Cys Val Thr Ser Arg His Phe
                85                  90                  95 gcc ggg ata ctc cgg caa cag ttt gga caa cat tta tgg ctg cat acc    336
Ala Gly Ile Leu Arg Gln Gln Phe Gly Gln His Leu Trp Leu His Thr
            100                 105                 110 gcg gtt tca gcc gtt cat gct gaa tcg gtc cag tta gcg gat ggc cgg    384
Ala Val Ser Ala Val His Ala Glu Ser Val Gln Leu Ala Asp Gly Arg
        115                 120                 125 att att cat gcc agt aca gtg atc gac gga cgg ggt tac acg cct gat    432
Ile Ile His Ala Ser Thr Val Ile Asp Gly Arg Gly Tyr Thr Pro Asp
    130                 135                 140 tct gca cta cgc gta gga ttc cag gca ttt atc ggt cag gag tgg caa    480
Ser Ala Leu Arg Val Gly Phe Gln Ala Phe Ile Gly Gln Glu Trp Gln
145                 150                 155                 160 ctg agc gcg ccg cat ggt tta tcg tca ccg att atc atg gat gcg acg    528
Leu Ser Ala Pro His Gly Leu Ser Ser Pro Ile Ile Met Asp Ala Thr
                165                 170                 175 gtc gat cag caa aat ggc tac cgc ttt gtt tat acc ctg ccg ctt tcc    576
Val Asp Gln Gln Asn Gly Tyr Arg Phe Val Tyr Thr Leu Pro Leu Ser
            180                 185                 190 gca acc gca ctg ctg atc gaa gac aca cac tac att gac aag gct aat    624
Ala Thr Ala Leu Leu Ile Glu Asp Thr His Tyr Ile Asp Lys Ala Asn
        195                 200                 205 ctt cag gcc gaa cgg gcg cgt cag aac att cgc gat tat gct gcg cga    672
Leu Gln Ala Glu Arg Ala Arg Gln Asn Ile Arg Asp Tyr Ala Ala Arg
    210                 215                 220 cag ggt tgg ccg tta cag acg ttg ctg cgg gaa gaa cag ggt gca ttg    720
Gln Gly Trp Pro Leu Gln Thr Leu Leu Arg Glu Glu Gln Gly Ala Leu
225                 230                 235                 240 ccc att acg tta acg ggc gat aat cgt cag ttt tgg caa cag caa ccg    768
Pro Ile Thr Leu Thr Gly Asp Asn Arg Gln Phe Trp Gln Gln Gln Pro
                245                 250                 255
```

-continued

```
caa gcc tgt agc gga tta cgc gcc ggg ctg ttt cat ccg aca acc ggc        816
Gln Ala Cys Ser Gly Leu Arg Ala Gly Leu Phe His Pro Thr Thr Gly
        260                 265                 270 tac tcc cta ccg ctc gcg gtg gcg ctg gcc gat cgt ctc agc gcg ctg        864
Tyr Ser Leu Pro Leu Ala Val Ala Leu Ala Asp Arg Leu Ser Ala Leu
    275                 280                 285 gat gtg ttt acc tct tcc tct gtt cac cag acg att gct cac ttt gcc        912
Asp Val Phe Thr Ser Ser Ser Val His Gln Thr Ile Ala His Phe Ala
290                 295                 300 cag caa cgt tgg cag caa cag ggg ttt ttc cgc atg ctg aat cgc atg        960
Gln Gln Arg Trp Gln Gln Gln Gly Phe Phe Arg Met Leu Asn Arg Met
305                 310                 315                 320 ttg ttt tta gcc gga ccg gcc gag tca cgc tgg cgt gtg atg cag cgt       1008
Leu Phe Leu Ala Gly Pro Ala Glu Ser Arg Trp Arg Val Met Gln Arg
                325                 330                 335 ttc tat ggc tta ccc gag gat ttg att gcc cgc ttt tat gcg gga aaa       1056
Phe Tyr Gly Leu Pro Glu Asp Leu Ile Ala Arg Phe Tyr Ala Gly Lys
            340                 345                 350 ctc acc gtg acc gat cgg cta cgc att ctg agc ggc aag ccg ccc gtt       1104
Leu Thr Val Thr Asp Arg Leu Arg Ile Leu Ser Gly Lys Pro Pro Val
        355                 360                 365 ccc gtt ttc gcg gca ttg cag gca att atg acg act cat cgt tga           1149
Pro Val Phe Ala Ala Leu Gln Ala Ile Met Thr Thr His Arg
    370                 375                 380

<210> SEQ ID NO 6
<211> LENGTH: 382
<212> TYPE: PRT
<213> ORGANISM: Pantoea stewartii

<400> SEQUENCE: 6

Met Gln Pro His Tyr Asp Leu Ile Leu Val Gly Ala Gly Leu Ala Asn
1               5                   10                  15

Gly Leu Ile Ala Leu Arg Leu Gln Gln Gln His Pro Asp Met Arg Ile
            20                  25                  30

Leu Leu Ile Glu Ala Gly Pro Glu Ala Gly Gly Asn His Thr Trp Ser
        35                  40                  45

Phe His Glu Glu Asp Leu Thr Leu Asn Gln His Arg Trp Ile Ala Pro
    50                  55                  60

Leu Val Val His His Trp Pro Asp Tyr Gln Val Arg Phe Pro Gln Arg
65                  70                  75                  80

Arg Arg His Val Asn Ser Gly Tyr Tyr Cys Val Thr Ser Arg His Phe
                85                  90                  95

Ala Gly Ile Leu Arg Gln Gln Phe Gly Gln His Leu Trp Leu His Thr
            100                 105                 110

Ala Val Ser Ala Val His Ala Glu Ser Val Gln Leu Ala Asp Gly Arg
        115                 120                 125

Ile Ile His Ala Ser Thr Val Ile Asp Gly Arg Gly Tyr Thr Pro Asp
    130                 135                 140

Ser Ala Leu Arg Val Gly Phe Gln Ala Phe Ile Gly Gln Glu Trp Gln
145                 150                 155                 160

Leu Ser Ala Pro His Gly Leu Ser Ser Pro Ile Ile Met Asp Ala Thr
                165                 170                 175

Val Asp Gln Gln Asn Gly Tyr Arg Phe Val Tyr Thr Leu Pro Leu Ser
            180                 185                 190

Ala Thr Ala Leu Leu Ile Glu Asp Thr His Tyr Ile Asp Lys Ala Asn
        195                 200                 205
```

```
Leu Gln Ala Glu Arg Ala Arg Gln Asn Ile Arg Asp Tyr Ala Ala Arg
    210                 215                 220

Gln Gly Trp Pro Leu Gln Thr Leu Leu Arg Glu Gln Gly Ala Leu
225                 230                 235                 240

Pro Ile Thr Leu Thr Gly Asp Asn Arg Gln Phe Trp Gln Gln Pro
                245                 250                 255

Gln Ala Cys Ser Gly Leu Arg Ala Gly Leu Phe His Pro Thr Thr Gly
        260                 265                 270

Tyr Ser Leu Pro Leu Ala Val Ala Leu Ala Asp Arg Leu Ser Ala Leu
        275                 280                 285

Asp Val Phe Thr Ser Ser Val His Gln Thr Ile Ala His Phe Ala
    290                 295                 300

Gln Gln Arg Trp Gln Gln Gly Phe Phe Arg Met Leu Asn Arg Met
305                 310                 315                 320

Leu Phe Leu Ala Gly Pro Ala Glu Ser Arg Trp Arg Val Met Gln Arg
                325                 330                 335

Phe Tyr Gly Leu Pro Glu Asp Leu Ile Ala Arg Phe Tyr Ala Gly Lys
                340                 345                 350

Leu Thr Val Thr Asp Arg Leu Arg Ile Leu Ser Gly Lys Pro Pro Val
            355                 360                 365

Pro Val Phe Ala Ala Leu Gln Ala Ile Met Thr Thr His Arg
        370                 375                 380

<210> SEQ ID NO 7
<211> LENGTH: 1479
<212> TYPE: DNA
<213> ORGANISM: Pantoea stewartii
<220> FEATURE:
<221> NAME/KEY: CDS
<222> LOCATION: (1)..(1479)

<400> SEQUENCE: 7 atg aaa cca act acg gta att ggt gcg ggc ttt ggt ggc ctg gca ctg      48
Met Lys Pro Thr Thr Val Ile Gly Ala Gly Phe Gly Gly Leu Ala Leu
1               5                   10                  15 gca att cgt tta cag gcc gca ggt att cct gtt ttg ctg ctt gag cag      96
Ala Ile Arg Leu Gln Ala Ala Gly Ile Pro Val Leu Leu Leu Glu Gln
            20                  25                  30 cgc gac aag ccg ggt ggc cgg gct tat gtt tat cag gag cag ggc ttt     144
Arg Asp Lys Pro Gly Gly Arg Ala Tyr Val Tyr Gln Glu Gln Gly Phe
        35                  40                  45 act ttt gat gca ggc cct acc gtt atc acc gat ccc agc gcg att gaa     192
Thr Phe Asp Ala Gly Pro Thr Val Ile Thr Asp Pro Ser Ala Ile Glu
    50                  55                  60 gaa ctg ttt gct ctg gcc ggt aaa cag ctt aag gat tac gtc gag ctg     240
Glu Leu Phe Ala Leu Ala Gly Lys Gln Leu Lys Asp Tyr Val Glu Leu
65                  70                  75                  80 ttg ccg gtc acg ccg ttt tat cgc ctg tgc tgg gag tcc ggc aag gtc     288
Leu Pro Val Thr Pro Phe Tyr Arg Leu Cys Trp Glu Ser Gly Lys Val
                85                  90                  95 ttc aat tac gat aac gac cag gcc cag tta gaa gcg cag ata cag cag     336
Phe Asn Tyr Asp Asn Asp Gln Ala Gln Leu Glu Ala Gln Ile Gln Gln
            100                 105                 110 ttt aat ccg cgc gat gtt gcg ggt tat cga gcg ttc ctt gac tat tcg     384
Phe Asn Pro Arg Asp Val Ala Gly Tyr Arg Ala Phe Leu Asp Tyr Ser
        115                 120                 125 cgt gcc gta ttc aat gag ggc tat ctg aag ctc ggc act gtg cct ttt     432
Arg Ala Val Phe Asn Glu Gly Tyr Leu Lys Leu Gly Thr Val Pro Phe
```

```
                130                 135                 140
tta tcg ttc aaa gac atg ctt cgg gcc gcg ccc cag ttg gca aag ctg      480
Leu Ser Phe Lys Asp Met Leu Arg Ala Ala Pro Gln Leu Ala Lys Leu
145                 150                 155                 160 cag gca tgg cgc agc gtt tac agt aaa gtt gcc ggc tac att gag gat      528
Gln Ala Trp Arg Ser Val Tyr Ser Lys Val Ala Gly Tyr Ile Glu Asp
                165                 170                 175 gag cat ctt cgg cag gcg ttt tct ttt cac tcg ctc tta gtg ggg ggg      576
Glu His Leu Arg Gln Ala Phe Ser Phe His Ser Leu Leu Val Gly Gly
            180                 185                 190 aat ccg ttt gca acc tcg tcc att tat acg ctg att cac gcg tta gaa      624
Asn Pro Phe Ala Thr Ser Ser Ile Tyr Thr Leu Ile His Ala Leu Glu
        195                 200                 205 cgg gaa tgg ggc gtc tgg ttt cca cgc ggt gga acc ggt gcg ctg gtc      672
Arg Glu Trp Gly Val Trp Phe Pro Arg Gly Gly Thr Gly Ala Leu Val
    210                 215                 220 aat ggc atg atc aag ctg ttt cag gat ctg ggc ggc gaa gtc gtg ctt      720
Asn Gly Met Ile Lys Leu Phe Gln Asp Leu Gly Gly Glu Val Val Leu
225                 230                 235                 240 aac gcc cgg gtc agt cat atg gaa acc gtt ggg gac aag att cag gcc      768
Asn Ala Arg Val Ser His Met Glu Thr Val Gly Asp Lys Ile Gln Ala
                245                 250                 255 gtg cag ttg gaa gac ggc aga cgg ttt gaa acc tgc gcg gtg gcg tcg      816
Val Gln Leu Glu Asp Gly Arg Arg Phe Glu Thr Cys Ala Val Ala Ser
            260                 265                 270 aac gct gat gtt gta cat acc tat cgc gat ctg ctg tct cag cat ccc      864
Asn Ala Asp Val Val His Thr Tyr Arg Asp Leu Leu Ser Gln His Pro
        275                 280                 285 gca gcc gct aag cag gcg aaa aaa ctg caa tcc aag cgt atg agt aac      912
Ala Ala Ala Lys Gln Ala Lys Lys Leu Gln Ser Lys Arg Met Ser Asn
    290                 295                 300 tca ctg ttt gta ctc tat ttt ggt ctc aac cat cac gat caa ctc          960
Ser Leu Phe Val Leu Tyr Phe Gly Leu Asn His His Asp Gln Leu
305                 310                 315                 320 gcc cat cat acc gtc tgt ttt ggg cca cgc tac cgt gaa ctg att cac     1008
Ala His His Thr Val Cys Phe Gly Pro Arg Tyr Arg Glu Leu Ile His
                325                 330                 335 gaa att ttt aac cat gat ggt ctg gct gag gat ttt tcg ctt tat tta     1056
Glu Ile Phe Asn His Asp Gly Leu Ala Glu Asp Phe Ser Leu Tyr Leu
            340                 345                 350 cac gca cct tgt gtc acg gat ccg tca ctg gca ccg gaa ggg tgc ggc     1104
His Ala Pro Cys Val Thr Asp Pro Ser Leu Ala Pro Glu Gly Cys Gly
        355                 360                 365 agc tat tat gtg ctg gcg cct gtt cca cac tta ggc acg gcg aac ctc     1152
Ser Tyr Tyr Val Leu Ala Pro Val Pro His Leu Gly Thr Ala Asn Leu
    370                 375                 380 gac tgg gcg gta gaa gga ccc cga ctg cgc gat cgt att ttt gac tac     1200
Asp Trp Ala Val Glu Gly Pro Arg Leu Arg Asp Arg Ile Phe Asp Tyr
385                 390                 395                 400 ctt gag caa cat tac atg cct ggc ttg cga agc cag ttg gtg acg cac     1248
Leu Glu Gln His Tyr Met Pro Gly Leu Arg Ser Gln Leu Val Thr His
                405                 410                 415 cgt atg ttt acg ccg ttc gat ttc cgc gac gag ctc aat gcc tgg caa     1296
Arg Met Phe Thr Pro Phe Asp Phe Arg Asp Glu Leu Asn Ala Trp Gln
            420                 425                 430 ggt tcg gcc ttc tcg gtt gaa cct att ctg acc cag agc gcc tgg ttc     1344
Gly Ser Ala Phe Ser Val Glu Pro Ile Leu Thr Gln Ser Ala Trp Phe
        435                 440                 445 cga cca cat aac cgc gat aag cac att gat aat ctt tat ctg gtt ggc     1392
Arg Pro His Asn Arg Asp Lys His Ile Asp Asn Leu Tyr Leu Val Gly
```

```
Arg Pro His Asn Arg Asp Lys His Ile Asp Asn Leu Tyr Leu Val Gly
    450                 455                 460 gca ggc acc cat cct ggc gcg ggc att ccc ggc gta atc ggc tcg gcg    1440
Ala Gly Thr His Pro Gly Ala Gly Ile Pro Gly Val Ile Gly Ser Ala
465                 470                 475                 480 aag gcg acg gca ggc tta atg ctg gag gac ctg att tga                1479
Lys Ala Thr Ala Gly Leu Met Leu Glu Asp Leu Ile
                485                 490

<210> SEQ ID NO 8
<211> LENGTH: 492
<212> TYPE: PRT
<213> ORGANISM: Pantoea stewartii

<400> SEQUENCE: 8

Met Lys Pro Thr Thr Val Ile Gly Ala Gly Phe Gly Gly Leu Ala Leu
1               5                   10                  15

Ala Ile Arg Leu Gln Ala Ala Gly Ile Pro Val Leu Leu Leu Glu Gln
                20                  25                  30

Arg Asp Lys Pro Gly Gly Arg Ala Tyr Val Tyr Gln Glu Gln Gly Phe
            35                  40                  45

Thr Phe Asp Ala Gly Pro Thr Val Ile Thr Asp Pro Ser Ala Ile Glu
        50                  55                  60

Glu Leu Phe Ala Leu Ala Gly Lys Gln Leu Lys Asp Tyr Val Glu Leu
65                  70                  75                  80

Leu Pro Val Thr Pro Phe Tyr Arg Leu Cys Trp Glu Ser Gly Lys Val
                85                  90                  95

Phe Asn Tyr Asp Asn Asp Gln Ala Gln Leu Glu Ala Gln Ile Gln Gln
            100                 105                 110

Phe Asn Pro Arg Asp Val Ala Gly Tyr Arg Ala Phe Leu Asp Tyr Ser
        115                 120                 125

Arg Ala Val Phe Asn Glu Gly Tyr Leu Lys Leu Gly Thr Val Pro Phe
130                 135                 140

Leu Ser Phe Lys Asp Met Leu Arg Ala Ala Pro Gln Leu Ala Lys Leu
145                 150                 155                 160

Gln Ala Trp Arg Ser Val Tyr Ser Lys Val Ala Gly Tyr Ile Glu Asp
                165                 170                 175

Glu His Leu Arg Gln Ala Phe Ser Phe His Ser Leu Leu Val Gly Gly
            180                 185                 190

Asn Pro Phe Ala Thr Ser Ser Ile Tyr Thr Leu Ile His Ala Leu Glu
        195                 200                 205

Arg Glu Trp Gly Val Trp Phe Pro Arg Gly Gly Thr Gly Ala Leu Val
210                 215                 220

Asn Gly Met Ile Lys Leu Phe Gln Asp Leu Gly Gly Glu Val Val Leu
225                 230                 235                 240

Asn Ala Arg Val Ser His Met Glu Thr Val Gly Asp Lys Ile Gln Ala
                245                 250                 255

Val Gln Leu Glu Asp Gly Arg Arg Phe Glu Thr Cys Ala Val Ala Ser
            260                 265                 270

Asn Ala Asp Val Val His Thr Tyr Arg Asp Leu Leu Ser Gln His Pro
        275                 280                 285

Ala Ala Ala Lys Gln Ala Lys Lys Leu Gln Ser Lys Arg Met Ser Asn
290                 295                 300

Ser Leu Phe Val Leu Tyr Phe Gly Leu Asn His His Asp Gln Leu
305                 310                 315                 320
```

```
Ala His His Thr Val Cys Phe Gly Pro Arg Tyr Arg Glu Leu Ile His
            325                 330                 335

Glu Ile Phe Asn His Asp Gly Leu Ala Glu Asp Phe Ser Leu Tyr Leu
                340                 345                 350

His Ala Pro Cys Val Thr Asp Pro Ser Leu Ala Pro Glu Gly Cys Gly
            355                 360                 365

Ser Tyr Tyr Val Leu Ala Pro Val Pro His Leu Gly Thr Ala Asn Leu
    370                 375                 380

Asp Trp Ala Val Glu Gly Pro Arg Leu Arg Asp Arg Ile Phe Asp Tyr
385                 390                 395                 400

Leu Glu Gln His Tyr Met Pro Gly Leu Arg Ser Gln Leu Val Thr His
                405                 410                 415

Arg Met Phe Thr Pro Phe Asp Phe Arg Asp Glu Leu Asn Ala Trp Gln
            420                 425                 430

Gly Ser Ala Phe Ser Val Glu Pro Ile Leu Thr Gln Ser Ala Trp Phe
            435                 440                 445

Arg Pro His Asn Arg Asp Lys His Ile Asp Asn Leu Tyr Leu Val Gly
        450                 455                 460

Ala Gly Thr His Pro Gly Ala Gly Ile Pro Gly Val Ile Gly Ser Ala
465                 470                 475                 480

Lys Ala Thr Ala Gly Leu Met Leu Glu Asp Leu Ile
                485                 490
```

<210> SEQ ID NO 9
<211> LENGTH: 891
<212> TYPE: DNA
<213> ORGANISM: Pantoea stewartii
<220> FEATURE:
<221> NAME/KEY: CDS
<222> LOCATION: (1)..(891)

<400> SEQUENCE: 9

```
atg gcg gtt ggc tcg aaa agc ttt gcg act gca tcg acg ctt ttc gac      48
Met Ala Val Gly Ser Lys Ser Phe Ala Thr Ala Ser Thr Leu Phe Asp
1               5                   10                  15 gcc aaa acc cgt cgc agc gtg ctg atg ctt tac gca tgg tgc cgc cac      96
Ala Lys Thr Arg Arg Ser Val Leu Met Leu Tyr Ala Trp Cys Arg His
                20                  25                  30 tgc gac gac gtc att gac gat caa aca ctg ggc ttt cat gcc gac cag     144
Cys Asp Asp Val Ile Asp Asp Gln Thr Leu Gly Phe His Ala Asp Gln
            35                  40                  45 ccc tct tcg cag atg cct gag cag cgc ctg cag cag ctt gaa atg aaa     192
Pro Ser Ser Gln Met Pro Glu Gln Arg Leu Gln Gln Leu Glu Met Lys
        50                  55                  60 acg cgt cag gcc tac gcc ggt tcg caa atg cac gag ccc gct ttt gcc     240
Thr Arg Gln Ala Tyr Ala Gly Ser Gln Met His Glu Pro Ala Phe Ala
65                  70                  75                  80 gcg ttt cag gag gtc gcg atg gcg cat gat atc gct ccc gcc tac gcg     288
Ala Phe Gln Glu Val Ala Met Ala His Asp Ile Ala Pro Ala Tyr Ala
                85                  90                  95 ttc gac cat ctg gaa ggt ttt gcc atg gat gtg cgc gaa acg cgc tac     336
Phe Asp His Leu Glu Gly Phe Ala Met Asp Val Arg Glu Thr Arg Tyr
                100                 105                 110 ctg aca ctg gac gat acg ctg cgt tat tgc tat cac gtc gcc ggt gtt     384
Leu Thr Leu Asp Asp Thr Leu Arg Tyr Cys Tyr His Val Ala Gly Val
            115                 120                 125 gtg ggc ctg atg atg gcg caa att atg ggc gtt cgc gat aac gcc acg     432
Val Gly Leu Met Met Ala Gln Ile Met Gly Val Arg Asp Asn Ala Thr
        130                 135                 140
```

```
ctc gat cgc gcc tgc gat ctc ggg ctg gct ttc cag ttg acc aac att     480
Leu Asp Arg Ala Cys Asp Leu Gly Leu Ala Phe Gln Leu Thr Asn Ile
145                 150                 155                 160 gcg cgt gat att gtc gac gat gct cag gtg ggc cgc tgt tat ctg cct     528
Ala Arg Asp Ile Val Asp Asp Ala Gln Val Gly Arg Cys Tyr Leu Pro
                165                 170                 175 gaa agc tgg ctg gaa gag gaa gga ctg acg aaa gcg aat tat gct gcg     576
Glu Ser Trp Leu Glu Glu Glu Gly Leu Thr Lys Ala Asn Tyr Ala Ala
            180                 185                 190 cca gaa aac cgg cag gcc tta agc cgt atc gcc ggg cga ctg gta cgg     624
Pro Glu Asn Arg Gln Ala Leu Ser Arg Ile Ala Gly Arg Leu Val Arg
        195                 200                 205 gaa gcg gaa ccc tat tac gta tca tca atg gcc ggt ctg gca caa tta     672
Glu Ala Glu Pro Tyr Tyr Val Ser Ser Met Ala Gly Leu Ala Gln Leu
    210                 215                 220 ccc tta cgc tcg gcc tgg gcc atc gcg aca gcg aag cag gta tac cgt     720
Pro Leu Arg Ser Ala Trp Ala Ile Ala Thr Ala Lys Gln Val Tyr Arg
225                 230                 235                 240 aaa att ggc gtg aaa gtt gaa cag gcc ggt aag cag gcc tgg gat cat     768
Lys Ile Gly Val Lys Val Glu Gln Ala Gly Lys Gln Ala Trp Asp His
                245                 250                 255 cgc cag tcc acg tcc acc gcc gaa aaa tta acg ctt ttg ctg acg gca     816
Arg Gln Ser Thr Ser Thr Ala Glu Lys Leu Thr Leu Leu Leu Thr Ala
            260                 265                 270 tcc ggt cag gca gtt act tcc cgg atg aag acg tat cca ccc cgt cct     864
Ser Gly Gln Ala Val Thr Ser Arg Met Lys Thr Tyr Pro Pro Arg Pro
        275                 280                 285 gct cat ctc tgg cag cgc ccg atc tag                                 891
Ala His Leu Trp Gln Arg Pro Ile
    290                 295
```

<210> SEQ ID NO 10
<211> LENGTH: 296
<212> TYPE: PRT
<213> ORGANISM: Pantoea stewartii

<400> SEQUENCE: 10

```
Met Ala Val Gly Ser Lys Ser Phe Ala Thr Ala Ser Thr Leu Phe Asp
1               5                   10                  15

Ala Lys Thr Arg Arg Ser Val Leu Met Leu Tyr Ala Trp Cys Arg His
                20                  25                  30

Cys Asp Asp Val Ile Asp Asp Gln Thr Leu Gly Phe His Ala Asp Gln
            35                  40                  45

Pro Ser Ser Gln Met Pro Glu Gln Arg Leu Gln Gln Leu Glu Met Lys
        50                  55                  60

Thr Arg Gln Ala Tyr Ala Gly Ser Gln Met His Glu Pro Ala Phe Ala
65                  70                  75                  80

Ala Phe Gln Glu Val Ala Met Ala His Asp Ile Ala Pro Ala Tyr Ala
                85                  90                  95

Phe Asp His Leu Glu Gly Phe Ala Met Asp Val Arg Glu Thr Arg Tyr
            100                 105                 110

Leu Thr Leu Asp Asp Thr Leu Arg Tyr Cys Tyr His Val Ala Gly Val
        115                 120                 125

Val Gly Leu Met Met Ala Gln Ile Met Gly Val Arg Asp Asn Ala Thr
130                 135                 140

Leu Asp Arg Ala Cys Asp Leu Gly Leu Ala Phe Gln Leu Thr Asn Ile
145                 150                 155                 160
```

```
Ala Arg Asp Ile Val Asp Asp Ala Gln Val Gly Arg Cys Tyr Leu Pro
            165                 170                 175

Glu Ser Trp Leu Glu Glu Gly Leu Thr Lys Ala Asn Tyr Ala Ala
            180                 185                 190

Pro Glu Asn Arg Gln Ala Leu Ser Arg Ile Ala Gly Arg Leu Val Arg
            195                 200                 205

Glu Ala Glu Pro Tyr Tyr Val Ser Ser Met Ala Gly Leu Ala Gln Leu
210                 215                 220

Pro Leu Arg Ser Ala Trp Ala Ile Ala Thr Ala Lys Gln Val Tyr Arg
225                 230                 235                 240

Lys Ile Gly Val Lys Val Glu Gln Ala Gly Lys Gln Ala Trp Asp His
            245                 250                 255

Arg Gln Ser Thr Ser Thr Ala Glu Lys Leu Thr Leu Leu Thr Ala
            260                 265                 270

Ser Gly Gln Ala Val Thr Ser Arg Met Lys Thr Tyr Pro Pro Arg Pro
            275                 280                 285

Ala His Leu Trp Gln Arg Pro Ile
            290                 295

<210> SEQ ID NO 11
<211> LENGTH: 528
<212> TYPE: DNA
<213> ORGANISM: Pantoea stewartii
<220> FEATURE:
<221> NAME/KEY: CDS
<222> LOCATION: (1)..(528)

<400> SEQUENCE: 11 atg ttg tgg att tgg aat gcc ctg atc gtg ttt gtc acc gtg gtc ggc       48
Met Leu Trp Ile Trp Asn Ala Leu Ile Val Phe Val Thr Val Val Gly
1               5                   10                  15 atg gaa gtg gtt gct gca ctg gca cat aaa tac atc atg cac ggc tgg       96
Met Glu Val Val Ala Ala Leu Ala His Lys Tyr Ile Met His Gly Trp
            20                  25                  30 ggt tgg ggc tgg cat ctt tca cat cat gaa ccg cgt aaa ggc gca ttt      144
Gly Trp Gly Trp His Leu Ser His His Glu Pro Arg Lys Gly Ala Phe
        35                  40                  45 gaa gtt aac gat ctc tat gcc gtg gta ttc gcc att gtg tcg att gcc      192
Glu Val Asn Asp Leu Tyr Ala Val Val Phe Ala Ile Val Ser Ile Ala
    50                  55                  60 ctg att tac ttc ggc agt aca gga atc tgg ccg ctc cag tgg att ggt      240
Leu Ile Tyr Phe Gly Ser Thr Gly Ile Trp Pro Leu Gln Trp Ile Gly
65                  70                  75                  80 gca ggc atg acc gct tat ggt tta ctg tat ttt atg gtc cac gac gga      288
Ala Gly Met Thr Ala Tyr Gly Leu Leu Tyr Phe Met Val His Asp Gly
                85                  90                  95 ctg gta cac cag cgc tgg ccg ttc cgc tac ata ccg cgc aaa ggc tac      336
Leu Val His Gln Arg Trp Pro Phe Arg Tyr Ile Pro Arg Lys Gly Tyr
            100                 105                 110 ctg aaa cgg tta tac atg gcc cac cgt atg cat cat gct gta agg gga      384
Leu Lys Arg Leu Tyr Met Ala His Arg Met His His Ala Val Arg Gly
        115                 120                 125 aaa gag ggc tgc gtg tcc ttt ggt ttt ctg tac gcg cca ccg tta tct      432
Lys Glu Gly Cys Val Ser Phe Gly Phe Leu Tyr Ala Pro Pro Leu Ser
    130                 135                 140 aaa ctt cag gcg acg ctg aga gaa agg cat gcg gct aga tcg ggc gct      480
Lys Leu Gln Ala Thr Leu Arg Glu Arg His Ala Ala Arg Ser Gly Ala
145                 150                 155                 160 gcc aga gat gag cag gac ggg gtg gat acg tct tca tcc ggg aag taa      528
Ala Arg Asp Glu Gln Asp Gly Val Asp Thr Ser Ser Ser Gly Lys
                165                 170                 175
```

-continued

```
Ala Arg Asp Glu Gln Asp Gly Val Asp Thr Ser Ser Ser Gly Lys
            165                 170                 175

<210> SEQ ID NO 12
<211> LENGTH: 175
<212> TYPE: PRT
<213> ORGANISM: Pantoea stewartii

<400> SEQUENCE: 12

Met Leu Trp Ile Trp Asn Ala Leu Ile Val Phe Val Thr Val Val Gly
1               5                   10                  15

Met Glu Val Val Ala Ala Leu Ala His Lys Tyr Ile Met His Gly Trp
            20                  25                  30

Gly Trp Gly Trp His Leu Ser His His Glu Pro Arg Lys Gly Ala Phe
        35                  40                  45

Glu Val Asn Asp Leu Tyr Ala Val Val Phe Ala Ile Val Ser Ile Ala
    50                  55                  60

Leu Ile Tyr Phe Gly Ser Thr Gly Ile Trp Pro Leu Gln Trp Ile Gly
65                  70                  75                  80

Ala Gly Met Thr Ala Tyr Gly Leu Leu Tyr Phe Met Val His Asp Gly
                85                  90                  95

Leu Val His Gln Arg Trp Pro Phe Arg Tyr Ile Pro Arg Lys Gly Tyr
            100                 105                 110

Leu Lys Arg Leu Tyr Met Ala His Arg Met His His Ala Val Arg Gly
        115                 120                 125

Lys Glu Gly Cys Val Ser Phe Gly Phe Leu Tyr Ala Pro Pro Leu Ser
    130                 135                 140

Lys Leu Gln Ala Thr Leu Arg Glu Arg His Ala Ala Arg Ser Gly Ala
145                 150                 155                 160

Ala Arg Asp Glu Gln Asp Gly Val Asp Thr Ser Ser Ser Gly Lys
            165                 170                 175

<210> SEQ ID NO 13
<211> LENGTH: 25
<212> TYPE: DNA
<213> ORGANISM: Artificial sequence
<220> FEATURE:
<223> OTHER INFORMATION: Primer used to amplify crt gene cluster.

<400> SEQUENCE: 13
atgacggtct gcgcaaaaaa acacg                                          25

<210> SEQ ID NO 14
<211> LENGTH: 28
<212> TYPE: DNA
<213> ORGANISM: Artificial sequence
<220> FEATURE:
<223> OTHER INFORMATION: Primer used to amplify crt gene cluster.

<400> SEQUENCE: 14
gagaaattat gttgtggatt tggaatgc                                       28

<210> SEQ ID NO 15
<211> LENGTH: 21
<212> TYPE: DNA
<213> ORGANISM: Artificial sequence
<220> FEATURE:
<223> OTHER INFORMATION: Primer Tn5PCRF

<400> SEQUENCE: 15
gctgagttga aggatcagat c                                              21
```

```
<210> SEQ ID NO 16
<211> LENGTH: 21
<212> TYPE: DNA
<213> ORGANISM: Artificial sequence
<220> FEATURE:
<223> OTHER INFORMATION: Primer Tn5PCRR

<400> SEQUENCE: 16
cgagcaagac gtttcccgtt g                                              21

<210> SEQ ID NO 17
<211> LENGTH: 25
<212> TYPE: DNA
<213> ORGANISM: Artificial sequence
<220> FEATURE:
<223> OTHER INFORMATION: Primer Kan-2 FP-1

<400> SEQUENCE: 17
acctacaaca aagctctcat caacc                                          25

<210> SEQ ID NO 18
<211> LENGTH: 25
<212> TYPE: DNA
<213> ORGANISM: Artificial sequence
<220> FEATURE:
<223> OTHER INFORMATION: Primer Kan-2 RP-1

<400> SEQUENCE: 18
gcaatgtaac atcagagatt ttgag                                          25

<210> SEQ ID NO 19
<211> LENGTH: 3159
<212> TYPE: DNA
<213> ORGANISM: Escherichia coli

<400> SEQUENCE: 19
atgcctgtta taactcttcc tgatggcagc caacgccatt acgatcacgc tgtaagcccc     60
atggatgttg cgctggacat tggtccaggt ctggcgaaag cctgtatcgc agggcgcgtt    120
aatggcgaac tggttgatgc ttgcgatctg attgaaaacg acgcacaact gtcgatcatt    180
accgccaaag acgaagaagg tctggagatc attcgtcact cctgtgcgca cctgttaggg    240
cacgcgatta acaactttg gccgcatacc aaaatggcaa tcggcccggt tattgacaac    300 ggttttatt cgacgttga tcttgaccgc acgttaaccc aggaagatgt cgaagcactc    360
gagaagcgga tgcatgagct tgctgagaaa aactacgacg tcattaagaa gaaagtcagc    420
tggcacgaag cgcgtgaaac tttcgccaac cgtggggaga gctacaaagt ctccattctt    480
gacgaaaaca tcgcccatga tgacaagcca ggtctgtact ccatgaaga atatgtcgat    540 atgtgccgcg gtccgcacgt accgaacatg cgtttctgcc atcatttcaa actaatgaaa    600
acggcagggg cttactggcg tggcgacagc aacaacaaaa tgttgcaacg tatttacggt    660
acggcgtggg cagacaaaaa agcacttaac gcttacctgc agcgcctgga agaagccgcg    720
aaacgcgacc accgtaaaat cggtaaacag ctcgacctgt accatatgca ggaagaagcg    780
ccgggtatgg tattctggca caacgacggc tggaccatct tccgtgaact ggaagtgttt    840
gttcgttcta aactgaaaga gtaccagtat caggaagtta aggtccgtt catgatggac    900 cgtgtcctgt gggaaaaaac cggtcactgg acaactaca agatgcaat gttcaccaca    960 tcttctgaga accgtgaata ctgcattaag ccgatgaact gcccgggtca cgtacaaatt   1020
```

```
ttcaaccagg ggctgaagtc ttatcgcgat ctgccgctgc gtatggccga gtttggtagc   1080
tgccaccgta acgagccgtc aggttcgctg catggcctga tgcgcgtgcg tggatttacc   1140
caggatgacg cgcatatctt ctgtactgaa aacaaattc gcgatgaagt taacggatgt    1200
atccgtttag tctatgatat gtacagcact tttggcttcg agaagatcgt cgtcaaactc   1260
tccactcgtc ctgaaaaacg tattggcagc gacgaaatgt gggatcgtgc tgaggcggac   1320
ctggcggttg cgctggaaga aaacaacatc ccgtttgaat atcaactggg tgaaggcgct   1380
ttctacggtc cgaaaattga atttacccta tgactgcc tcgatcgtgc atggcagtgc     1440
ggtacagtac agctggactt ctctttgccg ctcgtctga cgcttctta tgtaggcgaa     1500 gacaatgaac gtaaagtacc ggtaatgatt caccgcgcaa ttctggggtc gatggaacgt   1560
ttcatcggta tcctgaccga agagttcgct ggtttcttcc cgacctggct tgcgccggtt   1620
caggttgtta tcatgaatat taccgattca cagtctgaat acgttaacga attgacgcaa   1680
aaactatcaa atgcgggcat tcgtgttaaa gcagacttga aaatgagaa gattggcttt   1740 aaaatccgcg agcacacttt gcgtcgcgtc ccatatatgc tggtctgtgg tgataaagag   1800
gtggaatcag gcaaagttgc cgttcgcacc cgccgtggta aagacctggg aagcatggac   1860
gtaaatgaag tgatcgagaa gctgcaacaa gagattcgca gccgcagtct taaacctgtc   1920
tcttatacac atctcaacca tcatcgatga attgtgtctc aaaatctctg atgttacatt   1980
gcacaagata aaatatatc atcatgaaca ataaaactgt ctgcttacat aaacagtaat     2040 acaagggtg ttatgagcca tattcaacgg gaaacgtctt gctcgaggcc gcgattaaat     2100
tccaacatgg atgctgattt atatgggtat aaatgggctc gcgataatgt cggcaatca     2160 ggtgcgacaa tctatcgatt gtatgggaag cccgatgcgc cagagttgtt tctgaaacat    2220
ggcaaaggta gcgttgccaa tgatgttaca gatgagatgg tcagactaaa ctggctgacg    2280 gaattatgc ctcttccgac catcaagcat tttatccgta ctcctgatga tgcatggtta     2340
ctcaccactg cgatccccgg aaaaacagca ttccaggtat tagaagaata tcctgattca    2400
ggtgaaaata ttgttgatgc gctggcagtg ttcctgcgcc ggttgcattc gattcctgtt    2460
tgtaattgtc cttttaacag cgatcgcgta tttcgtctcg ctcaggcgca atcacgaatg    2520
aataacggtt tggttgatgc gagtgatttt gatgacgagc gtaatggctg gcctgttgaa    2580
caagtctgga agaaatgca taaacttttg ccattctcac cggattcagt cgtcactcat    2640
ggtgatttct cacttgataa ccttattttt gacgagggga aattaatagg ttgtattgat    2700
gttggacgag tcggaatcgc agaccgatac caggatcttg ccatcctatg gaactgcctc    2760
ggtgagtttt ctccttcatt acagaaacgg ctttttcaaa aatatggtat tgataatcct    2820
gatatgaata aattgcagtt tcatttgatg ctcgatgagt ttttctaatc agaattggtt    2880
aattggttgt aacactggca gagcattacg ctgacttgac gggacggcgg ctttgttgaa    2940
taaatcgaac ttttgctgag ttgaaggatc agatcacgca tcttcccgac aacgcagacc    3000
gttccgtggc aaagcaaaag ttcaaaatca ccaactggtc cacctacaac aaagctctca    3060
tcaaccgtgg cggggatcct ctagagtcga cctgcaggca tgcaagcttc agggttgaga    3120
tgtgtataag agacaggtct taaacaattg gaggaataa                           3159
```

<210> SEQ ID NO 20
<211> LENGTH: 3171
<212> TYPE: DNA
<213> ORGANISM: Escherichia coli

<400> SEQUENCE: 20

-continued

```
atgatgagtt atgtagactg gccgccatta attttgaggc acacgtacta catggctgaa      60
ttcgaaacca cttttgcaga tctgggcctg aaggctccta tccttgaagc ccttaacgat     120
ctgggttacg aaaaaccatc tccaattcag gcagagtgta ttccacatct gctgaatggc     180
cgcgacgttc tgggtatggc ccagacgggg agcggaaaaa ctgcagcatt ctctttacct     240
ctgttgcaga atcttgatcc tgagctgaaa gcaccacaga ttctggtgct ggcaccgacc     300
cgcgaactgg cggtacaggt tgctgaagca atgacggatt tctctaaaca catgcgcggc     360
gtaaatgtgg ttgctctgta cggcggccag cgttatgacg tgcaattacg cgccctgcgt     420
caggggccgc agatcgttgt cggtactccg ggccgtctgc tggaccacct gaaacgtggc     480
actctggacc tctctaaact gagcggtctg gttctggatg aagctgacga aatgctgcgc     540
atgggcttca tcgaagacgt tgaaaccatt atggcgcaga tcccggaagg tcatcagacc     600
gctctgttct ctgcaaccat gccggaagcg attcgtcgca ttacccgccg ctttatgaaa     660
gagccgcagg aagtgcgcat tcagtccagc gtgactaccc gtcctgacat cagccagagc     720
tactggactg tctggggtat gcgcaaaaac gaagcactgg tacgctgtct cttatacaca     780
tctcaaccat catcgatgaa ttgtgtctca aaatctctga tgttacattg cacaagataa     840
aaatatatca tcatgaacaa taaaactgtc tgcttacata acagtaata caaggggtgt     900
tatgagccat attcaacggg aaacgtcttg ctcgaggccg cgattaaatt ccaacatgga     960
tgctgattta tatgggtata atgggctcg cgataatgtc gggcaatcag gtgcgacaat    1020
ctatcgattg tatgggaagc ccgatgcgcc agagttgttt ctgaaacatg gcaaaggtag    1080
cgttgccaat gatgttacag atgagatggt cagactaaac tggctgacgg aatttatgcc    1140
tcttccgacc atcaagcatt ttatccgtac tcctgatgat gcatggttac tcaccactgc    1200
gatccccgga aaacagcat tccaggtatt agaagaatat cctgattcag gtgaaaatat    1260
tgttgatgcg ctggcagtgt tcctgcgccg gttgcattcg attcctgttt gtaattgtcc    1320
ttttaacagc gatcgcgtat ttcgtctcgc tcaggcgcaa tcacgaatga ataacggttt    1380
ggttgatgcg agtgattttg atgacgagcg taatggctgg cctgttgaac aagtctggaa    1440
agaaatgcat aaacttttgc cattctcacc ggattcagtc gtcactcatg gtgatttctc    1500
acttgataac cttatttttg acgaggggaa attaataggt tgtattgatg ttggacgagt    1560
cggaatcgca gaccgatacc aggatcttgc catcctatgg aactgcctcg gtgagttttc    1620
tccttcatta cagaaacggc ttttttcaaaa atatggtatt gataatcctg atatgaataa    1680
attgcagttt catttgatgc tcgatgagtt tttctaatca gaattggtta attggttgta    1740
acactggcag agcattacgc tgacttgacg ggacggcggc tttgttgaat aaatcgaact    1800
tttgctgagt tgaaggatca gatcacgcat cttcccgaca acgcagaccg ttccgtggca    1860
aagcaaaagt tcaaaatcac caactggtcc acctacaaca aagctctcat caaccgtggc    1920
ggggatcctc tagagtcgac ctgcaggcat gcaagcttca gggttgagat gtgtataaga    1980
gacagactgg tacgtttcct ggaagcggaa gattttgatg cggcgattat cttcgttcgt    2040
accaaaaacg cgactctgga agtggctgaa gctcttgagc gtaacggcta caacagcgcc    2100
gcgctgaacg gtgacatgaa ccaggcgctg cgtgaacaga cactggaacg cctgaaagat    2160
ggtcgtctgg acatcctgat tgcgaccgac gttgcagccc gtggcctgga cgttgagcgt    2220
atcagcctgg tagttaacta cgatatcccg atggattctg agtcttacgt tcaccgtatc    2280
ggtcgtaccg gtcgtgcggg tcgtgctggc cgcgcgctgc tgttcgttga gaccgcgag    2340
```

```
cgtcgtctgc tgcgcaacat tgaacgtact atgaagctga ctattccgga agtagaactg    2400
ccgaacgcag aactgctagg caaacgccgt ctggaaaaat cgccgctaa agtacagcag     2460 cagctggaaa gcagcgatct ggatcaatac cgcgcactgc tgagcaaaat tcagccgact    2520
gctgaaggtg aagagctgga tctcgaaact ctggctgcgg cactgctgaa aatggcacag    2580
ggtgaacgta ctctgatcgt accgccagat gcgccgatgc gtccgaaacg tgaattccgt    2640
gaccgtgatg accgtggtcc gcgcgatcgt aacgaccgtg gcccgcgtgg tgaccgtgaa    2700
gatcgtccgc gtcgtgaacg tcgtgatgtt ggcgatatgc agctgtaccg cattgaagtg    2760
ggccgcgatg atggtgttga agttcgtcat atcgttggtg cgattgctaa cgaaggcgac    2820
atcagcagcc gttacattgg taacatcaag ctgtttgctt ctcactccac catcgaactg    2880
ccgaaaggta tgccgggtga agtgctgcaa cactttacgc gcactcgcat tctcaacaag    2940
ccgatgaaca tgcagttact gggcgatgca cagccgcata ctggcggtga gcgtcgtggc    3000
ggtggtcgtg gtttcggtgg cgaacgtcgt gaaggcggtc gtaacttcag cggtgaacgc    3060
cgtgaaggtg gccgtggtga tggtcgtcgt tttagcggcg aacgtcgtga aggccgcgct    3120
ccgcgtcgtg atgattctac cggtcgtcgt cgtttcggtg gtgatgcgta a            3171

<210> SEQ ID NO 21
<211> LENGTH: 2904
<212> TYPE: DNA
<213> ORGANISM: Escherichia coli

<400> SEQUENCE: 21
atgactgaat cttttgctca actctttgaa gagtccttaa agaaatcga acccgcccg      60 ggttctatcg ttcgtggcgt tgttgttgct atcgacaaag acgtagtact ggttgacgct    120
ggtctgaaat ctgagtccgc catcccggct gagcagttca aaaacgccca gggcgagctg    180
gaaatccagg taggtgacga agttgacgtt gctctggacg cagtagaaga cggcttcggt    240
gaaactctgc tgtcccgtga gaaagctaaa cgtcacgaag cctggatcac gctggaaaaa    300
gcttacgaag atgctgaaac tgttaccggt gttatcaacg caaagttaa gggcggcttc    360 actgttgagc tgaacggtat tcgtgcgttc ctgccaggtt ctctggtaga cgttcgtccg    420
gtgcgtgaca ctctgcacct ggaaggcaaa gagcttgaat ttaaagtaat caagctggat    480
cagaagcgca caacgttgt tgtttctcgt cgtgccgtta tcgaatccga aaacagcgca    540
gagcgcgatc agctgctgga aaacctgcag gaaggcatgg aagttaaagg tatcgttaag    600
aacctcactg actacggtgc attcgttgat ctgggcggcg ttgacggcct gctgcacatc    660
actgacatgg cctggaaacg cgttaagcat ccgagcgaaa tcgtcaacgt gggcgacgaa    720
atcactgtta aagtgctgaa gttcgaccgc gaacgtaccc gtgtatccct gggcctgaaa    780
cagctgggcg aagatccgtg ggtagctatc gctaaacgtt atccggaagg taccaaactg    840
actggtcgcg tgaccaacct gaccgactac ggctgcttcg ttgaaatcga agaaggcgtt    900
gaaggcctgg tacacgtttc cgaaatggac tggaccaaca aaaacatcca cccgtccaaa    960
gttgttaacg ttggcgatgt agtggaagtt atggttctgg atatcgacga gaacgtcgt    1020 cgtatctccc tgggtctgaa acagtgcaaa gctaacccgt ggcagcagtt cgcggaaacc    1080
cacaacaagg cgaccgtgt tgaaggtaaa atcaagtcta tcactgactt cggtatcttc    1140
atcggcttgg acggcggcat cgacggcctg gttcacctgt ctgacatctc ctggaacgtt    1200
gcaggcgaag aagcagttcg tgaatacaaa aaaggcgacg aaatcgctgc agttgttctg    1260
caggttgacg cagaacgtga acgtatctcc ctgggcgtta acagctcgc agaagatccg    1320
```

-continued

```
ttcaacaact gggttgctct gaacaagaaa ggcgctatcg taaccggtaa agtaactgca    1380
gttgacgcta aaggcgcaac cgtagaactg gctgacggcg ttgaaggtta cctgcgtgct    1440
tctgaagcat cccgtgaccg cgttaagac gctaccctgg ttctgagcgt tggcgacgaa    1500
gttgaagcta aattcaccgg cgttgatcgt aaaaaccgcg caatcagcct gtctgttcgt    1560
gcgaaagacg aagctgacga gaaagatgca atcgcaactg tctcttatac acatctcaac    1620
cctgaagctt gcatgcctgc aggtcgactc tagaggatcc ccgccacggt tgatgagagc    1680
tttgttgtag gtggaccagt tggtgatttt gaacttttgc tttgccacgg aacggtctgc    1740
gttgtcggga agatgcgtga tctgatcctt caactcagca aaagttcgat ttattcaaca    1800
aagccgccgt cccgtcaagt cagcgtaatg ctctgccagt gttacaacca attaaccaat    1860
tctgattaga aaactcatc gagcatcaaa tgaaactgca atttattcat atcaggatta    1920
tcaataccat atttttgaaa aagccgtttc tgtaatgaag gagaaaactc accgaggcag    1980
ttccatagga tggcaagatc ctggtatcgg tctgcgattc cgactcgtcc aacatcaata    2040
caacctatta atttccctc gtcaaaaata aggttatcaa gtgagaaatc accatgagtg    2100
acgactgaat ccggtgagaa tggcaaaagt ttatgcattt cttccagac ttgttcaaca    2160 ggccagccat tacgctcgtc atcaaaatca ctcgcatcaa ccaaaccgtt attcattcgt    2220
gattgcgcct gagcgagacg aaatacgcga tcgctgttaa aaggacaatt acaaacagga    2280
atcgaatgca accggcgcag gaacactgcc agcgcatcaa caatattttc acctgaatca    2340
ggatattctt ctaatacctg gaatgctgtt tttccgggga tcgcagtggt gagtaaccat    2400
gcatcatcag gagtacggat aaaatgcttg atggtcggaa gaggcataaa ttccgtcagc    2460
cagtttagtc tgaccatctc atctgtaaca tcattggcaa cgctacctt gccatgtttc    2520 agaaacaact ctggcgcatc gggcttccca tacaatcgat agattgtcgc acctgattgc    2580
ccgacattat cgcgagccca tttatacca tataaatcag catccatgtt ggaatttaat    2640
cgcggcctcg agcaagacgt ttcccgttga atatggctca taacacccct tgtattactg    2700
tttatgtaag cagacagttt tattgttcat gatgatatat ttttatcttg tgcaatgtaa    2760
catcagagat tttgagacac aattcatcga tgatggttga gatgtgtata agagacagca    2820
atcgcaactg ttaacaaaca ggaagatgca aacttctcca caacgcaat ggctgaagct    2880 ttcaaagcag ctaaaggcga gtaa                                          2904
```

```
<210> SEQ ID NO 22
<211> LENGTH: 5454
<212> TYPE: DNA
<213> ORGANISM: Escherichia coli

<400> SEQUENCE: 22
```

```
gtgaaagatt tattaaagtt tctgaaagcg cagactaaaa ccgaagagtt tgatgcgatc      60
aaaattgctc tggcttcgcc agacatgatc cgttcatggt ctttcggtga agttaaaaag     120
ccggaaacca tcaactaccg tacgttcaaa ccagaacgtg acggcctttt ctgcgcccgt     180
atctttgggc cggtaaaaga ttacgagtgc ctgtgcggta agtacaagcg cctgaaacac     240
cgtggcgtca tctgtgagaa gtgcggcgtt gaagtgaccc agactaaagt acgccgtgag     300
cgtatgggcc acatcgaact ggcttccccg actgcgcaca tctggttcct gaaatcgctg     360
ccgtcccgta tcggtctgct gctcgatatg ccgctgcgcg atatcgaacg cgtactgtac     420
tttgaatcct atgtggttat cgaaggcggt atgaccaacc tggaacgtca gcagatcctg     480
```

-continued

```
actgaagagc agtatctgga cgcgctggaa gagttcggtg acgaattcga cgcgaagatg      540
ggggcggaag caatccaggc tctgctgaag agcatggatc tggagcaaga gtgcgaacag      600
ctgcgtgaag agctgaacga aaccaactcc gaaaccaagc gtaaaaagct gaccaagcgt      660
atcaaactgc tggaagcgtt cgttcagtct ggtaacaaac cagagtggat gatcctgacc      720
gttctgccgg tactgccgcc agatctgcgt ccgctggttc cgctggatgg tggtcgtttc      780
gcgacttctg acctgaacga tctgtatcgt cgcgtcatta accgtaacaa ccgtctgaaa      840
cgtctgctgg atctggctgc gccggacatc atcgtacgta acgaaaaacg tatgctgcag      900
gaagcggtag acgccctgct ggataacggt cgtcgcggtc gtgcgatcac cggttctaac      960
aagcgtcctc tgaaatcttt ggccgacatg atcaaaggta acagggtcg tttccgtcag     1020 aacctgctcg gtaagcgtgt tgactactcc ggtcgttctg taatcaccgt aggtccatac     1080
ctgcgtctgc atcagtgcgg tctgccgaag aaaatggcac tggagctgtt caaaccgttc     1140
atctacggca agctggaact gcgtggtctt gctaccacca ttaaagctgc gaagaaaatg     1200
gttgagcgcg aagaagctgt cgtttgggat atcctggacg aagttatccg gaacacccg      1260 gtactgctga accgtgcacc gactctgcac cgtctgggta tccaggcatt tgaaccggta     1320
ctgatcgaag gtaaagctat ccagctgcac ccgctggttt gtgcggcata taacgccgac     1380
ttcgatggtg accagatggc tgttcacgta ccgctgacgc tggaagccca gctggaagcg     1440
cgtgcgctga tgatgtctac caacaacatc ctgtccccgg cgaacggcga accaatcatc     1500
gttccgtctc aggacgttgt actgggtctg tactacatga cccgtgactg tgttaacgcc     1560
aaaggcgaag gcatggtgct gactggcccg aaagaagcag aacgtctgta tcgctctggt     1620
ctggcttctc tgcatgcgcg cgttaaagtg cgtatcaccg agtatgaaaa agatgctaac     1680
ggtgaattag tagcgaaaac cagcctgaaa gacacgactg ttggccgtgc cattctgtgg     1740
atgattgtac cgaaaggtct gccttactcc atcgtcaacc aggcgctggg taaaaaagca     1800
atctccaaaa tgctgaacac ctgctaccgc attctcggtc tgaaaccgac cgttattttt     1860
gcggaccaga tcatgtacac cggcttcgcc tatgcagcgc gttctggtgc atctgttggt     1920
atcgatgaca tggtcatccc ggagaagaaa cacgaaatca tctccgaggc agaagcagaa     1980
gttgctgaaa ttcaggagca gttccagtct ggtctggtaa ctgcgggcga acgctacaac     2040
aaagttatcg atatctgggc tgcggcgaac gatcgtgtat ccaaagcgat gatggataac     2100
ctgcaaactg aaaccgtgat taaccgtgac ggtcaggaag agaagcaggt ttccttcaac     2160
agcatctaca tgatggccga ctccggtgcg cgtggttctg cggcacagat tcgtcagctt     2220
gctggtatgc gtggtctgat ggcgaagccg atggctcca tcatcgaaac gccaatcacc      2280
gcgaacttcc gtgaaggtct gaacgtactc cagtacttca tctccaccca cggtgctcgt     2340
aaaggtctgg cggataccgc actgaaaact gcgaactccg gttacctgac tcgtcgtctg     2400
gttgacgtgg cgcaggacct ggtggttacc gaagacgatt gtggtaccca tgaaggtatc     2460
atgatgactc cggttatcga gggtggtgac gttaaagagc cgctgcgcga tcgcgtactg     2520
ggtcgtgtaa ctgctgaaga cgttctgaag ccgggtactg ctgatatcct cgttccgcgc     2580
aacacgctgc tgcacgaaca gtggtgtgac ctgctggaag agaactctgt cgacgcggtt     2640
aaagtacgtt ctgttgtatc ttgtgacacc gactttggtg tatgtgcgca ctgctacggt     2700
cgtgacctgg cgcgtggcca catcatcaac aagggtgaag caatcggtgt tatcgcggca     2760
cagtccatcg tgaaccggg tacacagctg accatgcgta cgttccacat cggtggtgcg     2820
gcatctcgtg cggctgctga atccagcatc caagtgaaaa acaaaggtag catcaagctc     2880
```

```
agcaacgtga agtcggttgt gaactccagc ggtaaactgg ttatcacttc ccgtaatact   2940
gaactgaaac tgatcgacga attcggtcgt actaaagaaa gctacaaagt accttacggt   3000
gcggtactgg cgaaaggcga tggcgaacag gttgctggcg cgaaaccgt tgcaaactgg    3060
gacccgcaca ccatgccggt tatcaccgaa gtaagcggtt ttgtacgctt tactgacatg   3120
atcgacggcc agaccattac gcgtcagacc gacgaactga ccggtctgtc ttcgctggtg   3180
gttctggatt ccgcagaacg taccgcaggt ggtaaagatc tgcgtccggc actgaaaatc   3240
gttgatgctc agggtaacga cgttctgatc ccaggtaccg atatgccagc gcagtacttc   3300
ctgccgggta aagcgattgt tcagctggaa gatggcgtac agatcagctc tggtgacacc   3360
ctggcgcgta ttccgcagga atccggcggt accaaggaca tcaccggtgg tctgccgcgc   3420
gttgcggacc tgttcgaagc acgtcgtccg aaagagccgg caatcctggc tgaaatcagc   3480
ggtatcgttt ccttcggtaa agaaaccaaa ggtaaacgtc gtctggttat cacccccggta  3540
gacggtagcg atccgtacga agagatgatt ccgaaatggc gtcagctcaa cgtgttcgaa   3600
ggtgaacgtg tagaacgtgg tgacgtaatt ccgacggtc cggaagcgcc gcacgacatt    3660
ctgcgtctgc gtggtgttca tgctgttact cgttacatcg ttaacgaagt acaggacgta   3720
taccgtctgc agggcgttaa gattaacgat aaacacatcg aagttatcgt tcgtcagatg   3780
ctgcgtaaag ctaccatcgt taacgcgggt agctccgact tcctggaagg cgaacaggtt   3840
gaatactctc gcgtcaagat cgcaaaccgc gaactggaag cgaacggcaa agtgggtgca   3900
acttactccc gcgatctgct gggtatcacc aaagcgtctc tggcaaccga gtccttcatc   3960
tccgcggcat cgttccagga gaccactcgc gtgctgaccg aagcagccgt tgcgggcaaa   4020
cgcgacgaac tgcgcggcct gaaagagaac gttatcgtgg gtcgtctgat cccggcaggt   4080
accggttacg cgtaccacca ggatcgtatg cgtcgccgtg ctgcgggtga agctctgtct   4140
cttatacaca tctcaacccct gaagcttgca tgcctgcagg tcgactctag aggatccccg   4200
ccacggttga tgagagcttt gttgtaggtg gaccagttgg tgattttgaa cttttgcttt   4260
gccacggaac ggtctgcgtt gtcgggaaga tgcgtgatct gatccttcaa ctcagcaaaa   4320
gttcgattta ttcaacaaag ccgccgtccc gtcaagtcag cgtaatgctc tgccagtgtt   4380
acaaccaatt aaccaattct gattagaaaa actcatcgag catcaaatga aactgcaatt   4440
tattcatatc aggattatca ataccatatt tttgaaaaag ccgtttctgt aatgaaggag   4500
aaaactcacc gaggcagttc cataggatgg caagatcctg gtatcggtct gcgattccga   4560
ctcgtccaac atcaatacaa cctattaatt tcccctcgtc aaaaataagg ttatcaagtg   4620
agaaatcacc atgagtgacg actgaatccg gtgagaatgg caaaagttta tgcatttctt   4680
tccagacttg ttcaacaggc cagccattac gctcgtcatc aaaatcactc gcatcaacca   4740
aaccgttatt cattcgtgat tgcgcctgag cgagacgaaa tacgcgatcg ctgttaaaag   4800
gacaattaca acaggaatc gaatgcaacc ggcgcaggaa cactgccagc gcatcaacaa   4860
tattttcacc tgaatcagga tattcttcta atacctggaa tgctgttttt ccggggatcg   4920
cagtggtgag taaccatgca tcatcaggag tacggataaa atgcttgatg gtcggaagag   4980
gcataaattc cgtcagccag tttagtctga ccatctcatc tgtaacatca ttggcaacgc   5040
tacctttgcc atgtttcaga aacaactctg gcgcatcggg cttcccatac aatcgataga   5100
ttgtcgcacc tgattgcccg acattatcgc gagcccattt ataccatat aaatcagcat   5160
ccatgttgga atttaatcgc ggcctcgagc aagacgtttc ccgttgaata tggctcataa   5220
```

-continued

| | |
|---|---|
| caccccttgt attactgttt atgtaagcag acagttttat tgttcatgat gatatatttt | 5280 |
| tatcttgtgc aatgtaacat cagagatttt gagacacaat tcatcgatga tggttgagat | 5340 |
| gtgtataaga gacagggtga agctccggct gcaccgcagg tgactgcaga agacgcatct | 5400 |
| gccagcctgg cagaactgct gaacgcaggt ctgggcggtt ctgataacga gtaa | 5454 |

<210> SEQ ID NO 23
<211> LENGTH: 1845
<212> TYPE: DNA
<213> ORGANISM: Escherichia coli

<400> SEQUENCE: 23

| | |
|---|---|
| atgggcaaaa catctatgat acacgcaatt gtggatcaat atagtcactg tgaatgggtg | 60 |
| gaaaatagca tgagtgccaa tgaaaacaac ctgatttgga tcgatcttga gatgaccggt | 120 |
| ctggatcccg agcgcgatcg cattattgag attgccacgc tggtgaccga tgccaacctg | 180 |
| aatattctgg cagaagggcc gaccattgca gtacaccagt ctgatgaaca gctggcgctg | 240 |
| atggatgact ggaacgtgcg cacccatacc gccagcgggc tggtagagcg cgtgaaagcg | 300 |
| agcacgatgg gcgatcggga agctgaactg caacgctcg aatttttaaa acagtgggtg | 360 |
| cctgcgggaa aatcgccgat ttgcggtaac agcatcggtc aggaccgtcg tttcctgttt | 420 |
| aaatacatgc cggagctgga agcctacttc cactaccgtt atctcgatgt cagcaccctg | 480 |
| aaagagctgg cgcgccgctg aagccggaa attctggatg gttttaccaa gcaggggacg | 540 |
| catcaggcga tggatgatat ccgtgaatcg gtggcggagc tggcttacta cctgtctctt | 600 |
| atacacatct caaccctgaa gcttgcatgc ctgcaggtcg actctagagg atccccgcca | 660 |
| cggttgatga gagcttttgtt gtaggtggac cagttggtga ttttgaactt ttgctttgcc | 720 |
| acggaacggt ctgcgttgtc gggaagatgc gtgatctgat ccttcaactc agcaaaagtt | 780 |
| cgatttattc aacaaagccg ccgtcccgtc aagtcagcgt aatgctctgc cagtgttaca | 840 |
| accaattaac caattctgat tagaaaaact catcgagcat caaatgaaac tgcaatttat | 900 |
| tcatatcagg attatcaata ccatattttt gaaaagccg tttctgtaat gaaggagaaa | 960 |
| actcaccgag gcagttccat aggatggcaa gatcctggta tcggtctgcg attccgactc | 1020 |
| gtccaacatc aatacaacct attaatttcc cctcgtcaaa aataaggtta tcaagtgaga | 1080 |
| aatcaccatg agtgacgact gaatccggtg agaatggcaa aagtttatgc atttctttcc | 1140 |
| agacttgttc aacaggccag ccattacgct cgtcatcaaa atcactcgca tcaaccaaac | 1200 |
| cgttattcat tcgtgattgc gcctgagcga acgaaatac gcgatcgctg ttaaaaggac | 1260 |
| aattacaaac aggaatcgaa tgcaaccggc gcaggaacac tgccagcgca tcaacaatat | 1320 |
| tttcacctga atcaggatat tcttctaata cctggaatgc tgttttccg gggatcgcag | 1380 |
| tggtgagtaa ccatgcatca tcaggagtac ggataaaatg cttgatggtc ggaagaggca | 1440 |
| taaattccgt cagccagttt agtctgacca tctcatctgt aacatcattg gcaacgctac | 1500 |
| ctttgccatg tttcagaaac aactctggcg catcgggctt cccatacaat cgatagattg | 1560 |
| tcgcacctga ttgcccgaca ttatcgcgag cccatttata cccatataaa tcagcatcca | 1620 |
| tgttggaatt taatcgcggc ctcgagcaag acgtttcccg ttgaatatgg ctcataacac | 1680 |
| cccttgtatt actgtttatg taagcagaca gttttattgt tcatgatgat atatttttat | 1740 |
| cttgtgcaat gtaacatcag agattttgag acacaattca tcgatgatgg ttgagatgtg | 1800 |
| tataagagac aggcttacta ccgcgagcat tttatcaagc tgtaa | 1845 |

<210> SEQ ID NO 24
<211> LENGTH: 2334
<212> TYPE: DNA
<213> ORGANISM: Escherichia coli

<400> SEQUENCE: 24

| | | | | | |
|---|---|---|---|---|---|
| atgaagccaa | tttttagccg | tggcccgtcg | ctacagattc | gccttattct | ggcggtgctg | 60 |
| gtggcgctcg | gcattattat | tgccgacagc | cgcctgggga | cgttcagtca | aatccgtact | 120 |
| tatatggata | ccgccgtcag | tcctttctac | tttgtttcca | atgctcctcg | tgaattgctg | 180 |
| gatggcgtat | cgcagacgct | ggcctcgcgt | gaccaattag | aacttgaaaa | ccgggcgtta | 240 |
| cgtcaggaac | tgttgctgaa | aacagtgaa | ctgctgatgc | ttggacaata | caaacaggag | 300 |
| aacgcgcgtc | tgcgcgagct | gctgggttcc | ccgctgcgtc | aggatgagca | gaaaatggtg | 360 |
| actcaggtta | tctccacggt | taacgatcct | tatagcgatc | aagttgttat | cgataaaggt | 420 |
| agcgttaatg | gcgtttatga | aggccagccg | gtcatcagcg | acaaaggtgt | tgttggtcag | 480 |
| gtggtggccg | tcgctaaact | gaccagtcgc | gtgctgctga | tttgtgatgc | gacccacgcg | 540 |
| ctgccaatcc | aggtgctgcg | caacgatatc | cgcgtaattg | cagccggtaa | cggttgtacg | 600 |
| gatgatttgc | agcttgagca | tctgccggcg | aatacggata | ttcgtgttgg | tgatgtgctg | 660 |
| gtgacttccg | gtctgggcgg | tcgtttcccg | gaaggctatc | cggtcgcggt | tgtctcttcc | 720 |
| gtaaaactcg | atacccagcg | cgcttatact | gtgattcagg | cgcgtccgac | tgcagggctg | 780 |
| caacgtttgc | gttatctgct | gctgctgtgg | gggcagatc | gtaacggcgc | taacccgatg | 840 |
| acgccggaag | aggtgcatcg | tgttgctaat | gaacgtctga | tgcagatgat | gccgcaggta | 900 |
| ttgccttcgc | cagacgcgat | ggggccaaag | ttacctgaac | cggcaacggg | gatcgctcag | 960 |
| ccgactccga | gcaaccggc | gacaggaaat | gcagctactg | cgcctgctgc | gccgacacag | 1020 |
| cctctgtctc | ttatacacat | ctcaaccatc | atcgatgaat | tgtgtctcaa | aatctctgat | 1080 |
| gttacattgc | acaagataaa | aatatatcat | catgaacaat | aaaactgtct | gcttacataa | 1140 |
| acagtaatac | aagggtgtt | atgagccata | ttcaacggga | aacgtcttgc | tcgaggccgc | 1200 |
| gattaaattc | caacatggat | gctgatttat | atgggtataa | atgggctcgc | gataatgtcg | 1260 |
| ggcaatcagg | tgcgacaatc | tatcgattgt | atgggaagcc | cgatgcgcca | gagttgtttc | 1320 |
| tgaaacatgg | caaggtagc | gttgccaatg | atgttacaga | tgagatggtc | agactaaact | 1380 |
| ggctgacgga | atttatgcct | cttccgacca | tcaagcattt | tatccgtact | cctgatgatg | 1440 |
| catggttact | caccactgcg | atccccggaa | aaacagcatt | ccaggtatta | gaagaatatc | 1500 |
| ctgattcagg | tgaaaatatt | gttgatgcgc | tggcagtgtt | cctgcgccgg | ttgcattcga | 1560 |
| ttcctgtttg | taattgtcct | tttaacagcg | atcgcgtatt | tcgtctcgct | caggcgcaat | 1620 |
| cacgaatgaa | taacggtttg | gttgatgcga | gtgattttga | tgacgagcgt | aatggctggc | 1680 |
| ctgttgaaca | agtctggaaa | gaaatgcata | aacttttgcc | attctcaccg | gattcagtcg | 1740 |
| tcactcatgg | tgatttctca | cttgataacc | ttattttga | cgaggggaaa | ttaataggtt | 1800 |
| gtattgatgt | tggacgagtc | ggaatcgcag | accgatacca | ggatcttgcc | atcctatgga | 1860 |
| actgcctcgg | tgagttttct | ccttcattac | agaaacggct | ttttcaaaaa | tatggtattg | 1920 |
| ataatcctga | tatgaataaa | ttgcagtttc | atttgatgct | cgatgagttt | ttctaatcag | 1980 |
| aattggttaa | ttggttgtaa | cactggcaga | gcattacgct | gacttgacgg | gacggcggct | 2040 |
| ttgttgaata | atcgaacttt | tgctgagtt | gaaggatcag | atcacgcatc | ttcccgacaa | 2100 |
| cgcagaccgt | tccgtggcaa | agcaaaagtt | caaaatcacc | aactggtcca | cctacaacaa | 2160 |

-continued

```
agctctcatc aaccgtggcg gggatcctct agagtcgacc tgcaggcatg caagcttcag    2220
ggttgagatg tgtataagag acagacacag cctgctgcta atcgctctcc acaaagggct    2280
acgccgccgc aaagtggtgc tcaaccgcct gcgcgtgcgc cgggagggca atag          2334
```

<210> SEQ ID NO 25
<211> LENGTH: 2676
<212> TYPE: DNA
<213> ORGANISM: Escherichia coli

<400> SEQUENCE: 25

```
atgcgaagtg aacagatttc tggctcgtca ctcaatccgt cttgtcgttt cagttcctgt      60
ctcttataca catctcaacc atcatcgatg aattgtgtct caaaatctct gatgttacat     120
tgcacaagat aaaaatatat catcatgaac aataaaactg tctgcttaca taaacagtaa     180
tacaaggggt gttatgagcc atattcaacg ggaaacgtct tgctcgaggc cgcgattaaa     240
ttccaacatg gatgctgatt tatatgggta taaatgggct cgcgataatg tcgggcaatc     300
aggtgcgaca atctatcgat tgtatgggaa gcccgatgcg ccagagttgt ttctgaaaca     360
tggcaaaggt agcgttgcca atgatgttac agatgagatg gtcagactaa actggctgac     420
ggaatttatg cctcttccga ccatcaagca ttttatccgt actcctgatg atgcatggtt     480
actcaccact gcgatccccg aaaaacagc attccaggta ttagaagaat atcctgattc     540
aggtgaaaat attgttgatg cgctggcagt gttcctgcgc cggttgcatt cgattcctgt     600
ttgtaattgt ccttttaaca gcgatcgcgt atttcgtctc gctcaggcgc aatcacgaat     660
gaataacggt ttggttgatg cgagtgattt tgatgacgag cgtaatggct ggcctgttga     720
acaagtctgg aaagaaatgc ataaactttt gccattctca ccggattcag tcgtcactca     780
tggtgatttc tcacttgata accttatttt tgacgagggg aaattaatag gttgtattga     840
tgttggacga gtcggaatcg cagaccgata ccaggatctt gccatcctat ggaactgcct     900
cggtgagttt tctccttcat tacagaaacg gctttttcaa aaatatggta ttgataatcc     960
tgatatgaat aaattgcagt ttcatttgat gctcgatgag ttttctaat cagaattggt    1020 taattggttg taacactggc agagcattac gctgacttga cgggacggcg gctttgttga    1080
ataaatcgaa cttttgctga gttgaaggat cagatcacgc atcttcccga caacgcagac    1140
cgttccgtgg caaagcaaaa gttcaaaatc accaactggt ccacctacaa caaagctctc    1200
atcaaccgtg gcggggatcc tctagagtcg acctgcaggc atgcaagctt cagggttgag    1260
atgtgtataa gagacagttt cagttctgcg tactctcctg tgaccaggca gcgaaaagac    1320
atgagtcgat gaccgtaaac aggcatggat gatcctgcca taccattcac aacattaagt    1380
tcgagattta ccccaagttt aagaactcac accactatga atcttaccga attaaagaat    1440
acgccggttt ctgagctgat cactctcggc gaaaatatgg ggctggaaaa cctggctcgt    1500
atgcgtaagc aggacattat ttttgccatc ctgaagcagc acgcaaagag tggcgaagat    1560
atctttggtg atggcgtact ggagatattg caggatggat ttggtttcct ccgttccgca    1620
gacagctcct acctcgccgg tcctgatgac atctacgttt ccctagcca aatccgccgt    1680 ttcaacctcc gcactggtga taccatctct ggtaagattc gcccgccgaa agaaggtgaa    1740
cgctattttg cgctgctgaa agttaacgaa gttaacttcg acaaacctga aacgcccgc    1800 aacaaaatcc tctttgagaa cttaaccccg ctgcacgcaa actctcgtct gcgtatggaa    1860
cgtggtaacg ttctactga agatttaact gctcgcgtac tggatctggc atcacctatc    1920
ggtcgtggtc agcgtggtct gattgtggca ccgccgaaag ccggtaaaac catgctgctg    1980
```

```
cagaacattg ctcagagcat tgcttacaac cacccggatt gtgtgctgat ggttctgctg    2040
atcgacgaac gtccggaaga agtaaccgag atgcagcgtc tggtaaaagg tgaagttgtt    2100
gcttctacct tgacgaacc cgcatctcgc cacgttcagg ttgcggaaat ggtgatcgag     2160
aaggccaaac gcctggttga gcacaagaaa gacgttatca ttctgctcga ctccatcact    2220
cgtctggcgc gcgcttacaa caccgttgtt ccggcgtcag gtaaagtgtt gaccggtggt    2280
gtggatgcca acgccctgca tcgtccgaaa cgcttctttg gtgcggcgcg taacgtggaa    2340
gagggcggca gcctgaccat tatcgcgacg gcgcttatcg ataccggttc taaaatggac    2400
gaagttatct acgaagagtt taaaggtaca ggcaacatgg aactgcacct ctctcgtaag    2460
atcgctgaaa aacgcgtctt cccggctatc gactacaacc gttctggtac ccgtaaagaa    2520
gagctgctca cgactcagga agaactgcag aaaatgtgga tcctgcgcaa aatcattcac    2580
ccgatgggcg aaatcgatgc aatggaattc ctcattaata aactggcaat gaccaagacc    2640
aatgacgatt tcttcgaaat gatgaaacgc tcataa                              2676

<210> SEQ ID NO 26
<211> LENGTH: 1746
<212> TYPE: DNA
<213> ORGANISM: Escherichia coli

<400> SEQUENCE: 26
atggattact tcaccctctt tggcttgcct gcccgctatc aactcgatac ccaggcgctg      60
agcctgcgtt ttcaggatct acaacgtcag tatcatcctg ataaattcgc cagcggaagc     120
caggcggaac aactcgccgc cgtacagcaa tctgcaacca ttaaccaggc ctggcaaacg     180
ctgcgtcatc cgttaatgcg cgcggaatat ttgctttctt tgcacggctt tgatctcgcc     240
agcgagcagc atacctgtct cttatacaca tctcaaccat catcgatgaa ttgtgtctca     300
aaatctctga tgttacattg cacaagataa aaatatatca tcatgaacaa taaaactgtc     360
tgcttacata acagtaata caaggggtgt tatgagccat attcaacggg aaacgtcttg      420
ctcgaggccg cgattaaatt ccaacatgga tgctgattta tatgggtata aatgggctcg     480
cgataatgtc gggcaatcag gtgcgacaat ctatcgattg tatgggaagc ccgatgcgcc    540
agagttgttt ctgaaacatg gcaaaggtag cgttgccaat gatgttacag atgagatggt    600
cagactaaac tggctgacgg aatttatgcc tcttccgacc atcaagcatt tatccgtac     660 tcctgatgat gcatggttac tcaccactgc gatccccgga aaaacagcat tccaggtatt    720
agaagaatat cctgattcag gtgaaaatat tgttgatgcg ctggcagtgt tcctgcgccg    780
gttgcattcg attcctgttt gtaattgtcc ttttaacagc gatcgcgtat ttcgtctcgc     840
tcaggcgcaa tcacgaatga ataacggttt ggttgatgcg agtgattttg atgacgagcg    900
taatggctgg cctgttgaac aagtctggaa agaaatgcat aaacttttgc cattctcacc    960
ggattcagtc gtcactcatg gtgatttctc acttgataac cttatttttg acgaggggaa   1020
attaataggt tgtattgatg ttggacgagt cggaatcgca gaccgatacc aggatcttgc   1080
catcctatgg aactgcctcg gtgagttttc tccttcatta cagaaacggc ttttttcaaaa   1140 atatggtatt gataatcctg atatgaataa attgcagttt catttgatgc tcgatgagtt   1200
tttctaatca gaattggtta attggttgta acactggcag agcattacgc tgacttgacg   1260
ggacggcggc tttgttgaat aaatcgaact tttgctgagt tgaaggatca gatcacgcat   1320
cttcccgaca acgcagaccg ttccgtggca aagcaaaagt tcaaaatcac caactggtcc   1380
```

| | | | | |
|---|---|---|---|---|
| acctacaaca | aagctctcat | caaccgtggc | ggggatcctc | tagagtcgac ctgcaggcat | 1440 |
| gcaagcttca | gggttgagat | gtgtataaga | gacaggcagc | atactgtgcg cgacaccgcg | 1500 |
| ttcctgatgg | aacagttgga | gctgcgcgaa | gagctggacg | agatcgaaca ggcgaaagat | 1560 |
| gaagcgcggc | tggaaagctt | tatcaaacgt | gtgaaaaaga | tgtttgatac ccgccatcag | 1620 |
| ttgatggttg | aacagttaga | caacgagacg | tgggacgcgg | cggcggatac cgtgcgtaag | 1680 |
| ctgcgttttc | tcgataaact | gcgaagcagt | gccgaacaac | tcgaagaaaa actgctcgat | 1740 |
| ttttaa | | | | | 1746 |

<210> SEQ ID NO 27
<211> LENGTH: 3171
<212> TYPE: DNA
<213> ORGANISM: Escherichia coli

<400> SEQUENCE: 27

| | | | | |
|---|---|---|---|---|
| atgatgagtt | atgtagactg | gccgccatta | attttgaggc | acacgtacta catggctgaa | 60 |
| ttcgaaacca | cttttgcaga | tctgggcctg | aaggctccta | tccttgaagc ccttaacgat | 120 |
| ctgggttacg | aaaaaccatc | tccaattcag | gcagagtgta | ttccacatct gctgaatggc | 180 |
| cgcgacgttc | tgggtatggc | ccagacgggg | agcggaaaaa | ctgcagcatt ctctttacct | 240 |
| ctgttgcaga | tcttgatcc | tgagctgaaa | gcaccacaga | ttctggtgct ggcaccgacc | 300 |
| cgcgaactgg | cggtacaggt | tgctgaagca | atgacggatt | tctctaaaca catgcgcggc | 360 |
| gtaaatgtgg | ttgctctgta | cggcggccag | cgttatgacg | tgcaattacg cgccctgcgt | 420 |
| caggggccgc | agatcgttgt | cggtactccg | ggccgtctgc | tggaccacct gaaacgtggc | 480 |
| actctggacc | tctctaaact | gagcggtctg | gttctggatg | aagctgacga atgctgcgc | 540 |
| atgggcttca | tcgaagacgt | tgaaaccatt | atggcgcaga | tcccggaagg tcatcagacc | 600 |
| gctctgttct | ctgcaaccat | gccggaagcg | attcgtcgca | ttacccgccg ctttatgaaa | 660 |
| gagccgcagg | aagtgcgcat | tcagtccagc | gtgactaccc | gtcctgacat cagccagagc | 720 |
| tactggactg | tctggggtat | gcgcaaaaac | gaagcactgg | tacgctgtct cttatacaca | 780 |
| tctcaaccat | catcgatgaa | ttgtgtctca | aaatctctga | tgttacattg cacaagataa | 840 |
| aaatatatca | tcatgaacaa | taaaactgtc | tgcttacata | aacagtaata caaggggtgt | 900 |
| tatgagccat | attcaacggg | aaacgtcttg | ctcgaggccg | cgattaaatt ccaacatgga | 960 |
| tgctgattta | tatgggtata | aatgggctcg | cgataatgtc | gggcaatcag gtgcgacaat | 1020 |
| ctatcgattg | tatgggaagc | ccgatgcgcc | agagttgttt | ctgaaacatg gcaaaggtag | 1080 |
| cgttgccaat | gatgttacag | atgagatggt | cagactaaac | tggctgacgg aatttatgcc | 1140 |
| tcttccgacc | atcaagcatt | ttatccgtac | tcctgatgat | gcatggttac tcaccactgc | 1200 |
| gatccccgga | aaaacagcat | tccaggtatt | agaagaatat | cctgattcag gtgaaaatat | 1260 |
| tgttgatgcg | ctggcagtgt | tcctgcgccg | gttgcattcg | attcctgttt gtaattgtcc | 1320 |
| ttttaacagc | gatcgcgtat | ttcgtctcgc | tcaggcgcaa | tcacgaatga ataacggttt | 1380 |
| ggttgatgcg | agtgattttg | atgacgagcg | taatggctgg | cctgttgaac aagtctggaa | 1440 |
| agaaatgcat | aaacttttgc | cattctcacc | ggattcagtc | gtcactcatg gtgatttctc | 1500 |
| acttgataac | cttatttttg | acgaggggaa | attaataggt | tgtattgatg ttggacgagt | 1560 |
| cggaatcgca | gaccgatacc | aggatcttgc | catcctatgg | aactgcctcg gtgagttttc | 1620 |
| tccttcatta | cagaaacggc | tttttcaaaa | atatggtatt | gataatcctg atatgaataa | 1680 |
| attgcagttt | catttgatgc | tcgatgagtt | tttctaatca | gaattggtta attggttgta | 1740 |

-continued

```
acactggcag agcattacgc tgacttgacg ggacggcggc tttgttgaat aaatcgaact      1800
tttgctgagt tgaaggatca gatcacgcat cttcccgaca acgcagaccg ttccgtggca      1860
aagcaaaagt tcaaaatcac caactggtcc acctacaaca aagctctcat caaccgtggc      1920
ggggatcctc tagagtcgac ctgcaggcat gcaagcttca gggttgagat gtgtataaga      1980
gacagactgg tacgttttcct ggaagcggaa gattttgatg cggcgattat cttcgttcgt     2040
accaaaaacg cgactctgga agtggctgaa gctcttgagc gtaacggcta caacagcgcc      2100
gcgctgaacg tgacatgaa ccaggcgctg cgtgaacaga cactggaacg cctgaaagat       2160
ggtcgtctgg acatcctgat tgcgaccgac gttgcagccc gtggcctgga cgttgagcgt      2220
atcagcctgg tagttaacta cgatatcccg atggattctg agtcttacgt tcaccgtatc      2280
ggtcgtaccg gtcgtgcggg tcgtgctggc cgcgcgctgc tgttcgttga aaccgcgag       2340
cgtcgtctgc tgcgcaacat tgaacgtact atgaagctga ctattccgga agtagaactg      2400
ccgaacgcag aactgctagg caaacgccgt ctggaaaaat cgccgctaa agtacagcag       2460
cagctggaaa gcagcgatct ggatcaatac cgcgcactgc tgagcaaaat tcagccgact      2520
gctgaaggtg aagagctgga tctcgaaact ctggctgcgg cactgctgaa aatggcacag      2580
ggtgaacgta ctctgatcgt accgccagat gcgccgatgc gtccgaaacg tgaattccgt      2640
gaccgtgatg accgtggtcc gcgcgatcgt aacgaccgtg gcccgcgtgg tgaccgtgaa      2700
gatcgtccgc gtcgtgaacg tcgtgatgtt ggcgatatgc agctgtaccg cattgaagtg      2760
ggccgcgatg atggtgttga agttcgtcat atcgttggtg cgattgctaa cgaaggcgac      2820
atcagcagcc gttacattgg taacatcaag ctgtttgctt ctcactccac catcgaactg      2880
ccgaaggta tgccgggtga agtgctgcaa cactttacgc gcactcgcat tctcaacaag      2940
ccgatgaaca tgcagttact gggcgatgca cagccgcata ctggcggtga gcgtcgtggc      3000
ggtggtcgtg gtttcggtgg cgaacgtcgt gaaggcggtc gtaacttcag cggtgaacgc      3060
cgtgaaggtg gccgtggtga tggtcgtcgt tttagcggcg aacgtcgtga aggccgcgct      3120
ccgcgtcgtc atgattctac cggtcgtcgt cgtttcggtg gtgatgcgta a               3171
```

<210> SEQ ID NO 28
<211> LENGTH: 8609
<212> TYPE: DNA
<213> ORGANISM: Artificial sequence
<220> FEATURE:
<223> OTHER INFORMATION: Plasmid pPCB15

<400> SEQUENCE: 28

```
cgtatggcaa tgaaagacgg tgagctggtg atatgggata gtgttcaccc ttgttacacc        60
gttttccatg agcaaactga aacgttttca tcgctctgga gtgaatacca cgacgatttc       120
cggcagtttc tacacatata ttcgcaagat gtggcgtgtt acggtgaaaa cctggcctat       180
ttccctaaag ggtttattga gaatatgttt ttcgtctcag ccaatccctg ggtgagtttc       240
accagttttg atttaaacgt ggccaatatg gacaacttct tcgcccccgt tttcaccatg       300
ggcaaatatt atacgcaagg cgacaaggtg ctgatgccgc tggcgattca ggttcatcat       360
gccgtctgtg atggcttcca tgtcggcaga atgcttaatg aattacaaca gtactgcgat       420
gagtggcagg gcggggcgta attttttttaa ggcagttatt ggtgcctaga aatatttttat     480
ctgattaata agatgatctt cttgagatcg ttttggtctg cgcgtaatct cttgctctga       540
aaacgaaaaa accgccttgc agggcggttt ttcgaaggtt ctctgagcta ccaactcttt       600
```

-continued

```
gaaccgaggt aactggcttg gaggagcgca gtcaccaaaa cttgtccttt cagtttagcc    660
ttaaccggcg catgacttca agactaactc ctctaaatca attaccagtg gctgctgcca    720
gtggtgcttt tgcatgtctt tccgggttgg actcaagacg atagttaccg gataaggcgc    780
agcggtcgga ctgaacgggg ggttcgtgca tacagtccag cttggagcga actgcctacc    840
cggaactgag tgtcaggcgt ggaatgagac aaacgcggcc ataacagcgg aatgacaccg    900
gtaaaccgaa aggcaggaac aggagagcgc acgagggagc cgccagggga aacgcctggt    960
atctttatag tcctgtcggg tttcgccacc actgatttga gcgtcagatt tcgtgatgct   1020
tgtcaggggg gcggagccta tggaaaaacg ctttgccgc ggccctctca cttccctgtt   1080
aagtatcttc ctggcatctt ccaggaaatc tccgccccgt tcgtaagcca tttccgctcg   1140
ccgcagtcga acgaccgagc gtagcgagtc agtgagcgag gaagcggaat atatcctgta   1200
tcacatattc tgctgacgca ccggtgcagc ctttttctc ctgccacatg aagcacttca   1260
ctgacaccct catcagtgcc aacatagtaa gccagtatat acactccgct agcgcccaat   1320
acgcaaaccg cctctccccg cgcgttggcc gattcattaa tgcagctggc acgacaggtt   1380
tcccgactgg aaagcgggca gtgagcgcaa cgcaattaat gtgagttagc tcactcatta   1440
ggcaccccag gctttacact ttatgcttcc ggctcgtatg ttgtgtggaa ttgtgagcgg   1500
ataacaattt cacacaggaa acagctatga ccatgattac gaattcgagc tcggtaccca   1560
aacgaattcg ccttttgac ggtctgcgca aaaaaacacg ttcaccttac tggcatttcg   1620
gctgagcagt tgctggctga tatcgatagc cgccttgatc agttactgcc ggttcagggt   1680
gagcgggatt gtgtgggtgc cgcgatgcgt gaaggcacgc tggcaccggg caaacgtatt   1740
cgtccgatgc tgctgttatt aacagcgcgc gatcttggct gtgcgatcag tcacggggga   1800
ttactggatt tagcctgcgc ggttgaaatg gtgcatgctg cctcgctgat tctggatgat   1860
atgccctgca tggacgatgc gcagatgcgt cgggggcgtc ccaccattca cacgcagtac   1920
ggtgaacatg tggcgattct ggcggcggtc gctttactca gcaaagcgtt tggggtgatt   1980
gccgaggctg aaggtctgac gccgatagcc aaaactcgcg cggtgtcgga gctgtccact   2040
gcgattggca tgcagggtct ggttcagggc cagtttaagg acctctcgga aggcgataaa   2100
ccccgcagcg ccgatgccat actgctaacc aatcagttta aaccagcac gctgttttgc   2160 gcgtcaacgc aaatggcgtc cattgcggcc aacgcgtcct gcgaagcgcg tgagaacctg   2220
catcgtttct cgctcgatct cggccaggcc tttcagttgc ttgacgatct taccgatggc   2280
atgaccgata ccggcaaaga catcaatcag gatgcaggta aatcaacgct ggtcaattta   2340
ttaggctcag gcgcggtcga agaacgcctg cgacagcatt tgcgcctggc cagtgaacac   2400 cttccgcgg catgccaaaa cggccattcc accacccaac tttttattca ggcctggttt   2460
gacaaaaaac tcgctgccgt cagttaagga tgctgcatga gccattttgc ggtgatcgca   2520 ccgcccttt tcagccatgt tcgcgctctg caaaaccttg ctcaggaatt agtggcccgc   2580
ggtcatcgtg ttacgttttt tcagcaacat gactgcaaag cgctggtaac gggcagcgat   2640
atcggattcc agaccgtcgg actgcaaacg catcctcccg gttccttatc gcacctgctg   2700
cacctggccg cgcacccact cggaccctcg atgttacgac tgatcaatga aatggcacgt   2760
accagcgata tgctttgccg ggaactgccc gccgcttttc atgcgttgca gatagagggc   2820
gtgatcgttg atcaaatgga gccggcaggt gcagtagtcg cagaagcgtc aggtctgccg   2880
tttgtttcgg tggcctgcgc gctgccgctc aaccgcgaac cgggtttgcc tctggcggtg   2940
atgcctttcg agtacggcac cagcgatgcg gctcgggaac gctataccac cagcgaaaaa   3000
```

```
atttatgact ggctgatgcg acgtcacgat cgtgtgatcg cgcatcatgc atgcagaatg   3060
ggtttagccc cgcgtgaaaa actgcatcat tgtttttctc cactggcaca aatcagccag   3120
ttgatccccg aactggattt tccccgcaaa gcgctgccag actgctttca tgcggttgga   3180
ccgttacggc aaccccaggg gacgccgggg tcatcaactt cttattttcc gtccccggac   3240
aaacccgta ttttgcctc gctgggcacc ctgcagggac atcgttatgg cctgttcagg    3300
accatcgcca aagcctgcga agaggtggat gcgcagttac tgttggcaca ctgtggcggc   3360
ctctcagcca cgcaggcagg tgaactggcc cggggcgggg acattcaggt tgtggatttt   3420
gccgatcaat ccgcagcact ttcacaggca cagttgacaa tcacacatgg tgggatgaat   3480
acggtactgg acgctattgc ttcccgcaca ccgctactgg cgctgccgct ggcatttgat   3540
caacctggcg tggcatcacg aattgtttat catggcatcg gcaagcgtgc gtctcggttt   3600
actaccagcc atgcgctggc gcggcagatt cgatcgctgc tgactaacac cgattacccg   3660
cagcgtatga caaaaattca ggccgcattg cgtctggcag gcggcacacc agccgccgcc   3720
gatattgttg aacaggcgat gcggacctgt cagccagtac tcagtgggca ggattatgca   3780
accgcactat gatctcattc tggtcggtgc cggtctggct aatggcctta tcgcgctccg   3840
gcttcagcaa cagcatccgg atatgcggat cttgcttatt gaggcgggtc ctgaggcggg   3900
agggaaccat acctggtcct ttcacgaaga ggatttaacg ctgaatcagc atcgctggat   3960
agcgccgctt gtggtccatc actggcccga ctaccaggtt cgtttccccc aacgccgtcg   4020
ccatgtgaac agtggctact actgcgtgac ctcccgcat ttcgccggga tactccggca    4080
acagtttgga caacatttat ggctgcatac cgcggtttca gccgttcatg ctgaatcgt    4140
ccagttagcg gatggccgga ttattcatgc cagtacagtg atcgacgac gggttacac     4200
gcctgattct gcactacgcg taggattcca ggcatttatc ggtcaggagt ggcaactgag   4260
cgcgccgcat ggtttatcgt caccgattat catggatgcg acggtcgatc agcaaaatgg   4320
ctaccgcttt gtttataccc tgccgctttc cgcaaccgca ctgctgatcg aagacacaca   4380
ctacattgac aaggctaatc ttcaggccga acgggcgcgt cagaacattc gcgattatgc   4440
tgcgcgacag ggttggccgt tacagacgtt gctgcgggaa gaacagggtg cattgcccat   4500
tacgttaacg ggcgataatc gtcagttttg gcaacagcaa ccgcaagcct gtagcggatt   4560
acgcgccggg ctgtttcatc cgacaaccgg ctactcccta ccgctcgcgg tggcgctggc   4620
cgatcgtctc agcgcgctgg atgtgtttac ctcttcctct gttcaccaga cgattgctca   4680
cttttgcccag caacgttggc agcaacaggg gttttttccgc atgctgaatc gcatgttgtt   4740
tttagccgga ccgccgagt cacgctggcg tgtgatgcag cgtttctatg gcttacccga    4800
ggatttgatt gcccgctttt atgcgggaaa actcaccgtg accgatcggc tacgcattct   4860
gagcggcaag ccgcccgttc ccgttttcgc ggcattgcag gcaattatga cgactcatcg   4920
ttgaagagcg actacatgaa accaactacg gtaattggtg cgggctttgg tggcctggca   4980
ctggcaattc gtttacaggc cgcaggtatt cctgttttgc tgcttgagca gcgcgacaag   5040
ccgggtggcc gggcttatgt ttatcaggag cagggcttta cttttgatgc aggccctacc   5100
gttatcaccg atcccagcgc gattgaagaa ctgtttgctc tggccggtaa acagcttaag   5160
gattacgtcg agctgttgcc ggtcacgccg ttttatcgcc tgtgctggga gtccggcaag   5220
gtcttcaatt acgataacga ccaggcccag ttagaagcgc agatacagca gtttaatccg   5280
cgcgatgttg cgggttatcg agcgttcctt gactattcg gtgccgtatt caatgagggc    5340
```

```
tatctgaagc tcggcactgt gccttttta tcgttcaaag acatgcttcg ggccgcgccc    5400
cagttggcaa agctgcaggc atggcgcagc gtttacagta aagttgccgg ctacattgag    5460
gatgagcatc ttcggcaggc gttttctttt cactcgctct tagtgggggg gaatccgttt    5520
gcaacctcgt ccatttatac gctgattcac gcgttagaac gggaatgggg cgtctggttt    5580
ccacgcggtg gaaccggtgc gctggtcaat ggcatgatca agctgtttca ggatctgggc    5640
ggcgaagtcg tgcttaacgc ccgggtcagt catatggaaa ccgttgggga caagattcag    5700
gccgtgcagt tggaagacgg cagacggttt gaaacctgcg cggtggcgtc gaacgctgat    5760
gttgtacata cctatcgcga tctgctgtct cagcatcccg cagccgctaa gcaggcgaaa    5820
aaactgcaat ccaagcgtat gagtaactca ctgtttgtac tctattttgg tctcaaccat    5880
catcacgatc aactcgccca tcataccgtc tgttttgggc cacgctaccg tgaactgatt    5940
cacgaaattt ttaaccatga tggtctggct gaggattttt cgctttattt acacgcacct    6000
tgtgtcacgg atccgtcact ggcaccgaaa gggtgcggca gctattatgt gctggcgcct    6060
gttccacact taggcacggc gaacctcgac tgggcggtag aaggaccccg actgcgcgat    6120
cgtatttttg actaccttga gcaacattac atgcctggct gcgaagcca gttggtgacg    6180
caccgtatgt ttacgccgtt cgatttccgc gacgagctca atgcctggca aggttcggcc    6240
ttctcggttg aacctattct gacccagagc gcctggttcc gaccacataa ccgcgataag    6300
cacattgata atctttatct ggttggcgca ggcacccatc ctggcgcggg cattcccggc    6360
gtaatcggct cggcgaaggc gacggcaggc ttaatgctgg aggacctgat ttgacgaata    6420
cgtcattact gaatcatgcc gtcgaaacca tggcggttgg ctcgaaaagc tttgcgactg    6480
catcgacgct tttcgacgcc aaaacccgtc gcagcgtgct gatgctttac gcatggtgcc    6540
gccactgcga cgacgtcatt gacgatcaaa cactgggctt tcatgccgac cagccctctt    6600
cgcagatgcc tgagcagcgc ctgcagcagc ttgaaatgaa aacgcgtcag gcctacgccg    6660
gttcgcaaat gcacgagccc gcttttgccg cgtttcagga ggtcgcgatg cgcatgata    6720
tcgctcccgc ctacgcgttc gaccatctgg aaggttttgc catggatgtg cgcgaaacgc    6780
gctacctgac actggacgat acgctgcgtt attgctatca cgtcgccggt gttgtgggcc    6840
tgatgatggc gcaaattatg ggcgttcgcg ataacgccac gctcgatcgc gcctgcgatc    6900
tcgggctggc tttccagttg accaacattg cgcgtgatat tgtcgacgat gctcaggtgg    6960
gccgctgtta tctgcctgaa agctggctgg aagaggaagg actgacgaaa gcgaattatg    7020
ctgcgccaga aaaccggcag gccttaagcc gtatcgccgg gcgactggta cgggaagcgg    7080
aaccctatta cgtatcatca atggccggtc tggcacaatt acccttacgc tcggcctggg    7140
ccatcgcgac agcgaagcag gtgtaccgta aaattggcgt gaaagttgaa caggccggta    7200
agcaggcctg ggatcatcgc cagtccacgt ccaccgccga aaattaacg cttttgctga    7260
cggcatccgg tcaggcagtt acttcccgga tgaagacgta tccacccgt cctgctcatc    7320
tctggcagcg cccgatctag ccgcatgcct ttctctcagc gtcgcctgaa gtttagataa    7380
cggtggcgcg tacagaaaac caaaggacac gcagccctct tttcccctta cagcatgatg    7440
catacggtgg gccatgtata accgtttcag gtagcctttg cgcggtatgt agcggaacgg    7500
ccagcgctgt tgtaccagtc cgtcgtggac cataaaatac agtaaaccat aagcggtcat    7560
gcctgcacca atccactgga gcggccagat tcctgtactg ccgaagtaaa tcaggcaat    7620
cgacacaatg gcgaatacca cggcatagag atcgttaact tcaaatgcgc ctttacgcgg    7680
ttcatgatgt gaaagatgcc agccccaacc ccagccgtgc atgatgtatt tatgtgccag    7740
```

```
tgcagcaacc acttccatgc cgaccacggt gacaaacacg atcagggcat tccaaatcca      7800
caacataatt tctcaagggc gaattcgcgg ggatcctcta gagtcgacct gcaggcatgc      7860
aagcttggca ctggccgtcg ttttacaacg tcgtgactgg gaaaaccctg gcgttaccca      7920
acttaatcgc cttgcagcac atcccccttt cgccagctgg cgtaatagcg aagaggcccg      7980
caccgatcgc ccttcccaac agttgcgcag cctgaatggc gaatggcgct gatgtccggc      8040
ggtgcttttg ccgttacgca ccacccgtc agtagctgaa caggagggac agctgataga       8100
aacagaagcc actggagcac ctcaaaaaca ccatcataca ctaaatcagt aagttggcag      8160
catcacccga cgcactttgc gccgaataaa tacctgtgac ggaagatcac ttcgcagaat      8220
aaataaatcc tggtgtccct gttgataccg ggaagccctg ggccaacttt tggcgaaaat      8280
gagacgttga tcggcacgta agaggttcca actttcacca taatgaaata agatcactac      8340
cgggcgtatt ttttgagtta tcgagatttt caggagctaa ggaagctaaa atggagaaaa      8400
aaatcactgg ataccacc gttgatatat cccaatggca tcgtaaagaa catttgagg        8460 catttcagtc agttgctcaa tgtacctata accagaccgt tcagctggat attacggcct     8520 tttaaagac cgtaaagaaa ataagcaca agttttatcc ggcctttatt cacattcttg       8580
cccgcctgat gaatgctcat ccggaattt                                        8609
```